(12) United States Patent
Shroff et al.

(10) Patent No.: US 9,615,882 B2
(45) Date of Patent: *Apr. 11, 2017

(54) METHODS AND DEVICES FOR APPLYING ENERGY TO BODILY TISSUES

(71) Applicant: MicroCube, LLC, Fremont, CA (US)

(72) Inventors: Ketan Shroff, Pleasanton, CA (US); Chun Yiu Chu, Oakland, CA (US); Dinesh I. Mody, San Jose, CA (US); Clarence Emmons, Capitola, CA (US); Amrish J. Walke, Milpitas, CA (US)

(73) Assignee: MicroCube, LLC, Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/635,980

(22) Filed: Mar. 2, 2015

(65) Prior Publication Data

US 2015/0313670 A1    Nov. 5, 2015

Related U.S. Application Data

(63) Continuation of application No. 12/603,077, filed on Oct. 21, 2009, now Pat. No. 8,968,287.

(Continued)

(51) Int. Cl.
*A61B 18/18* (2006.01)
*A61B 18/00* (2006.01)

(52) U.S. Cl.
CPC .......... *A61B 18/18* (2013.01); *A61B 18/1815* (2013.01); *A61B 2018/00351* (2013.01); *A61B 2018/00422* (2013.01); *A61B 2018/00452* (2013.01); *A61B 2018/00488* (2013.01); *A61B 2018/00494* (2013.01);

(Continued)

(58) Field of Classification Search
CPC ................ A61B 18/18; A61B 18/1815; A61B 2018/00559; A61B 2018/183; A61B 2018/1861; A61B 2018/1884; A61B 2018/1892
See application file for complete search history.

(56) References Cited

U.S. PATENT DOCUMENTS 4,583,556 A    4/1986  Hines et al.
4,658,836 A    4/1987  Turner
(Continued)

FOREIGN PATENT DOCUMENTS

EP    1145686       10/2001
JP    2005-312807   11/2005
(Continued)

*Primary Examiner* — Ronald Hupczey, Jr.
(74) *Attorney, Agent, or Firm* — Levine Bagade Han LLP

(57) ABSTRACT

Devices and methods for treating tissue with microwave energy used in applications such as destroying a soft tissue by microwave ablation and/or creating point, line, area or volumetric lesions. Various embodiments of flexible, low-profile devices are also disclosed where such device can be inserted non-invasively or minimally invasively near or into the target tissue such as cardiac tissue. The devices disclosed herein comprise antennas wherein the field profile generated by an antenna is tailored and optimized for a particular clinical application. The antennas use unique properties of microwaves such as interaction of a microwave field with one or more conductive or non-conductive shaping elements to shape or redistribute the microwave field.

20 Claims, 55 Drawing Sheets

Related U.S. Application Data

(60) Provisional application No. 61/107,252, filed on Oct. 21, 2008, provisional application No. 61/162,241, filed on Mar. 20, 2009, provisional application No. 61/180,133, filed on May 21, 2009, provisional application No. 61/222,409, filed on Jul. 1, 2009.

(52) U.S. Cl.
CPC ............ *A61B 2018/00505* (2013.01); *A61B 2018/00511* (2013.01); *A61B 2018/00517* (2013.01); *A61B 2018/00523* (2013.01); *A61B 2018/00529* (2013.01); *A61B 2018/00547* (2013.01); *A61B 2018/00559* (2013.01); *A61B 2018/00577* (2013.01); *A61B 2018/00702* (2013.01); *A61B 2018/00726* (2013.01); *A61B 2018/00791* (2013.01); *A61B 2018/00839* (2013.01); *A61B 2018/00875* (2013.01); *A61B 2018/00982* (2013.01); *A61B 2018/00994* (2013.01); *A61B 2018/1846* (2013.01); *A61B 2018/1853* (2013.01); *A61B 2018/1861* (2013.01); *A61B 2018/1869* (2013.01)

(56) References Cited

U.S. PATENT DOCUMENTS

| | | |
|---|---|---|
| 4,700,716 A | 10/1987 | Kasevich et al. |
| 5,007,437 A | 4/1991 | Sterzer |
| 5,277,201 A | 1/1994 | Stern |
| 5,449,380 A | 9/1995 | Chin |
| 5,603,697 A | 2/1997 | Grundy et al. |
| 5,741,249 A | 4/1998 | Moss et al. |
| 5,769,880 A | 6/1998 | Truckai et al. |
| 5,788,692 A | 8/1998 | Campbell et al. |
| 5,861,021 A | 1/1999 | Thome et al. |
| 5,902,251 A | 5/1999 | vanHooydonk |
| 5,928,145 A | 7/1999 | Ocali et al. |
| 6,471,696 B1 * | 10/2002 | Berube ............... A61B 18/1492 606/33 |
| 6,635,055 B1 | 10/2003 | Cronin |
| 6,663,625 B1 | 12/2003 | Ormsby et al. |
| 6,813,520 B2 | 11/2004 | Truckai et al. |
| 6,817,999 B2 | 11/2004 | Berube et al. |
| 6,929,642 B2 | 8/2005 | Xiao et al. |
| 7,197,363 B2 | 3/2007 | Prakesh et al. |
| 7,226,446 B1 | 6/2007 | Mody et al. |
| 7,864,160 B2 | 1/2011 | Geaghan et al. |
| 2003/0057413 A1 | 3/2003 | Kim et al. |
| 2003/0109868 A1 | 6/2003 | Chin |
| 2003/0163128 A1 | 8/2003 | Patil et al. |
| 2005/0240173 A1 | 10/2005 | Palti |
| 2006/0200119 A1 | 9/2006 | Vaska et al. |
| 2006/0293652 A1 | 12/2006 | van der Weide |
| 2007/0066972 A1 | 3/2007 | Ormsby et al. |
| 2007/0139294 A1 | 6/2007 | Dunn et al. |
| 2007/0179552 A1 | 8/2007 | Dennis et al. |
| 2007/0203480 A1 | 8/2007 | Mody et al. |
| 2008/0167664 A1 | 7/2008 | Payne et al. |
| 2009/0146439 A1 | 6/2009 | Watts et al. |
| 2010/0121319 A1 | 5/2010 | Chu et al. |
| 2010/0137857 A1 | 6/2010 | Shroff et al. |
| 2011/0004205 A1 | 1/2011 | Chu et al. |

FOREIGN PATENT DOCUMENTS

| | | |
|---|---|---|
| WO | WO 97/06739 | 2/1997 |
| WO | WO 03/053259 | 7/2003 |
| WO | WO 03/088858 | 10/2003 |
| WO | WO 2006/004585 | 1/2006 |
| WO | WO 2009/146439 | 12/2009 |
| WO | WO 2010/048335 | 4/2010 |
| WO | WO 2012/003232 | 1/2012 |
| WO | WO 2013/149245 | 10/2013 |

* cited by examiner

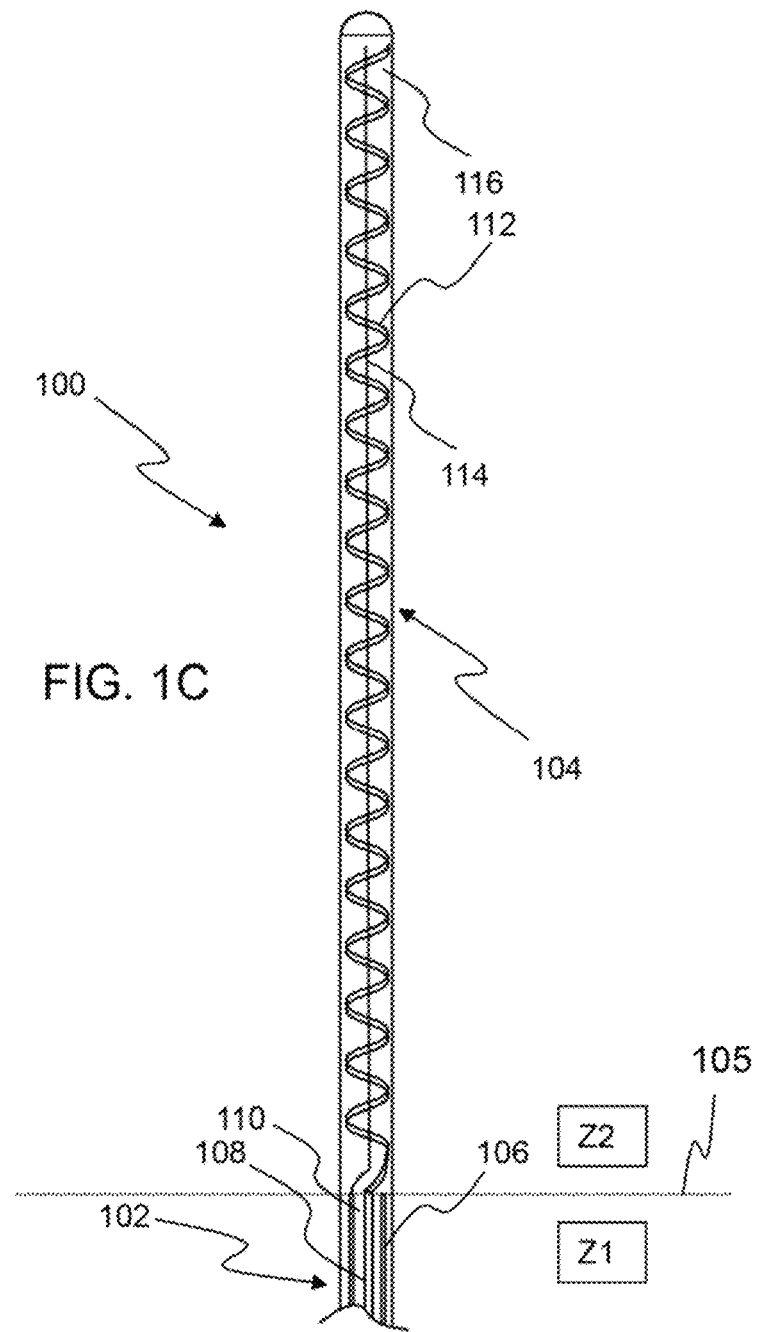

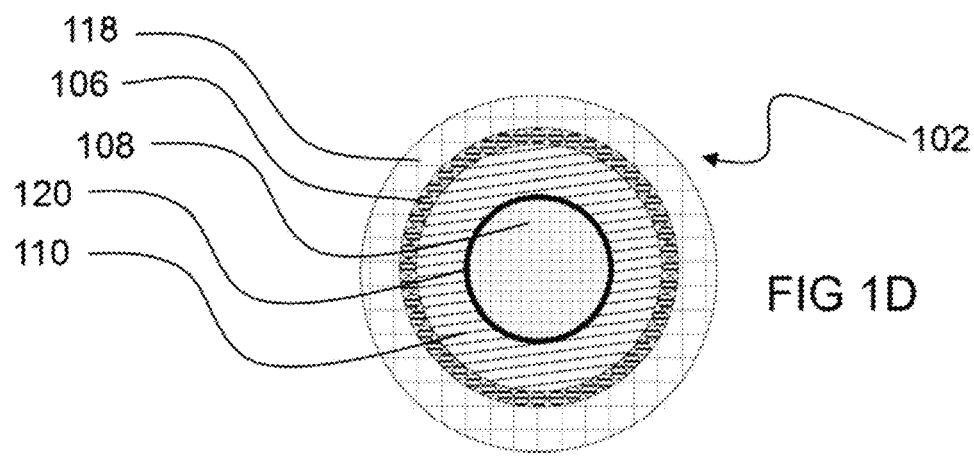
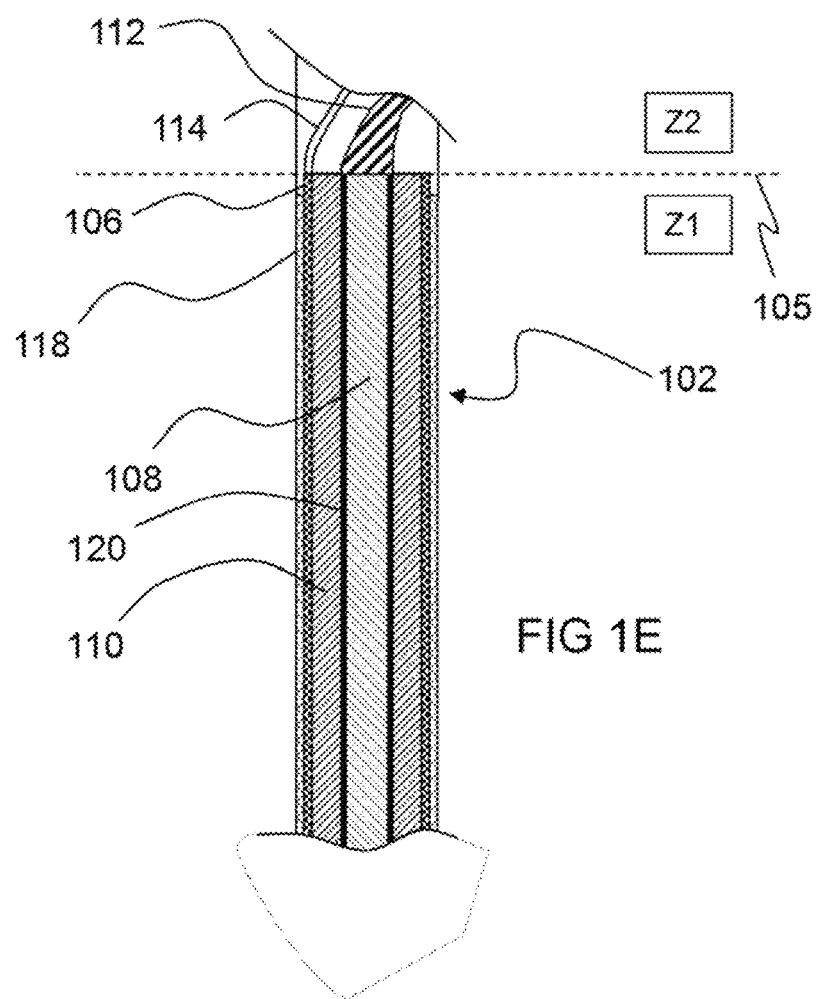

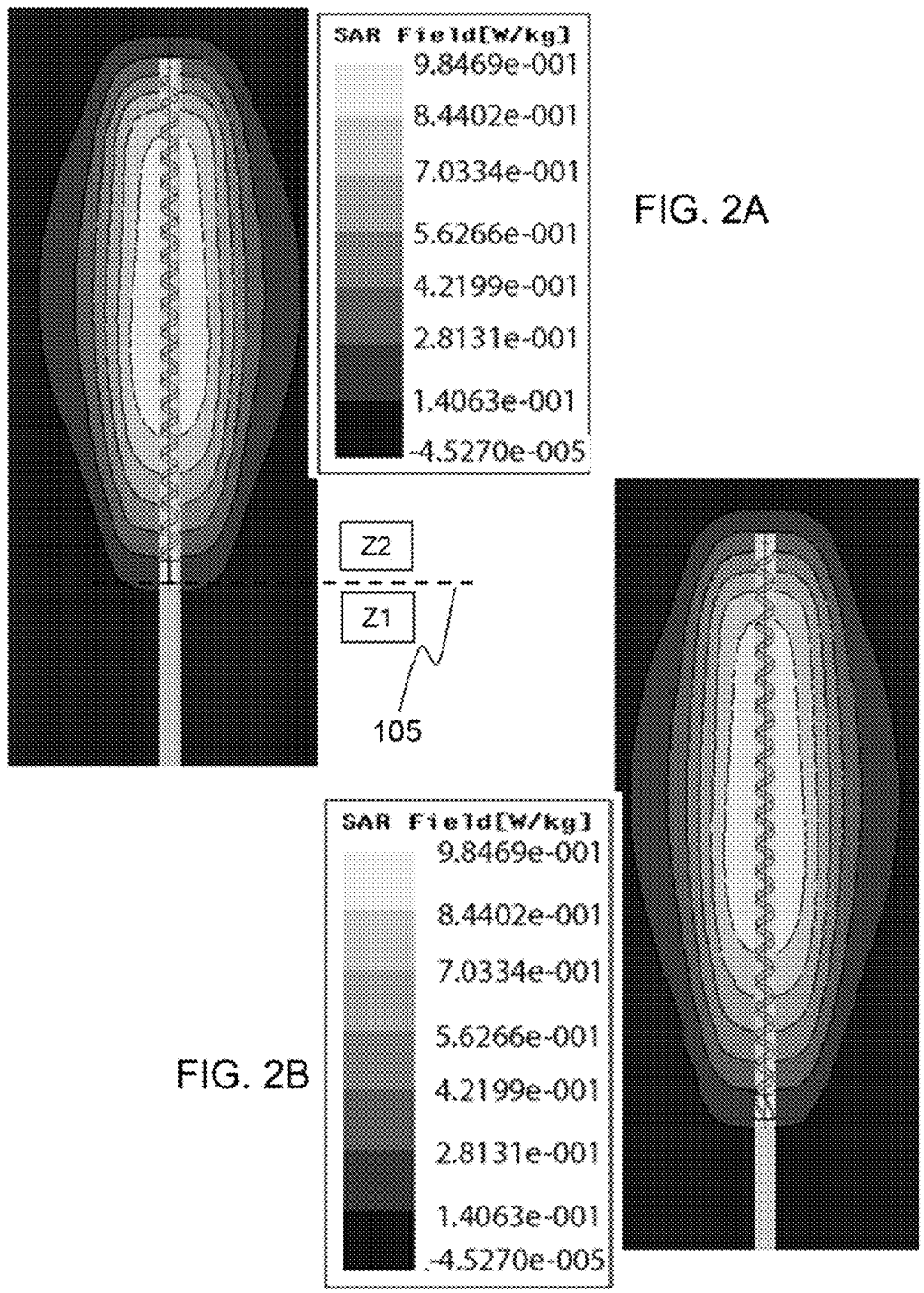

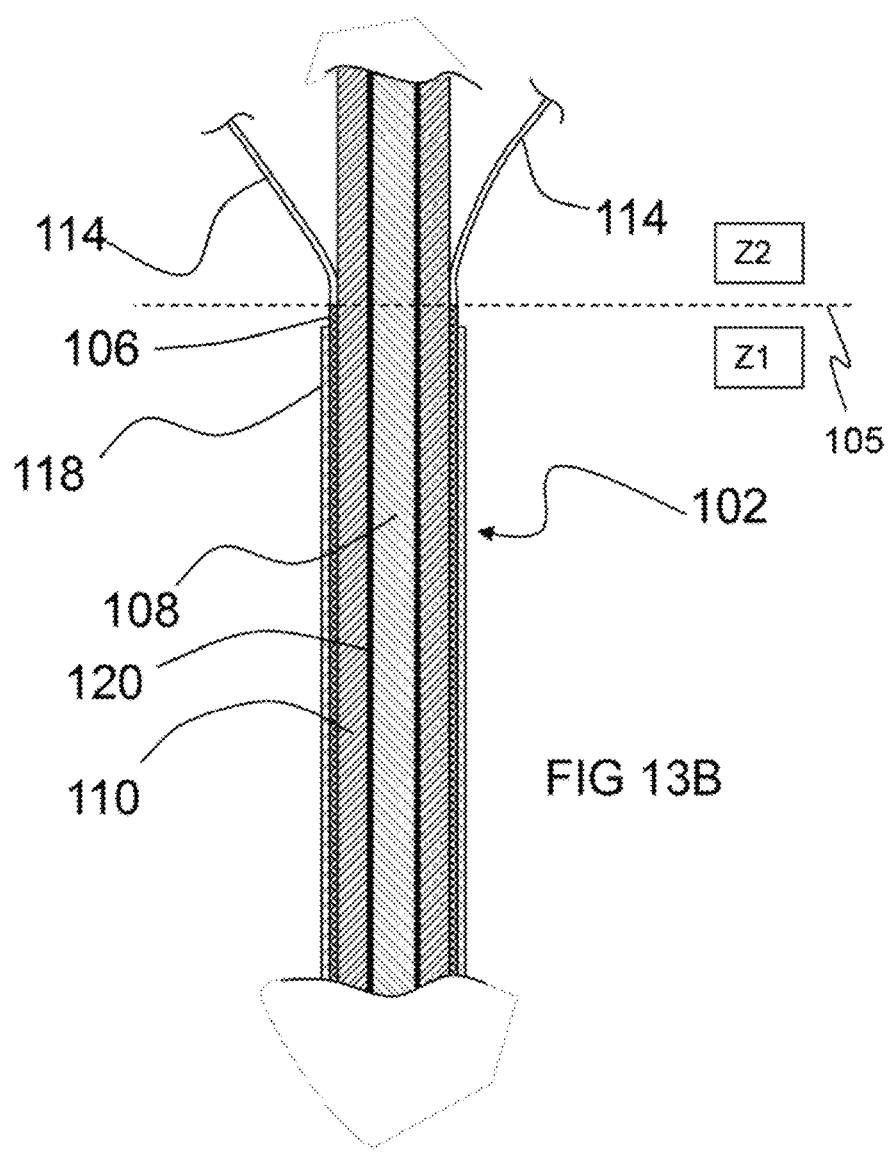

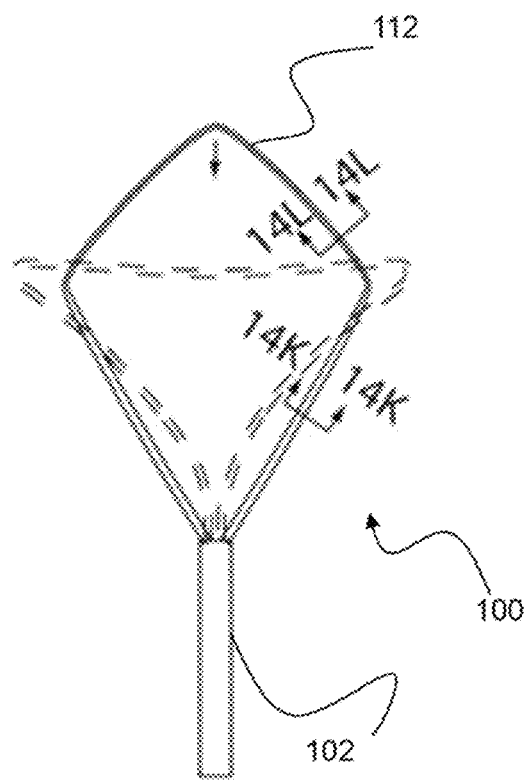
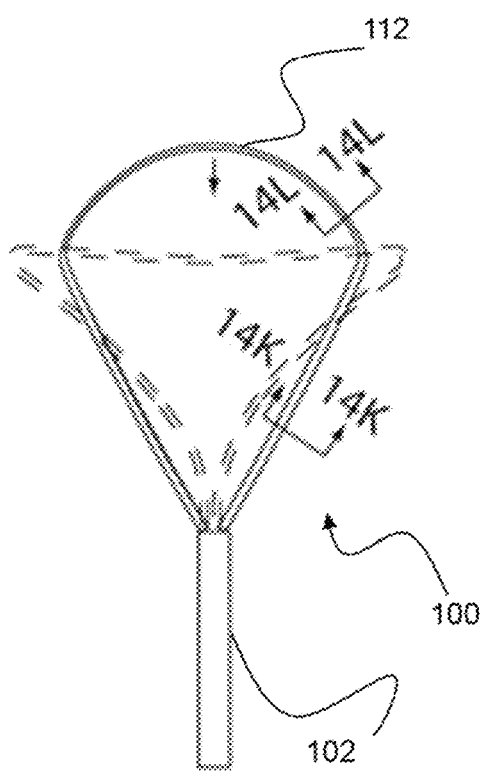
FIG 14I    FIG 14J
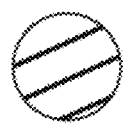
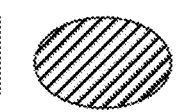
FIG 14K    FIG 14L

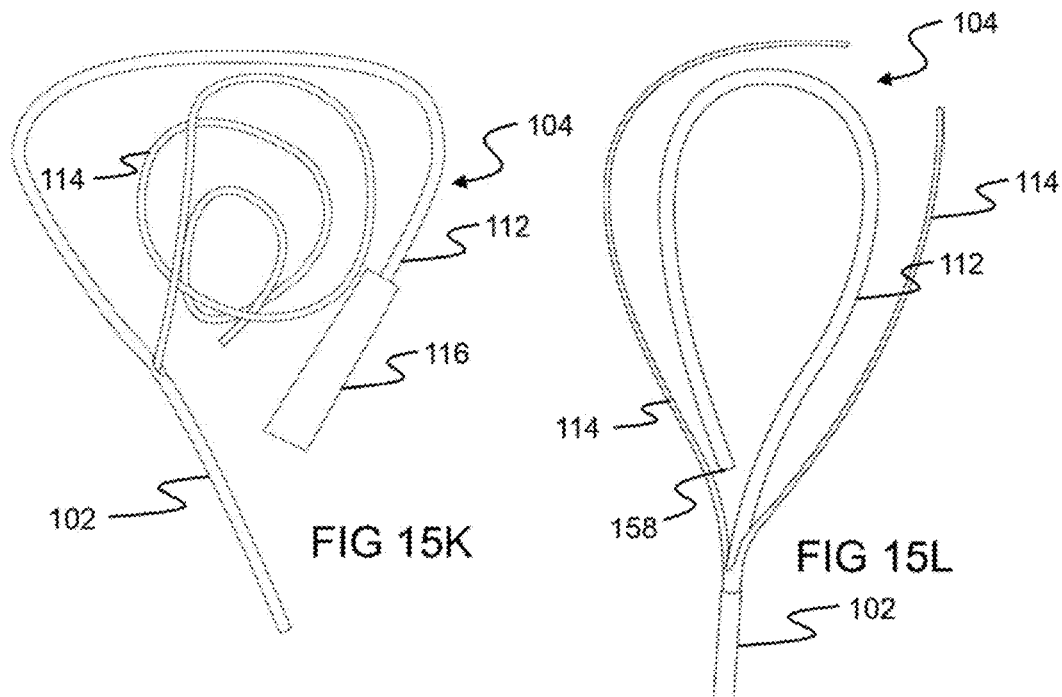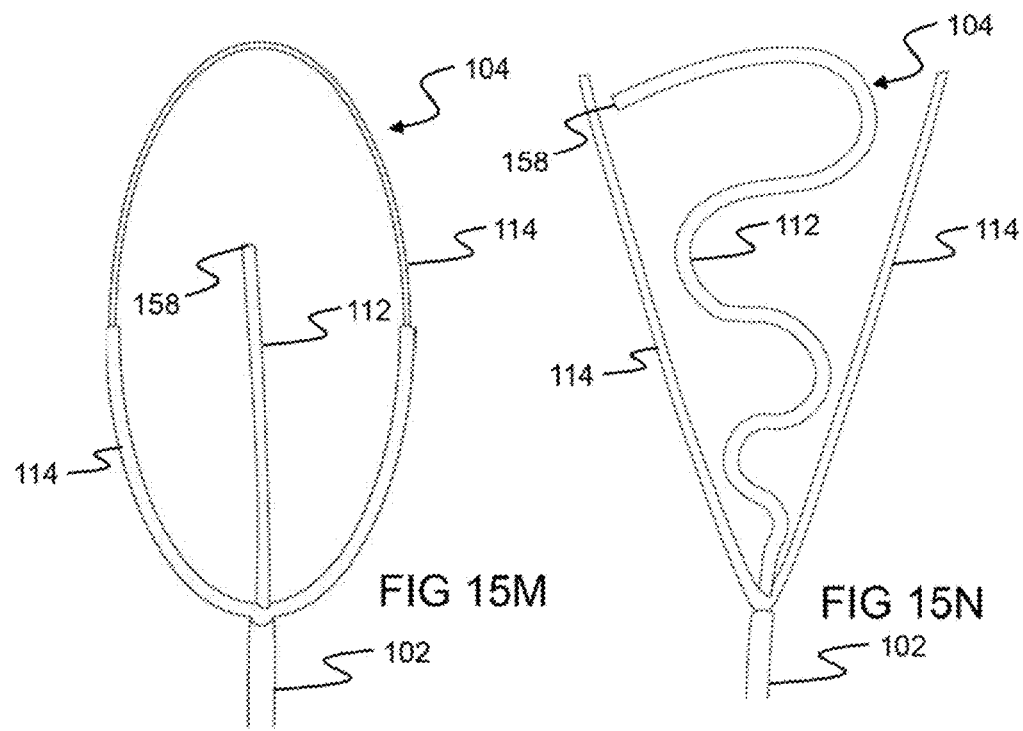

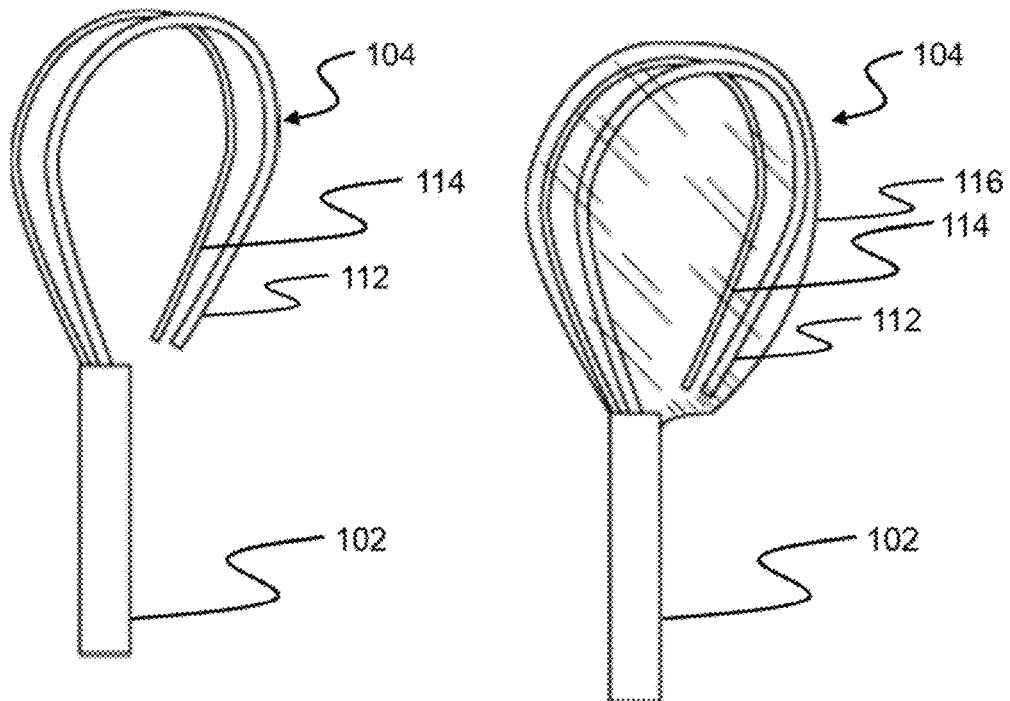
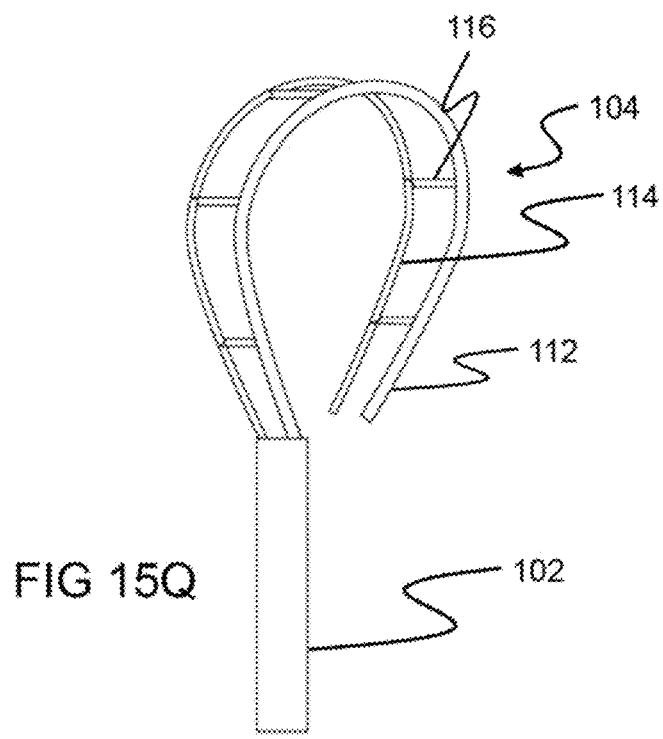

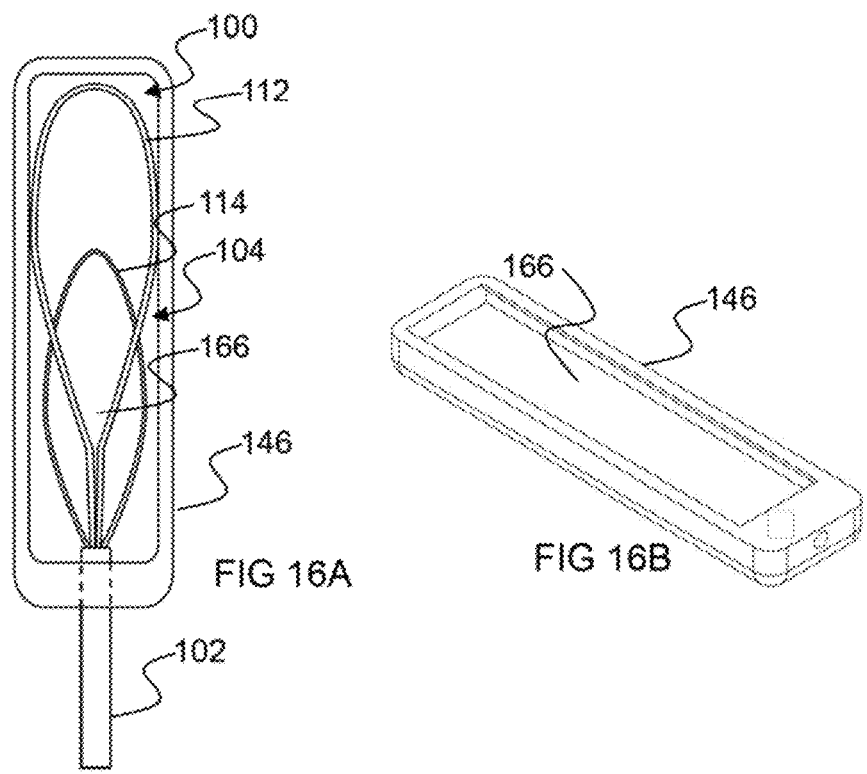
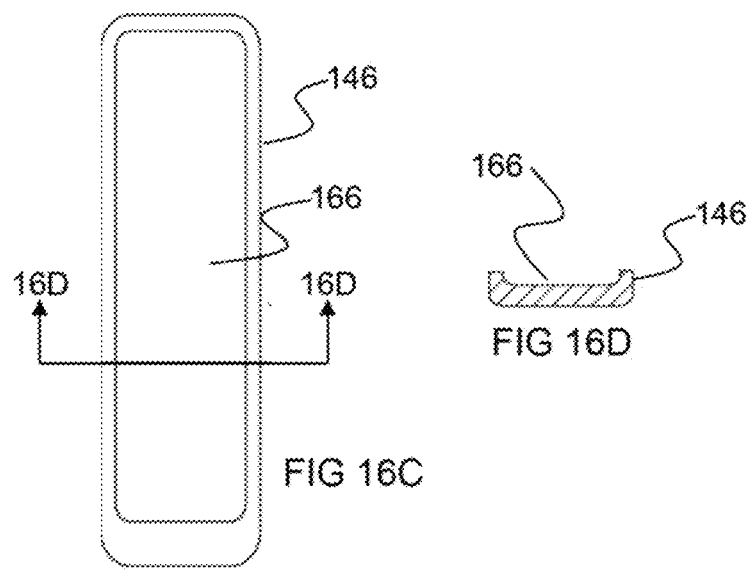

METHODS AND DEVICES FOR APPLYING ENERGY TO BODILY TISSUES

CROSS-REFERENCE TO RELATED APPLICATIONS

This application is a continuation of U.S. patent application Ser. No. 12/603,077 filed Oct. 21, 2009, now U.S. Pat. No. 8,968,287, which claims benefit to U.S. Provisional Application Nos. 61/107,252 filed on Oct. 21, 2008, 61/162,241 filed on Mar. 20, 2009, 61/180,133 filed on May 21, 2009, and 61/222,409 filed on Jul. 1, 2009, each of which is incorporated herein by reference in its entirety.

FIELD OF THE INVENTION

This invention relates to medical elements (e.g. microwave ablation antennas), usable for performing diagnostic and/or therapeutic procedures on or within a patient's body.

BACKGROUND OF THE INVENTION

There is a need for improved devices and methods to treat several medical conditions. Several conditions including atrial fibrillation, cancer, Menorrhagia, wrinkles, etc. may be treated by ablating tissue by applying an ablating energy. Even though devices and methods exist to treat these conditions by ablating tissue, there is still an unmet need for improved devices and methods.

For example, microwave antennas (e.g. helical antennas) have been used in medical applications including treatment of benign prostate hyperplasia, cancer treatment, etc. Many of the existing antennas have common disadvantages such as device shaft heating and non-uniform lesion profile along the length of the antenna. Thus there is a need for microwave antennas that are capable of generating uniquely shaped microwave fields that overcome these problems. Several prior art antennas also need cooling mechanisms and sophisticated temperature monitoring systems to achieve acceptable clinical results.

Menorrhagia is one of the most common gynecological conditions in pre-menopausal women. It is characterized by excessive menstrual blood loss. The condition severely affects the quality of life of the affected women since it may interfere with physical activity, work and sexual activity. Several techniques have been developed that aim to destroy the uterine endometrium to treat menorrhagia in a minimally invasive manner. Such endometrial ablation techniques can be performed by a variety of methods such as radiofrequency heating, circulating hot saline in the uterine cavity, microwave heating, cryodestruction, laser destruction, etc. Every current endometrial ablation technique has some fundamental limitations. For example, the Hydrothermablator™ device by Boston Scientific needs a hysteroscope which adds to the procedure cost and complexity. Further the device is thick and rigid. Because of that, the procedure requires significant anesthesia, usually in the form of conscious sedation or general anesthesia. The Novasure™ device is also thick and rigid. Thus a significant amount of cervical dilation is needed to introduce the device into the uterine cavity. Since cervical dilation is very painful, the procedure requires significant anesthesia, usually in the form of conscious sedation or general anesthesia. Also, the device is expensive (~$900). Thus, even though there are a variety of endometrial ablation devices, there is still a need for a small-size, flexible, low-cost, easy to use next-generation device in this large and growing market.

Several ablation modalities such as microwave ablation can be used to treat solid tumors (e.g. liver tumors) by heating up the tumor tissue. Devices that use microwave ablation for treating tumors are advantageous over devices that use other ablation modalities because of their potential to create larger, uniform volumetric lesions. In prior art microwave ablation devices, microwave energy is emitted by an antenna and transmitted to the tumor tissue. The efficacy of the ablation procedure depends significantly on the power efficiency and the SAR and thermal profile of the antenna. Most existing microwave ablation devices are derived from the simple monopole antenna and have a linear structure. Their SAR and thermal profile are substantially elliptical and they are approximately similar to the shape of a football as shown in FIG. 2E. It is difficult to use a single monopole antenna to ablate tumors that have a thickness or diameter of a few centimeters in a sufficiently short time. For many cancer-related applications, the targeted tumors have an excessive size (e.g. diameter of several centimeters) and a single monopole antenna is of limited use. One of the solutions proposed to increase the lesion size involves using multiple ablation devices simultaneously. This increases the complexity of the ablation system. The overall size and cost of the ablation device will also be increased due to more number of elements employed in the system. Also, this increases the invasiveness and complexity of the procedure.

Further, the SAR profile shown in FIG. 2F demonstrates that there is a significant amount of microwave field proximal to the distal end of the coaxial cable feeding the radiating element (monopole antenna). Thus the ablation will not be accurately contained in the region around the radiating element. A portion of the tissue surrounding the distal region of the coaxial cable will be ablated. This in turn carries a risk of damaging healthy tissue by the microwave energy. Thus there is a need for improved microwave ablation devices that are low profile and that can ablate a tissue volume without damaging adjacent healthy tissue.

Atrial fibrillation (AF) is a cardiac electrophysiological disorder found in millions of Americans. Various ablation systems, including catheters and surgical tools, are used to ablate cardiac tissue to treat atrial fibrillation. In catheter ablation procedures, several individual lesions are then created as part of a desired lesion pattern. In many existing procedures, only a single, small, point lesion is created at any given time. Multiple such point lesions are needed to achieve the desired clinical response in the patient. In such procedures, an electrophysiologist guides the ablation tip of an ablation catheter to a point on the left atrium and creates a first point ablation. Once the first point ablation is created, the electrophysiologist then guides the ablation tip to a new location on the left atrium and creates a second point ablation, typically in communication with the first point lesion. This process continues until the desired lesion pattern is created. The creation of such multiple, connecting point lesions is very time consuming and technically challenging. There are other limitations to point ablation systems. For example, during the translation of the ablation tip to a new location, the distal ablation tip may slip, or otherwise move across the target tissue in an undesired manner. The steps of translation of the ablation tip to a new location are further complicated by the motion of the left atrium because of the natural beating of the heart. Further, users of point ablation systems typically use costly support equipment to provide historic and current position information of the ablating portion with respect to anatomical cardiac structures and previously created lesions. The support equipment is extremely costly and requires additional personnel to operate, ultimately increasing procedure costs. Still another problem with point ablation devices having ablating tip portions is the risk of perforation. The forces applied to the ablation devices are transmitted by the relatively narrow ablation tip to the atrial wall. Thus the relatively narrow ablation tip exerts a significant amount of pressure on the atrial wall. This in turn may result in perforation of the atrial wall which in turn may lead to formation of a potentially fatal atrio-esophageal fistula. Thus, there is a need for improved ablation devices that simplify the procedure of catheter ablation for treating atrial fibrillation and have a low risk of complications.

In order to overcome the limitations of point ablation systems, devices comprising an array of multiple radiofrequency (RF) electrodes were developed. However, RF electrodes need excellent tissue contact throughout the length of the electrode(s). This is difficult to achieve using the prior art delivery systems leading to inconsistent contact between the RF electrode(s) and the target tissue. Such inconsistent electrode contact causes variability in the transmission of energy throughout the target length of ablated coagulated tissue. This inconsistency also produces undesirable gaps of viable tissue that promote propagation of wavelets that sustain atrial fibrillation, or produce atrial flutter, atrial tachycardia, or other arrhythmia substrate. Thus, there is a need for devices that create sufficiently deep lesions even without achieving perfect contact with the target tissue.

Thus, even though several methods and devices exist that treat clinical conditions by energy delivery, there are still unmet needs for improved methods and devices.

BRIEF SUMMARY OF THE INVENTION

Several medical applications of the invention for applying energy to target materials such as tissue are also disclosed herein. Energy may be applied to tissue to achieve a variety of clinically useful effects. Examples of such effects include, but are not limited to: 1. ablating tissue to kill or otherwise damage tissue, 2. causing heat-induced modification of tissue (e.g. heat shrinkage of collagen), 3. causing heat-induced modification of an artificially introduced material (e.g. heat induced polymerization of an injected monomer), 4. warming tissue to change the metabolic activity of tissue (e.g. warming tissue to increase the metabolism). 5. causing fat liquefaction e.g. to ease fat extraction during Microwave Assisted Lipoplasty, 6. causing controlled tissue death to debulk tissue for treating conditions such as Obstructive Sleep Apnea, BPH, etc. and 7. delivering energy to tissue to change the electrophysiological characteristics of that tissue.

The present invention discloses devices and methods for treating tissue with microwave energy. In several method embodiments, microwave energy is used for ablating tissue e.g. for treating atrial fibrillation by controlled ablation of left atrial tissue, etc.

The device and methods disclosed herein may be used with or without modifications to create one or more point, linear, area or volumetric lesions. The present invention discloses various embodiments of flexible, low-profile devices that can be inserted non-invasively or minimally invasively into or near the target tissue.

Some of the embodiments herein may be broadly described as microwave devices comprising a transmission line such as a coaxial cable and an antenna connected to the coaxial cable. The antenna comprises 1. a radiating element, 2. one or more shaping elements and 3. one or more antenna dielectrics covering one or more portions of the radiating element and/or the shaping element. In embodiments wherein transmission line is a coaxial cable, the radiating element may be a continuation of the inner conductor of the coaxial cable or may be an additional conductive element electrically connected to the inner conductor of the coaxial cable. The radiating element radiates a microwave field that is characteristic of its specific design. The radiated microwave field causes agitation of polarized molecules, such as water molecules, that are within target tissue. This agitation of polarized molecules generates frictional heat, which in turn raises the temperature of the target tissue. Further, the microwave field radiated by the radiating element may be shaped or otherwise redistributed by one or more shaping element(s) in the antenna. In one embodiment, the shaping element(s) are made of an electrically conductive material (e.g. one or more metallic objects of various sizes, shapes, orientations, etc.). In this embodiment, the shaping element(s) may be electrically connected to the outer conductor or shielding element of the transmission line (e.g. the outer conductor of a coaxial cable). In an alternate embodiment, the shaping element(s) are not in direct electrical conduction with the outer conductor or shielding element of the transmission line e.g. the outer conductor of a coaxial cable. The one or more antenna dielectrics may cover one or more portions of one or both of: radiating element and shaping element. The antenna dielectrics may be used for changing the propagation of the microwave field from one or both of: radiating element and shaping element to the surrounding. The antenna dielectrics may be used for changing the matching The one or more additional shaping elements in the antenna may be used to create a more uniform microwave field distributed over a larger region. The one or more shaping elements in the antenna may also be used to improve the power deposition by the antenna. One or both of radiating element and shaping element may be enclosed in an antenna dielectric material In several of the embodiments disclosed herein, a conductive element (e.g. a length of metallic wire) electrically connected to the outer conductor of a coaxial cable is used to shape the microwave field.

Several embodiments of radiating elements and shaping elements and combinations thereof are described herein. The shapes of the cross section of radiating element and shaping element may be designed to achieve the desired mechanical and microwave properties. Examples of such cross section shapes include, but are not limited to round, oval, rectangular, triangular, elliptical, square, etc. Various antennas may be designed using a combination of a radiating element disclosed herein and a shaping element disclosed herein. The shape of the microwave field emitted by such antennas can be purposely shaped by designing the antenna. For example, an antenna may be designed to generate a microwave field designed to create a deeper ablation in the center of a target organ and shallower ablation towards the periphery of the target organ.

Various embodiments of antenna 104 may be designed to generate a variety of shapes of SAR and/or the ablation profile. For example, antennas 104 may be designed to generate substantially square, triangular, pentagonal, rectangular, round or part round (e.g. half round, quarter round, etc.), spindle-shaped or oval SARs or ablation patterns.

The methods and devices disclosed herein e.g. (a linear antenna disclosed herein) may be navigated through the anatomy and placed at one or more positions within the target anatomy using one or more steerable or non-steerable devices. Any of the antennas disclosed herein may comprise one or more attachments or integral elements to enable the user to navigate the antenna through the anatomy. Examples of such attachments or elements include, but are not limited to: integral tethers or external pull wires to pull one or more regions of a device or to bend or deflect one or more regions of a device, internal pull wires adapted to bend or deflect one or more regions of a device, one or more elements adapted to be steered by a surgical magnetic navigation modality, etc.

The antennas disclosed herein may be deployed from an insertion configuration to a working configuration before being placed in the vicinity or inside of the target tissue. Alternately, the antennas may be deployed from an insertion configuration to a working configuration after being placed in the vicinity or inside of the target tissue. The deployment of the antennas disclosed herein may be done by one of several methods. The antennas herein may be navigated to the target tissue in a fully deployed configuration. In one embodiment, an antenna is navigated to the surface of an abdominal organ e.g. the liver in a fully deployed configuration through a laparotomy. In another embodiment, an antenna disclosed herein is deployed through an introducer in which the antenna is in a collapsed, low-profile configuration when inside the introducer and is deployed to a working configuration after the antenna exits the introducer. The antenna may be deployed after the antenna exits the introducer by one or more of: the elastic property of the antenna or its components, the super-elastic property of the antenna or its components, the shape memory property of the antenna or its components, use of a mechanical deployment mechanism for the antenna or its components, use of one or more anatomical regions to change the shape of one or more antenna portions, etc. One or more portions of the antennas herein may be malleable or plastically deformable. This allows the user to shape an antenna to ensure better contact with target tissue or better navigation through the anatomy.

The devices disclosed herein comprise antennas wherein the ablation profile generated by an antenna is tailored and optimized for a particular clinical application. For example, in the embodiments wherein a microwave antenna is used to ablate the entire cavity wall or an entire circumferential region of the cavity wall, the ablation profile may be designed to ablate substantially the entire cavity wall or an entire circumferential region of the cavity wall without the need for repositioning of the antenna. In such embodiments, the microwave field may circumferentially envelop the entire antenna. For example, in the embodiments wherein a microwave antenna is used to ablate a tissue volume, the ablation profile may be designed to ablate substantially the entire tissue volume without requiring repositioning of the antenna. In several device embodiments herein, microwave antennas are designed such that they ablate a substantially linear region of tissue. Several such linear lesions may be created to form a lesion pattern that achieves the desired clinical result.

The antennas disclosed herein may be conformable to acquire the shape of a portion of the target anatomy or otherwise be shaped by one or more portions of the target anatomy. For example, the antennas disclosed herein may be elastically flexible to conform to the shape of a small cavity or to the shape of an adjacent wall of the cavity into which the antenna is deployed. The antennas disclosed herein may be sized and shaped to approximate the size and shape of the target anatomy such as the uterine cavity.

Several embodiments of slim and flexible ablation devices are disclosed herein. This allows the user to introduce such ablation devices minimally invasively through small incisions or openings or even non-invasively through natural openings or passageways. Examples of minimally invasive introduction includes percutaneous introduction through the vasculature. Examples of non-invasive introduction includes introduction from the anus, mouth or nostrils into the gastro-intestinal tract, introduction from the vagina into the female reproductive system, introduction from the urethra into the urinary system, introduction from the ear, nostrils or mouth into the ENT system, etc. The devices and methods disclosed herein may be used to ablate diseased tissue or healthy tissue or unwanted tissue in organs or artificially created cavities. The devices disclosed herein may be introduced through laparoscopic, thoracoscopic, cystoscopic, hysteroscopic or other endoscopic openings or instrumentation into or near organs or bodily cavities. The methods disclosed herein may be performed under real-time monitoring e.g. by using one or more of: direct visual observation, hysteroscopy, cystoscopy, endoscopy, laparoscopy, ultrasound imaging, radiological imaging, etc.

Various additional features may be added to the devices disclosed herein to confer additional properties to the devices disclosed herein. Examples of such features include, but are not limited to one or more lumens, ability to apply a vacuum or suction to the target anatomy, ability to visualize one or more regions of the target anatomy, ability to limit the depth of insertion into the target anatomy, ability to deploy the antenna, ability to connect to a source of energy, etc.

Several of the method and device embodiments are designed to minimize the use of anesthesia such that the methods may potentially be performed using only local anesthesia.

The dimensions or other working parameters of the devices disclosed herein may be adjustable or programmable based on user inputs. The user input may be based on factors such as patient's anatomical data including anatomical dimensions and the desired level of safety and efficacy.

The various microwave antennas and the microwave engineering principles disclosed herein may be used in a variety of non-medical as well as medical applications. The near field of the microwave antennas disclosed herein may be used on target materials such as food, industrial products, semiconductors, etc. The near field of the microwave antennas disclosed herein may be used for cooking or heating foods, in industrial processes for drying and curing products, in semiconductor processing techniques to generate plasma for processes such as reactive ion etching and plasma-enhanced chemical vapor deposition (PECVD).

BRIEF DESCRIPTION OF THE SEVERAL VIEWS OF THE DRAWINGS

FIG. 1C shows a schematic view of an embodiment of a microwave ablation device of the present invention having a microwave antenna comprising a radiating element and a microwave field shaping element.

FIG. 1D shows a transverse section through an embodiment of the coaxial cable of the ablation device of FIG. 1C.

FIG. 1E shows a longitudinal section of the ablation device of FIG. 1C through the distal end of the coaxial cable.

FIGS. 2A and 2B show two side views of a simulated SAR profile generated by the device embodiment of FIG. 2A.

FIG. 13B shows a section of ablation device 100 of FIG. 13A through the distal end of coaxial cable 102.

FIGS. 14I and 14J show two alternate embodiments of shapes of microwave antennas of ablation devices.

FIG. 14K shows the substantially circular crossection of the microwave antenna of FIGS. 14I and 14J through plane 14K-14K.

FIG. 14L shows two alternate crossections of microwave antenna of FIGS. 14I and 14J through plane 14L-14L.

FIG. 14AA shows a view of the ablated tissue sliced through the plane 14AA-14AA in FIG. 14Y.

FIG. 15D-15N illustrate variations of devices having an antenna that comprises a single radiating element and one or more shaping elements.

FIGS. 15O-15Q show embodiments of antenna 104 comprising mechanisms to ensure proper deployment of antenna 104 in the anatomy.

FIGS. 16A-16D show various views of an embodiment of a shaping element that is usable for constraining an antenna to change or constrain the shape of the antenna.

DETAILED DESCRIPTION OF THE INVENTION

Figure 1A:
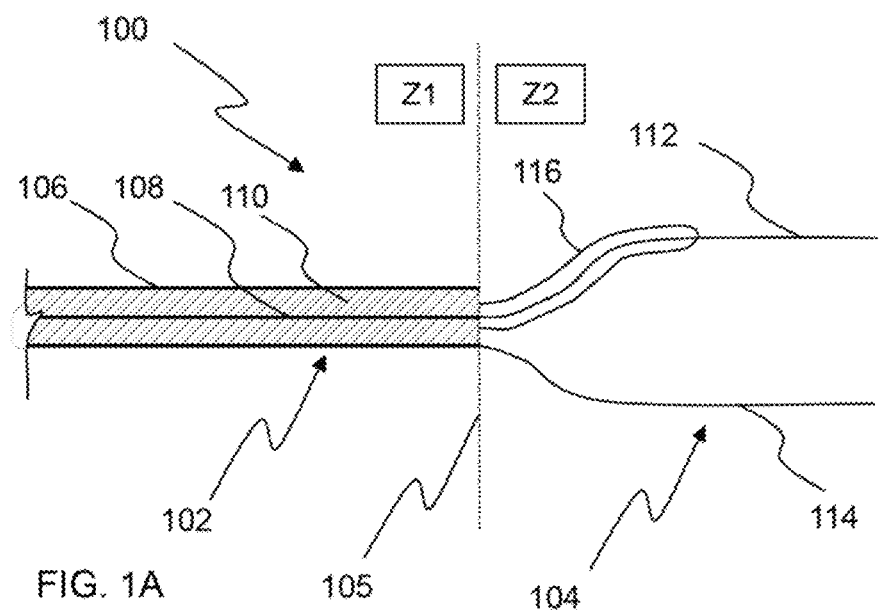
FIG. 1A shows a schematic view of an embodiment of a microwave ablation device of the present invention having a microwave antenna comprising a radiating element and a microwave field shaping element.

This specification discloses multiple antenna designs, systems, structures and devices, and associated methods, which illustrate various aspects of the invention. The various microwave antennas and the microwave engineering principles disclosed herein may be used in a variety of non-medical and medical applications. The near field of the microwave antennas disclosed herein may be used on target materials such as food, industrial products, semiconductors, etc. The near field of the microwave antennas disclosed herein may be used for cooking or heating foods, in industrial processes for drying and curing products, in semiconductor processing techniques to generate plasma for processes such as reactive ion etching and plasma-enhanced chemical vapor deposition (PECVD). While these systems, structures and devices, and associated methods, are discussed primarily in terms of some particular clinical applications (e.g. ablating cardiac tissue to treat arrhythmias, endometrial ablation), the methods and devices disclosed herein are applicable for use in other bodily structures, as well. These systems, structures and devices, and associated methods, may be used for ablating tissue in, or adjacent to, the brain, prostate gland, portions of the urinary tract, gall bladder, uterus and other portions of the female reproductive tract, regions of the vasculature, intestines and other portions of the lower alimentary tract, stomach and other portions of the upper alimentary tract, liver and other digestive organs, lungs, skin, mucus membranes, kidneys, reproductive organs, joints, or other organs or soft tissues of the body. The devices and methods disclosed herein may be used for the treatment of knee disorders, anterior cruciate ligament instability, vertebral disk injuries and chronic low back pain. The devices and methods disclosed herein may be used several arthroscopic applications such as shrinking the tissues of the ligamentous joint capsule to increase the tension on these ligaments for stabilizing the shoulder joint.

Several devices and methods disclosed herein may be used to treat tissue by microwave thermal ablation. Even though a significant portion of the disclosure is about microwave device and methods for ablation of tissue to kill or otherwise damage tissue, microwave energy may be applied to tissue to achieve a variety of clinically useful effects other than ablation. Examples of such effects include, but are not limited to: 1. causing heat-induced modification of tissue (e.g. heat shrinkage or other alteration in the properties of collagen), 2. causing heat-induced modification of an artificially introduced material (e.g. heat induced polymerization of an injected monomer), 3. warming tissue to change the metabolic activity of tissue (e.g. warming tissue to increase metabolism), 4. causing fat liquefaction e.g. to ease fat extraction during Microwave Assisted Lipoplasty, 5. causing controlled tissue death to debulk tissue for treating conditions such as Obstructive Sleep Apnea and 6. delivering energy to tissue to change the electrophysiological characteristics of that tissue. Even though several microwave emitting device embodiments herein are called ablation devices 100, such microwave emitting device embodiments may be used for methods that do not involve ablation of tissue.

Microwave thermal ablation does not depend on the conduction of electricity to tissue unlike RF ablation. Thus, devices using microwave thermal ablation such as the devices disclosed herein don't need good contact with tissue. They can function well even without perfect contact with the target tissue. Thus, the devices disclosed herein do not require extremely precise placement in tissue, thereby reducing the dependence of procedure outcome on physician skills. The devices herein are designed to have a distal microwave emitting portion comprising an antenna and a proximal shaft. The proximal shaft comprises a transmission line such as a flexible coaxial cable that delivers microwave energy from a microwave generator to the microwave emitting portion. The shaft can be designed to be slim (e.g. <3 mm in diameter) to enable the introduction of the ablation device through narrow openings. The shaft can be designed to be flexible such that minimal forces are exerted on bodily tissues during the introduction of the ablation devices into the anatomy. The flexible nature of the shaft enables the shaft to take the natural shape of passage during introduction instead of distorting the passage by the shaft of the device. For example, when a device is introduced trans-cervically into the uterus, the shaft may acquire the shape of introduction passage comprising the vagina, cervical canal and uterine cavity instead of distorting one or more of the vagina, cervical canal and uterine cavity. The designs of the coaxial cables disclosed herein confer sufficient flexibility to the device shaft such that the device shaft is capable of bending by more than 45 degrees when it experiences distorting forces by the anatomy. If desired, the device shaft may be made stiffer by adding one or more coatings, coverings, stylets and other stiffening elements.

Several of the experiments herein were performed at 0.915 GHz or 2.45 GHz ISM band. Antennas, methods, etc. disclosed herein may be used with or without modifications at other frequencies including, but not limited to ISM bands of 0.433 GHz, 5.8 GHz, etc. The microwave power generator may be magnetron based or solid state. The microwave power generator may be single or multi-channel. The microwave power generator used for the experiments comprised a Vector Network Analyzer (Agilent 8753 series) and amplifier modules build in-house using transistors from Freescale Semiconductor (Austin, Tex.). The power measurement was made using a power meter (ML2438A Power Meter, Anritsu Company, Richardson, Tex.). Similar devices and components can be used to design the microwave generator for clinical use with the devices and methods disclosed herein.

In the experiments, where desired, a fiber optic thermometry system (FOT Lab Kit by LumaSense Technologies, Santa Clara, Calif.) was used to measure the temperature at several locations in the tissue. The fiber optic thermometry system was used since it has no metallic components that might interfere with the microwave field. Similar non-interfering thermometry may be used to measure the temperature at one or more locations during an ablation procedure.

FIG. 1A shows a schematic view of an embodiment of a microwave ablation device of the present invention having a microwave antenna comprising a radiating element and a microwave field shaping element. In FIG. 1A, microwave ablation device 100 comprises a transmission line such as a coaxial cable 102. An antenna 104 is connected to the distal end of coaxial cable 102. FIG. 1A shows microwave ablation device 100 divided into a first zone Z1 and a second zone Z2 by an imaginary transition line 105. First zone Z1 is proximal to second zone Z2. Transition line 105 is defined by the distal end of coaxial cable 102 and is substantially perpendicular to the axis of coaxial cable 102 at the distal end of coaxial cable 102. In the embodiment shown in FIG. 1A, the distal region of coaxial cable 102 lies entirely within first zone Z1 and antenna 104 lies entirely within second zone Z2. In a one embodiment, a single microwave signal is fed to antenna 104 through coaxial cable 102. Antenna 104 generates a microwave field. The near field of the microwave field generated by antenna 104 may be used for tissue ablation.

In FIG. 1A, antenna 104 comprises a radiating element 112 and a shaping element 114. Radiating element 112 may be made of a variety of conducting materials e.g. metals, conductive polymers, materials with embedded conductive particles, etc. When microwave energy is delivered through coaxial cable 102 to antenna 104, a first microwave field is emitted by radiating element 112. The first microwave field interacts with shaping element 114. This interaction induces a leakage current on shaping element 114. The leakage current in turn creates a second microwave field. The first microwave field and the second microwave field together combine to produce a unique shaped microwave field of antenna 104 that is clinically more useful that the unshaped microwave field generated by an antenna 104 comprising only radiating element 112. Thus the original microwave field is redistributed by the design of shaping element 114. Shaping element 114 alone is not capable of functioning as an antenna; rather shaping element 114 shapes or redistributes the electromagnetic or microwave field emitted by radiating element 112 to produce a clinically improved microwave field. It should be noted that there is no direct electrical conduction between radiating element 112 and shaping element 114. Antenna 104 further comprises one or more antenna dielectrics 116 covering one or more portions of one or both of: radiating element 112 and shaping element 114. In FIG. 1A, an antenna dielectric 116 covers the proximal portion of radiating element 112. Any of the antenna dielectrics 116 disclosed herein may be used to shape the microwave field and to optimize the performance of antenna 104. Any of the antenna dielectrics 116 disclosed herein may be replaced by one or more conducting polymers.

A microwave field couples to the nearest conductive path. In prior art monopole antennas such as shown in FIG. 2E, the nearest conductive path is provided by the shielding element of the transmission line (e.g. the outer conductor 106 of the feeding coaxial cable 102). This causes a strong concentration of the microwave field in the junction between antenna 104 and transmission line 102. However, in several embodiments of antenna 104 disclosed herein, the nearest conductive path is provided by shaping element 114. Thus the microwave field couples to shaping element 114 instead of coupling to the shielding element of the transmission line (e.g. the outer conductor 106 of the feeding coaxial cable 102). Therefore, minimal microwave field is coupled proximally to the shielding element of the transmission line. This in turn creates a unique, shaped or redistributed microwave field that does not significantly extend proximally to antenna 104 as shown in FIGS. 2A, 2M, 6B, 6F and 14B. Further, the combination of radiating element 112 and shaping element 114 improves the power deposition of antenna 104.

Antennas disclosed herein may comprise one or more shaping elements 114 made of a variety of conducting materials e.g. metals, conductive polymers, materials with embedded conductive particles, etc. Such shaping elements 114 may comprise one or more dielectrics layers to insulate the shaping element 114 from surrounding tissue. Examples of such shaping elements 114 include, but are not limited to: straight or curved segments of metallic elements, elements with a circular or oval shape, elements with a polygonal shape (e.g. triangular, square, rectangular, pentagonal, etc.), multiple elements joined together by one or more electrically conducting joint(s), multiple elements joined together by a non-electrically conducting joint(s), elements with multiple curves, symmetrically arranged segments of elements, non-symmetrically arranged segments of elements, etc.

In the embodiment shown in FIG. 1A, the width of antenna 104 is substantially greater that the width of the coaxial cable 102. In one embodiment, radiating element 112 is a continuation of the inner conductor 108 of a coaxial cable 102. In a one embodiment, shaping element 114 is made of an electrically conductive material e.g. a metal and is electrically connected to a region of outer conductor 106 of coaxial cable 102. In an alternate embodiment, antenna 104 comprises one or more conductive shaping elements 114 that are electrically isolated from outer conductor 106. In this embodiment, one or more shaping elements 114 function as passive radiators or parasitic elements of antenna 104. In one embodiment, shaping element 114 is designed to act as a microwave shielding element and/or a microwave reflecting element.

Embodiments of antenna 104 may be designed wherein radiating element 112 has no sharp corners. Sharp corners in radiating element 112 may cause the field to concentrate in the vicinity of the sharp corners. Thus embodiments of the present invention may be designed that have minimal or no sharp corners to avoid undesirable regions of concentrated microwave field.

Antenna 104 may be designed to have a shape that substantially approximates the shape of the target tissue to be ablated. In one embodiment, antenna 104 has a roughly triangular shape that is especially suited for endometrial ablation. In another embodiment, antenna 104 has a roughly linear shape that is especially suited for the ablation of a linear region of tissue e.g. for the creation of a linear lesion in the left atrium.

Further, antenna 104 may be designed to be sufficiently flexible such that during and after introduction and deployment of antenna 104 in the anatomy, the anatomy experiences only slight forces from antenna 104. This may be achieved by designing an antenna 104 comprising one or more flexible radiating elements 112, one or more flexible shaping elements 114 and one or more flexible antenna dielectric materials. Sufficiently flexible antennas may reduce damage to healthy tissue as well as potentially reduce the pain experienced by the patient during the introduction and deployment. Antenna 104 may be introduced in a collapsed configuration through a small lumen. The collapsed configuration lowers the overall profile of antenna 104. In the collapsed configuration, radiating element 112 and shaping element 114 may be closer to each other than in the non-collapsed configuration. This enables the introduction of antenna 104 through narrow catheters, shafts, introducers and other introducing devices. Further, this enables the introduction of antenna 104 through small natural or artificially created openings in the body. Further, antenna 104 may be designed to have an atraumatic distal end in which the distal region of antenna 104 is wider and/or sufficiently flexible to reduce the risk of perforation of tissue. The flexible nature of antenna 104 enables antenna 104 to take the natural shape of an introduction passage during introduction instead of distorting the passage. For example, when antenna 104 is introduced via the vasculature into a heart chamber via a femoral vein access, flexible antenna 104 may be easily introduced through the introduction passage comprising the femoral vein access site, femoral vein and the inferior vena cava.

In one embodiment, the length of radiating element 112 measured along the radiating element 112 from the distal end of coaxial cable 102 or other transmission line until the distal end of radiating element 112 is an odd multiple of one quarter of the effective wavelength at one of: 433 MHz ISM band, 915 MHz ISM band, 2.45 GHz ISM band and 5.8 GHz ISM band. For example, the length of radiating element 112 may be three quarters of the effective wavelength at the 915 MHz ISM band. The effective wavelength is dependent on the medium surrounding the antenna and the design of a dielectric covering on the radiating element 112. The design of the dielectric covering includes features such as the type of dielectric(s) and thickness of the dielectric layer(s). The exact length of the radiating element 112 may be designed to get good impedance matching.

In any of the embodiments herein, the proximal portion of radiating element 112 may be a continuation of the inner conductor 108 of coaxial cable 102. The proximal portion of radiating element 112 in any of the embodiments herein may be designed to be stiffer and have a greater mechanical strength than the distal portion of radiating element 112. In one such embodiment, radiating element 112 is a continuation of inner conductor 108 of coaxial cable 102 and dielectric material 110 of coaxial cable 102 is retained on the proximal portion of radiating element 112. In another embodiment, the proximal portion of radiating element 112 is made stiffer by coating the proximal portion of radiating element 112 by a layer of dielectric.

In any of the embodiments herein, one or more outer surfaces of radiating element 112 may be covered with one or more layers of antenna dielectrics 116. The thickness and type of antenna dielectrics 116 along the length of radiating element 112 may be designed to modify and optimize the microwave properties of the antenna 104. For example, one or more antenna dielectrics 116 covering radiating element 112 may be used to shape the microwave field and to optimize the performance of antenna 104. The one or more antenna dielectrics 116 covering radiating element 112 may be used to shape the microwave field by changing the local dielectric environment in the region adjacent to radiating element 112. In any of the embodiments herein, every portion of radiating element 112 may be covered with some antenna dielectric 116 such that no metallic surface of radiating element 112 is exposed to tissue. Thus, radiating element 112 may be electrically insulated from tissue. Thus, in such embodiments, radiating element 112 is able to transmit a microwave field into tissue, but unable to conduct electricity to tissue. Thus, in such embodiments, there is no electrical conduction and no conductive path between radiating element 112 and shaping element 114. Further, in such embodiments, there is no electrical conduction and no conductive path between radiating element 112 and the surrounding tissue. Examples of dielectric materials that can be used to design one or more embodiments disclosed herein include, but are not limited to EPTFE, PTFE, FEP and other floropolymers, Silicone, Air, PEEK, polyimides, cyanoacrylates, epoxies, conducnatural or artificial rubbers and combinations thereof. In one embodiment, the dielectric on a proximal portion of radiating element 112 is a continuation of the dielectric 110 of coaxial cable 102. The thickness of a dielectric on radiating element 112 may vary along the length of radiating element 112. Further, the crossection of a dielectric on radiating element 112 may not be radially symmetric. The various configurations of the dielectric may be designed to achieve a desired ablation profile as well as achieve a desired impedance matching or power efficiency. In one embodiment, entire radiating element 112 is covered with a silicone dielectric. The layer of silicone used to coat a distal portion of radiating element 112 may be thinner than the layer of silicone used to coat a proximal portion of radiating element 112. The thinner silicone dielectric may be used to compensate for the lower field strength that normally exists at the distal portion of a microwave antenna. Thus, the microwave field is made more uniform along the length of radiating element 112. In one device embodiment with a silicone dielectric around radiating element 112, radiating element 112 is made of a metallic material and the circumference of the metallic material of a distal region of radiating element 112 is more than the circumference of the metallic material of a proximal portion of radiating element 112. This causes the silicone dielectric to stretch more at the distal portion than at the proximal portion of radiating element 112. This in turn generates a thinner layer of dielectric at the distal portion of radiating element 112 than at the proximal portion of radiating element 112. In another embodiment, entire radiating element 112 is made from a single length of metallic wire of a uniform crossection. In this embodiment, a tubular piece of silicone dielectric of varying thickness may be used to cover radiating element 112. The tubular silicone dielectric is used to cover radiating element 112 such that the layer of silicone dielectric is thinner around a distal portion and thicker around a proximal portion of radiating element 112.

In any of the embodiments herein, the shape of radiating element 112 may be that same or different from the shape of shaping element 114. Further in any of the embodiments herein, both radiating element 112 and shaping element 114 may be non-linear. Further, in any of the embodiments herein, radiating element 112 and shaping element 114 may be non-parallel to each other.

Figure 1B:
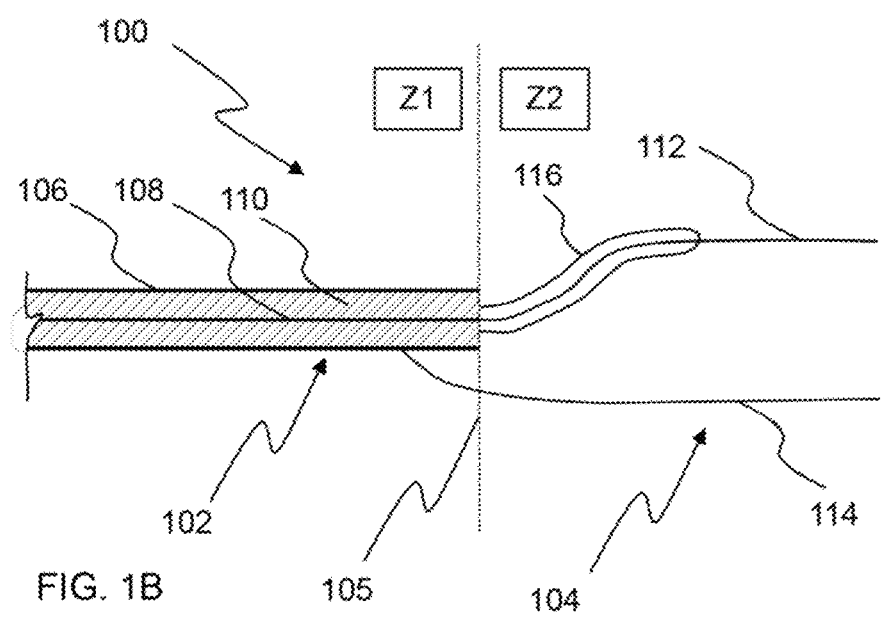
FIG. 1B shows a schematic view of an embodiment of a microwave ablation device similar to the embodiment in FIG. 1A wherein a microwave field shaping element is connected to a region of the transmission line proximal to the distal end of the transmission line.

FIG. 1B shows a schematic view of an embodiment of a microwave ablation device similar to the embodiment in FIG. 1A wherein a microwave field shaping element is connected to a region of the transmission line proximal to the distal end of the transmission line. This embodiment differs from the embodiment in FIG. 1A since in FIG. 1A, shaping element 114 is connected to the distal end of the transmission line. In one embodiment of the device shown in FIG. 1B, shaping element 114 is metallic and is electrically connected to a region of outer conductor 106 of coaxial cable 102.

In FIGS. 1A and 1B, since radiating element 112 is in electrical contact with inner conductor 108, there is a first electrically conductive path extending from inner conductor 108 till the distal end of radiating element 112. In the embodiments wherein shaping element 114 is made of a conductive material and is electrically connected to outer conductor 106 of coaxial cable 102 or other transmission line, there is a second electrically conductive path extending from outer conductor 106 till the distal end of shaping element 114. In such embodiments, even though there are two conductive paths that extend from first zone Z1 to the second zone Z2, the designs, materials and the microwave properties of the two conductive paths may be significantly different in first zone Z1 and second zone Z2. For example, the region of the first conductive path in first zone Z1 is surrounded by the dielectric 110 of coaxial cable 102 whereas the region of the first conductive path in second zone Z2 may be surrounded by one or more dielectric materials or by an anatomical region such as the target tissue. Further, in FIGS. 1A and 1B, the microwave field in first zone Z1 is substantially confined between inner conductor 108 and outer conductor 106 of coaxial cable 102. However, in second zone Z2, the microwave field is non-confined between radiating element 112 and shaping element 114. Further, in first zone Z1, outer conductor 106 of coaxial cable 102 is located symmetrically around inner conductor 108 and at a substantially constant distance from inner conductor 108. However, in second zone Z2, radiating element 112 and shaping element 114 are not located symmetrically relative to each other and the distance between radiating element 112 and shaping element 114 may or may not be constant throughout second zone Z2. Further, outer conductor 106 of coaxial cable 102 is oriented parallel to inner conductor 108 in first zone Z1. But in second zone Z2, radiating element 112 and shaping element 114 may or may not be parallel to each other. However, radiating element 112 and shaping element 114 may both have planar shapes. In one such embodiment, a plane containing radiating element 112 is substantially parallel to a plane containing shaping element 114. In first zone Z1, outer conductor 106 of coaxial cable 102 always acts as a shield for the microwave field in first zone Z1 whereas in second zone Z2, shaping element 114 may or may not act as a shield for the microwave field in second zone Z2. In first zone Z1, the distance between outer conductor 106 and inner conductor 108 may be substantially less than a distance between radiating element 112 and shaping element 114 in second zone Z2.

FIG. 1C shows a side view of an embodiment of a linear microwave antenna of the present invention having a microwave antenna comprising a radiating element and a microwave field shaping element. In the embodiment shown in FIG. 1C, the novel microwave field shaping technique of the present invention is used to improve the performance of a helical antenna. The resultant antenna can be used to create a uniform lesion along the length of the antenna without adversely affecting tissues surrounding the transmission line. In FIG. 1C, microwave ablation device 100 comprises a transmission line such as a coaxial cable 102. An antenna 104 is connected to the distal end of coaxial cable 102. In the embodiment shown in FIG. 1C, the width of antenna 104 is substantially the same as the width of the coaxial cable 102. FIG. 1C shows microwave ablation device 100 divided into a first zone Z1 and a second zone Z2 by an imaginary transition line 105. First zone Z1 is proximal to second zone Z2. Transition line 105 in FIG. 1C is defined by the distal end of coaxial cable 102 and is substantially perpendicular to the axis of coaxial cable 102 at the distal end of coaxial cable 102. In the embodiment shown in FIG. 1C, the distal region of coaxial cable 102 lies entirely within first zone Z1 and antenna 104 lies entirely within second zone Z2. In one embodiment, a single microwave signal is fed to antenna 104 through coaxial cable 102. Antenna 104 generates a microwave field. The near field of the microwave field generated by antenna 104 may be used for achieving the desired clinical outcome such as ablating tissue. In FIG. 1C, antenna 104 comprises a radiating element 112 and a shaping element 114. In one embodiment, radiating element 112 is a continuation of the inner conductor 108 of coaxial cable 102. Shaping element 114 shapes the microwave field emitted by radiating element 112. In one embodiment, shaping element 114 is made of an electrically conductive material e.g. a metal or a conductive polymer and is electrically connected to a region of outer conductor 106 of coaxial cable 102. In an alternate embodiment, a conductive shaping element 114 is electrically isolated from outer conductor 106. In this embodiment, shaping element 114 functions as a passive radiator or parasitic element of antenna 104. Shaping element 114 in this electrically isolated embodiment absorbs microwaves radiated from radiating element 112 and re-radiates microwaves. It should be noted that there is no direct electrical conduction between radiating element 112 and shaping element 114. When microwave energy is delivered through coaxial cable 102 to antenna 104 in FIG. 1C, a first microwave field is emitted by radiating element 112. This first microwave field is a normal mode microwave field of a small diameter (antenna diameter D is much less than microwave wavelength) helical antenna. The first microwave field interacts with shaping element 114. This interaction induces a leakage current on shaping element 114. The leakage current in turn creates a second microwave field. The second microwave field is an elongated, axial mode microwave field due to the elongate shape of shaping element 114. The first microwave field and the second microwave field together combine to produce a unique shaped microwave field of antenna 104 that is clinically more useful that the unshaped microwave field generated by an antenna 104 comprising only radiating element 112. Thus the original microwave field is redistributed by the design of shaping element 114. Shaping element 114 alone is not capable of functioning as an antenna; rather shaping element 114 shapes or redistributes the electromagnetic or microwave field emitted by radiating element 112 to produce a clinically improved microwave field. It should be noted that there is no direct electrical conduction between radiating element 112 and shaping element 114 in FIG. 1C.

Further, the specific design of shaping element 114 may be used to improve the power deposition of an antenna 104 comprising radiating element 112. Shaping element 114 may be made of one or more non-insulated or insulated elements. Examples of such elements include, but are not limited to: straight or curved segments of metallic elements, elements with a circular or oval shape, elements with a polygonal shape (e.g. triangular, square, rectangular, pentagonal, etc.), multiple elements joined together by an electrically conducting joint(s), multiple elements joined together by a non-electrically conducting joint(s), elements with multiple curves, symmetrically arranged segments of elements, non-symmetrically arranged segments of elements, elements comprising outer coatings or layers of non-conducting materials, etc.

The embodiments of the present invention may be designed wherein individual elements e.g. radiating element 112 have minimal or no sharp corners to avoid undesirable regions of concentrated microwave field.

Antenna 104 may be designed to have a shape that substantially approximates the shape of a target tissue to be ablated or the shape of a lesion to be created. In one embodiment, antenna 104 has a roughly triangular shape that is especially suited for endometrial ablation. In another embodiment, antenna 104 has a roughly linear shape such as that shown in FIG. 1C that is especially suited for the ablation of a linear region of tissue e.g. for the creation of a linear lesion in the left atrium.

In FIG. 1C, the surface of radiating element 112 is enclosed within one or more layers of dielectric materials. The thickness and type of dielectric material along the length of radiating element 112 is engineered to optimize the microwave field shape. Thus one or more dielectric materials covering radiating element 112 may also be used as non-conducting shaping elements to shape the microwave field. The one or more dielectric materials covering radiating element 112 shape the microwave field by changing the local dielectric environment in the region adjacent to radiating element 112. In this embodiment, every portion of radiating element 112 is covered with some dielectric material such that no metallic surface of radiating element 112 is exposed to tissue. Thus, in this embodiment, radiating element 112 is electrically insulated from tissue. Thus, in this embodiment, radiating element 112 is able to transmit a microwave field into tissue, but unable to conduct electricity to tissue. Thus, in this embodiment, there is no electrical conduction and no conductive path between radiating element 112 and shaping element 114. Further, in this embodiment, there is no electrical conduction and no conductive path between radiating element 112 and the surrounding tissue. In one embodiment, the dielectric on a proximal portion of radiating element 112 is a continuation of the dielectric 110 of coaxial cable 102. The thickness of a dielectric on radiating element 112 may vary along the length of radiating element 112. Further, the crossection of a dielectric on radiating element 112 may not be radially symmetric.

Figure 7A:
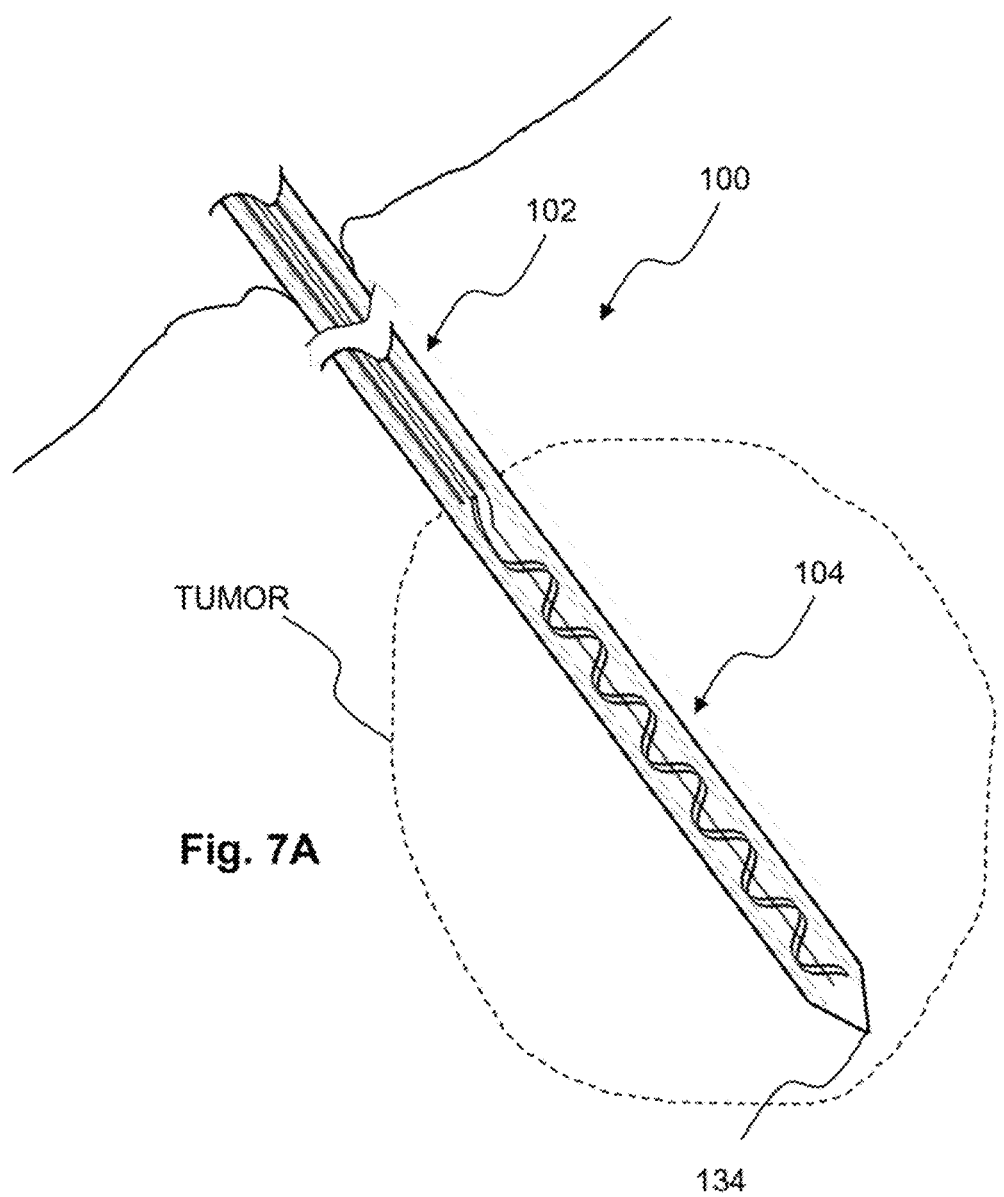
FIG. 7A shows an embodiment of a substantially linear antenna used to penetrate a bodily tissue and ablate a tumor.

In the embodiment of FIG. 1C, radiating element 112 is made of a helically arranged length of a metallic conductor. The helix may be symmetric with a constant pitch and a constant diameter along the length of the helix. In one embodiment, the straightened length of the conductor used for constructing radiating element 112 is about three quarters of the effective wavelength at 915 MHz. In alternate embodiments, this length may be an odd multiple of one quarter of the effective wavelength at one of: 433 MHz ISM band, 915 MHz ISM band, 2.45 GHz ISM band and 5.8 GHz ISM band. Although in FIG. 1C, radiating element 112 has about 19 turns, embodiments of ablation devices 100 may be constructed wherein radiating element 112 has about 1 to 30 turns. The pitch of a helical radiating element 112 may range between 0.3 mm and 20 mm. Radiating element 112 may be made from a metallic element or alloy selected from the group comprising Nitinol, stainless steel or copper. Radiating element 112 may comprise a plating of a conducting metal such as Ag or Au on the outer surface of radiating element 112. The metallic conductor used for constructing radiating element 112 may have a round, oval, rectangular or square crossection. In one embodiment, the metallic conductor used for constructing radiating element 112 has a round crossection with a diameter of 0.5 mm+/−0.4 mm. In another embodiment, the metallic conductor used for constructing radiating element 112 has a rectangular crossection with crossectional dimensions of 10 mm+/−9.5 mm by 0.5 mm+/−0.4 mm. In another embodiment of a radiating element with a rectangular crossection, the crossectional dimensions are 1 mm+/−0.3 mm by 0.1 mm+/−0.05 mm. In an alternate embodiment, radiating element 112 is made of a length of a metallic conductor that is arranged in a substantially two dimensional configuration. For example, the length of a metallic conductor may be arranged in a substantially wavy or zigzag or serpentine configuration. In the embodiment in FIG. 1C, radiating element 112 is arranged symmetrically around shaping element 114 and partially or fully encloses shaping element 114. Shaping element 114 may be made of a linear or helical length of a metallic conductor. The outer diameter of shaping element 114 may be uniform or may be non-uniform along the length of antenna 104. In the embodiment shown in FIG. 1C, shaping element 114 is made of a substantially linear length of a metallic conductor. Shaping element 114 may be made from a metallic element or alloy selected from the group comprising Nitinol, stainless steel or copper. Shaping element 114 may comprise a plating of a conducting metal such as Ag or Au on the outer surface of shaping element 114. The metallic conductor used for constructing shaping element 114 may have a round, oval, rectangular or square crossection. In one embodiment, the metallic conductor used for constructing shaping element 114 has a round crossection with a diameter of 0.5 mm+/−0.3 mm. In another embodiment, the metallic conductor used for constructing shaping element 114 has a rectangular crossection with dimensions of 0.5 mm+/−0.3 mm by 0.5 mm+/−0.3 mm. Antenna 104 further comprises one or more antenna dielectrics 116 between radiating element 112 and shaping element 114. In one embodiment, antenna dielectric 116 is sufficiently flexible to create a flexible antenna 104. The flexibility of antenna 104 allows antenna 104 to bend from a substantially linear configuration to a substantially non-linear configuration and vice-versa during clinical use. The flexibility of antenna 104 also allows antenna 104 to bend relative to the distal end of the transmission line during clinical use. This in turn allows a user to introduce antenna 104 to the target location through tortuous or non-linear introduction paths such as blood vessels. In one embodiment, antenna dielectric 116 is sufficiently stiff to create a sufficiently stiff antenna 104. The stiffness of antenna 104 prevents antenna 104 from bending during clinical use. This in turn enables the user to use antenna 104 to puncture or penetrate through tissue such as tumor tissue as shown in FIG. 7A. Examples of dielectrics that can be used between radiating element 112 and shaping element 114 include, but are not limited to EPTFE, PTFE, FEP and other floropolymers, Silicone, Air, PEEK, polyimides, natural or artificial rubbers and combinations thereof. Additionally the entire antenna 104 may be covered or encapsulated in a dielectric. Examples of dielectrics that can be used to cover or encapsulate antenna 104 include, but are not limited to EPTFE, PTFE, FEP and other floropolymers, Silicone, PEEK, polyimides, natural or artificial rubbers and combinations thereof. Antenna dielectric 116 may comprise one or more layers of such dielectrics. The dielectric used to cover or encapsulate antenna 104 may be porous or non-porous. In FIG. 1C, the length of antenna 104 is between 10 mm and 80 mm. In FIG. 1C, the width of antenna 104 is between 1 mm and 40 mm. In one particular embodiment, antenna 104 has a length of 45 mm+/−7 mm and a width of 2 mm+/−0.5 mm. Radiating element 112 is electrically connected to inner conductor 108 of coaxial cable 102. This may be done for example, by soldering or resistance welding radiating element 112 to inner conductor 108. Shaping element 114 is electrically connected to outer conductor 106 of coaxial cable 102. This may be done for example, by soldering or resistance welding shaping element 114 to outer conductor 106. Antenna 104 may be floppy, flexible or substantially rigid. Antenna 104 may be malleable or have shape memory or elastic or super-elastic properties. The distal end of antenna 104 may be atraumatic. Antenna 104 may be designed such that the length of antenna 104 is adjustable. For example, length of antenna 104 may be increased or reduced to increase or reduce the length of an ablation zone. In this embodiment, shaping element 114 may have a helical or substantially wavy or zigzag or serpentine configuration. The length of antenna 104 may be increased or reduced intra-operatively or pre-operatively. In one embodiment, one or both of radiating element 112 and shaping element 114 are a part of a flexible circuit and are manufactured using commonly known techniques for manufacturing flexible circuits.

In FIG. 1C, the shape of radiating element 112 is different from the shape of shaping element 114. Further in the embodiment in FIG. 1C, radiating element 112 is non-linear. Further in the embodiment in FIG. 1C, shaping element 114 is substantially linear. However radiating element 112 and shaping element 114 are generally oriented such that their axes are parallel to each other. Alternate embodiments of antenna 104 may be designed wherein radiating element 112 is substantially linear. Alternate embodiments of antenna 104 may be designed wherein shaping element 114 is substantially non-linear. Alternate embodiments of antenna 104 may be designed wherein radiating element 112 and shaping element 114 are generally oriented such that their axes are not parallel.

Although in the embodiment in FIG. 1C shaping element 114 is connected to the distal end of coaxial cable 102, other embodiments of antenna 104 may be designed wherein shaping element 114 is connected to coaxial cable 102 at a region other than the distal end of coaxial cable 102. For example, in one alternate embodiment, shaping element 114 is metallic and is electrically connected to a region of outer conductor 106 of coaxial cable 102 proximal to the distal end of the coaxial cable 102.

In FIG. 1C, since radiating element 112 is in electrical contact with inner conductor 108, there is a first electrically conductive path extending from inner conductor 108 till the distal end of radiating element 112. In the embodiments wherein shaping element 114 is made of a conductive material and is electrically connected to outer conductor 106 of coaxial cable 102, there is a second electrically conductive path extending from outer conductor 106 till the distal end of shaping element 114. In such embodiments, even though there are two conductive paths that extend from first zone Z1 to the second zone Z2, the designs, materials and the microwave properties of the two conductive paths may be significantly different in first zone Z1 and second zone Z2 as described before. In first zone Z1, outer conductor 106 of coaxial cable 102 is located symmetrically around inner conductor 108 and at a constant distance from inner conductor 108. However, in second zone Z2, radiating element 112 is located symmetrically around shaping element 114 and at a constant distance from shaping element 114. In first zone Z1, outer conductor 106 of coaxial cable 102 always acts as a shield for the microwave field in first zone Z1 whereas in second zone Z2, shaping element 114 may or may not act as a shield for the microwave field in second zone Z2.

FIG. 1D shows a section through an embodiment of coaxial cable 102 usable for ablation device 100 of FIG. 1C and for other ablation devices 100 disclosed herein. In one embodiment, coaxial cable 102 used herein is flexible and comprises an inner conductor 108 made of Nitinol with a Ni content of 56%+/−5%. The outer diameter of inner conductor 108 is 0.0172"+/−0.004". Inner conductor 108 has a cladding or plating 120 of a highly conductive metal such as Ag or Au. In one embodiment, inner conductor 108 comprises a silver cladding 120 of thickness 0.000250"+/−0.000050". Cladding 120 in turn is surrounded by dielectric material 110. In one embodiment, dielectric material 110 is made of expanded PTFE with an outer diameter of 0.046"+/−0.005". The dielectric material 110 in turn is surrounded by the outer conductor 106. Outer conductor 106 acts as a shielding element to the microwave signals transmitted by inner conductor 108. Further, outer conductor 106 shields the microwave signals transmitted by inner conductor 108 from external noise. In one embodiment, outer conductor 106 comprises multiple strands of Ag plated Cu. The multiple strands of outer conductor 106 are arranged such that the outer diameter of outer conductor 106 is 0.057"+/−0.005". Outer conductor 106 in turn is covered by an outer jacket 118. In one embodiment, outer jacket 118 is made of PTFE with an outer diameter of 0.065"+/−0.005". Thus, the outer diameter of coaxial cable 102 is less than about 2 mm. The low profile of flexible coaxial cable 102 has tremendous clinical advantages since it can be inserted through narrow and/or tortuous anatomical paths or introducing device lumens. In one embodiment, a shaft comprising coaxial cable 102 is stiffened or strengthened by adding one or more stiffening or strengthening elements such as enclosing stiffening devices jackets, braids, or stiffening layers over coaxial cable 102. In one embodiment, antenna 104 is stiffened or strengthened by adding one or more stiffening or strengthening elements such as jackets, braids or layers within or over antenna 104.

FIG. 1E shows a longitudinal section of the embodiment of ablation device 100 of FIG. 1C through the distal end of coaxial cable 102. In FIG. 1E, the identity of coaxial cable 102 ends at the distal end of outer conductor 106. Transition line 105 in FIG. 1E is located at the distal end of outer conductor 106 and is substantially perpendicular to the axis of coaxial cable 102 at the distal end of outer conductor 106. Outer jacket 118 of coaxial cable 102 terminates a small distance proximal to the distal end of outer conductor 106. A conductive element attached to the distal end of inner conductor 108 forms radiating element 112. In one embodiment, the proximal end of radiating element 112 is electrically connected to the distal end of inner conductor 108. In one embodiment, the proximal end of radiating element 112 is soldered to inner conductor 108. In another embodiment, the proximal end of radiating element 112 is laser welded to inner conductor 108. The proximal end of radiating element 112 may be electrically connected to inner conductor 108 in various configurations including, but not limited to lap joint and butt joint. The proximal end of shaping element 114 is electrically connected to a region of outer conductor 106. In one embodiment, the proximal end of shaping element 114 is electrically connected to the distal end of outer conductor 106. In one embodiment, the proximal end of shaping element 114 is soldered to outer conductor 106. In another embodiment, the proximal end of shaping element 114 is laser welded to outer conductor 106. The proximal end of shaping element 114 may be electrically connected to outer conductor 106 in various configurations including, but not limited to lap joint and butt joint.

Figure 2C:
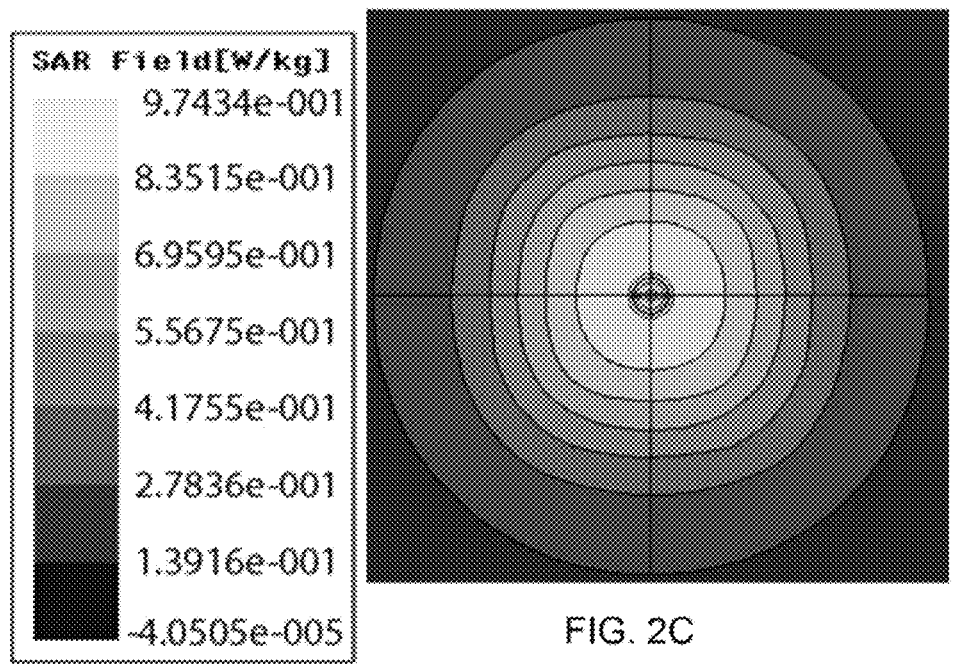
FIG. 2C shows a top view of a simulated SAR profile generated by the device embodiment of FIG. 2A.

FIGS. 2A and 2B show two side views of a simulated SAR profile generated by the device embodiment of FIG. 1C. FIG. 2C shows a top view of a simulated SAR profile generated by the device embodiment of FIG. 1C. FIG. 2C demonstrates that the SAR profile generated by the device embodiment of FIG. 1C is substantially radially symmetric and circumferentially envelops entire antenna 104. FIGS. 2A and 2B demonstrate that the microwave field generated by antenna 104 of FIG. 1C is substantially restricted to second zone Z2. There is an insignificant amount of the microwave field in first zone Z1 containing coaxial cable 102. Thus, there is negligible backward coupling between the microwave field and the distal portion of coaxial cable 102. This in turn reduces the risk of ablating tissue proximal to the distal end of coaxial cable 102. Further, the microwave field is substantially uniform along the length of antenna 104 as compared to a comparable monopole antenna. Thus the lesion formed by the microwave field in FIGS. 2A and 2B will be uniform and substantially localized to the extent of antenna 104. Also, FIGS. 2A and 2B show that the microwave field volumetrically envelops entire antenna 104. Thus, embodiments of linear antenna 104 designed to operate at 915 MHz and other microwave frequencies may be designed that can create uniform, symmetrical, continuous, linear lesions with a lesion length greater than 35 mm.

In alternate embodiments, the SAR profile may be designed to be substantially non-uniform along the length of a linear antenna 104. For example, an antenna 104 may be designed to have a SAR profile that is wider and/or stronger at the center of antenna 104 and is less strong at the ends of antenna 104. In order to achieve this, one or more design parameters of antenna 104 in FIG. 1C may be modified. Examples of such modifications include, but are not limited to: adding of one or more additional conductive shaping elements 114; varying the width and/or the crossection shape of shaping element 114 and/or radiating element 112 along the length of antenna 104; varying the pitch of helical radiating element 112 and/or helical shaping element 114 along the length of antenna 104; varying the thickness, type and other design parameters of one or more antenna dielectrics 116, etc.

Figure 2D:
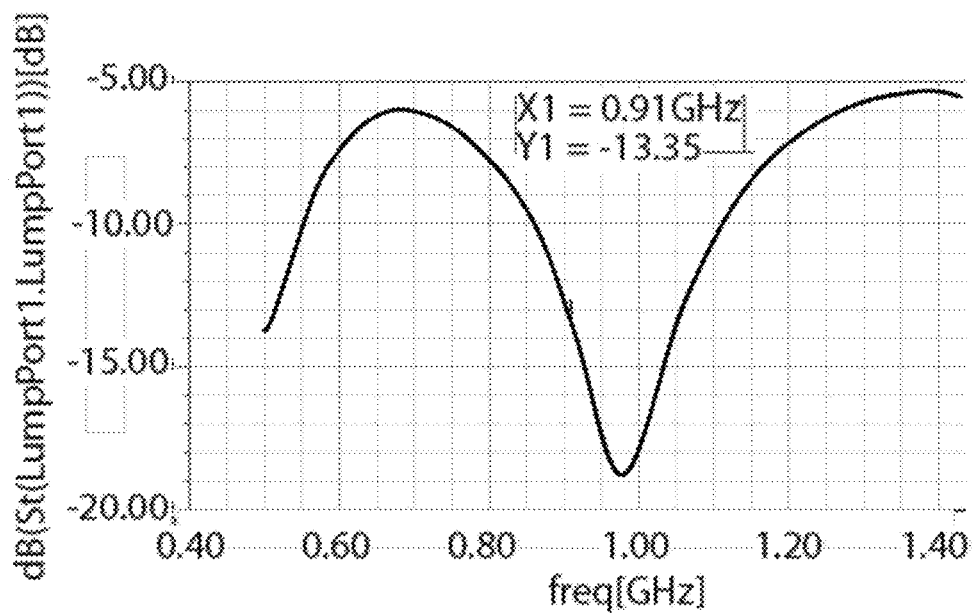
FIG. 2D shows the simulated return loss of an ablation device with an antenna of FIG. 2A.
Figure 2E:
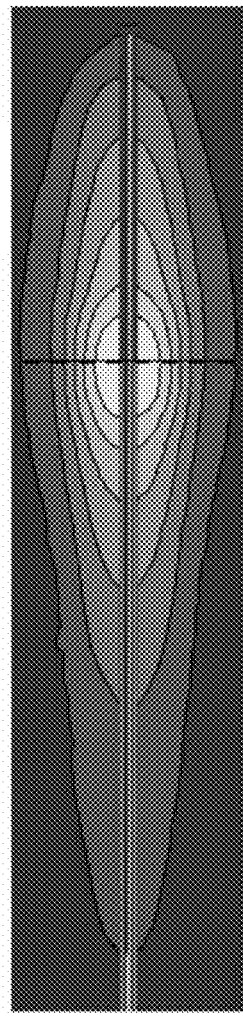
FIGS. 2E and 2F show a side view and the top view respectively of a simulated SAR profile generated by a monopole antenna.
Figure 2E:
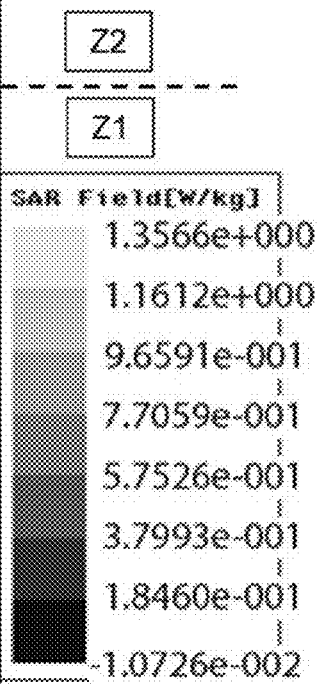

FIG. 2D shows the simulated return loss of an ablation device with an antenna of FIG. 1C. The simulated return loss shows good matching (about −13.35 dB) at 915 MHz.

Figure 2F:
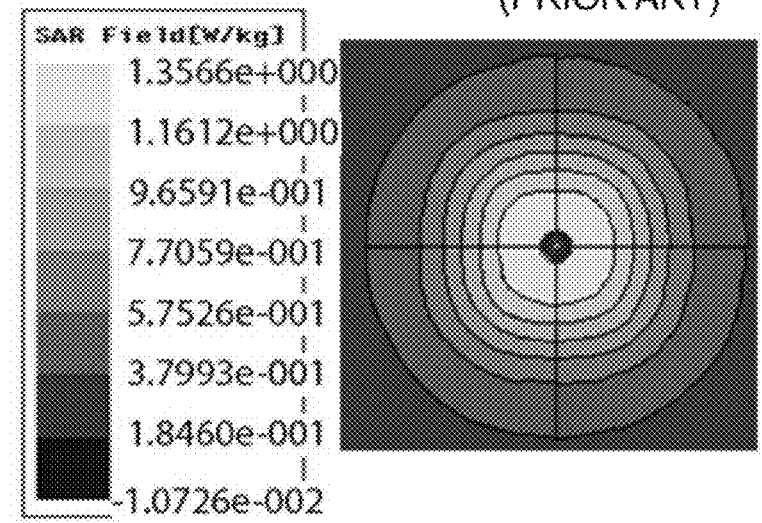

Antenna 104 in FIG. 1C has several advantages over a comparable monopole antenna. FIGS. 2E and 2F show a side view and the top view respectively of a simulated SAR profile generated by a monopole antenna. FIG. 2E shows the presence of a region of concentrated microwave field or a "hot spot" near the distal end of the transmission line (e.g. a coaxial cable) or at the proximal end of the monopole antenna. Thus the microwave field in FIG. 2E is non-uniform as compared to the field in FIG. 2B. About half of the microwave field in FIG. 2F is present in first zone Z1. Thus, there is a significant amount of microwave field present in first zone Z1. Thus, there is a high risk of ablating tissue proximal to the distal end of coaxial cable 102. The presence of a significant amount of microwave field in first zone Z1 is due to undesirable coupling between the microwave field and the outer conductor of the coaxial cable or other transmission line. This undesirable coupling can also cause backward heating of coaxial cable 102 that may lead to collateral damage of healthy tissue.

Figure 2G:
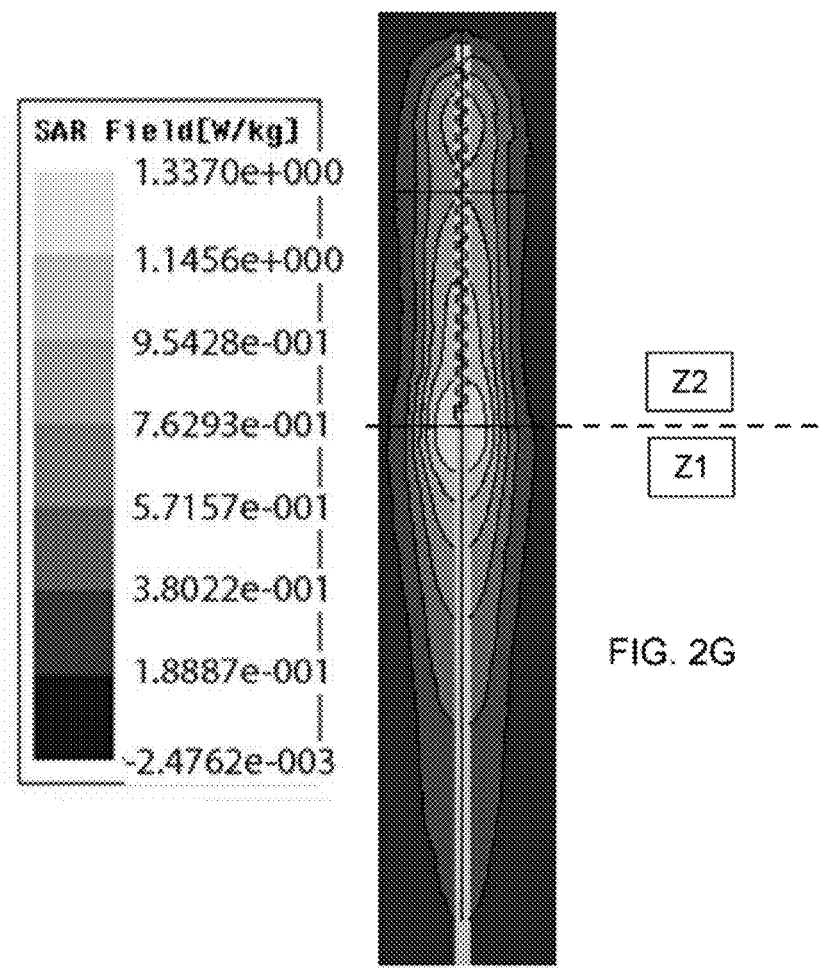
FIG. 2G shows a side view of a simulated SAR profile generated by the device embodiment of FIG. 2A without shaping element 114.
Figure 2H:
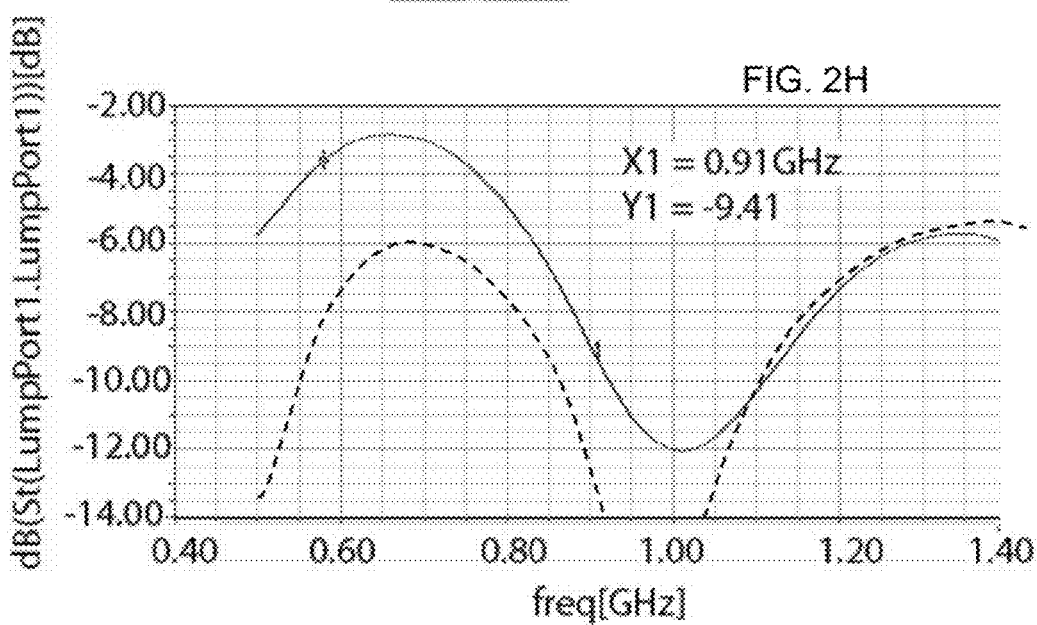
FIG. 2H shows the simulated return loss of an ablation device with an antenna of FIG. 2A without shaping element 114.

In several of the embodiments herein, shaping element 114 plays a critical role in shaping the microwave field generated by antenna 104. FIG. 2G shows a side view of a simulated SAR profile generated by the device embodiment of FIG. 1C without shaping element 114. The microwave field shown in FIG. 2G is an unshaped field since it is not shaped by shaping element 114. It is seen that antenna 104 in FIG. 2G behaves similar to a monopole antenna of FIG. 2E. FIG. 2G shows the presence of a region of concentrated microwave field or a "hot spot" near the distal end of the coaxial cable 102 or at the proximal end of the antenna 104. Thus the unshaped microwave field in FIG. 2G is non-uniform as compared to the shaped microwave field shaped by shaping element 114 in FIG. 2B. About half of the unshaped microwave field in FIG. 2G is present in first zone Z1. Thus, there is a significant amount of microwave field present in first zone Z1. Thus, there is a high risk of ablating tissue proximal to the distal end of coaxial cable 102. The presence of a significant amount of microwave field in first zone Z1 is due to undesirable coupling between the microwave field and the outer conductor of the coaxial cable 102 or other transmission line. This undesirable coupling can also cause backward heating of coaxial cable 102 that may lead to collateral damage of healthy tissue. FIG. 2H shows the simulated return loss (solid line) of an ablation device with an antenna of FIG. 1C without shaping element 114. The simulated return loss shows a matching (about −9.41 dB) at 915 MHz that is much lower in magnitude than the good matching (about −13.35 dB) at 915 MHz obtained with the antenna of FIG. 1C (dashed line in FIG. 2H). Thus, the design of shaping element 114 in antenna 104 of FIG. 1C improves the matching.

Shaping element 114 may be used to provide an additional resonance point in the frequency spectrum. This in turn may be used to increase the frequency range (bandwidth) over which antenna 104 delivers an acceptable performance. For example, the design of shaping element 114 in FIG. 1C improves the frequency range over which important performance parameters are acceptable. In FIG. 2H if the solid and dashed lines are compared, at a cutoff of −10 dB, the acceptable frequency range in the embodiment containing shaping element 114 is about 0.23 GHz (spanning from approximately 0.87 GHz to approximately 1.10 GHz). The acceptable frequency range in the comparable embodiment of FIG. 2G without shaping element 114 is only about 0.19 GHz (spanning from approximately 0.93 GHz to approximately 1.12 GHz). Thus in the first case, a larger frequency range (bandwidth) is available over which antenna 104 delivers an acceptable performance. This in turn allows for a design of antenna 104 wherein minor distortions of antenna 104 during typical clinical use or due to minor manufacturing variations do not significantly affect the performance of antenna 104.

Figure 2I:
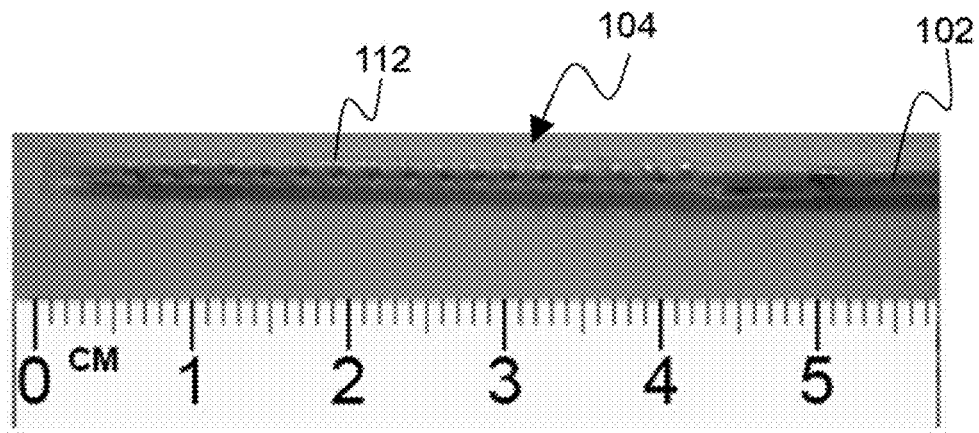
FIG. 2I shows a photograph of a fully functional, linear antenna similar to the design in FIG. 2A.

FIG. 2I shows a photograph of a fully functional, linear antenna similar to the design in FIG. 1C. In FIG. 2I, the multiple turns of radiating element 112 surround shaping element 114 (not visible). Entire antenna 104 is covered with a layer of a transparent dielectric material. The linear length of antenna 104 from the distal end of coaxial cable 102 till the distal end of radiating element 112 is about 4.5 cm. Alternate embodiments of antenna 104 may be designed with a linear length ranging from 2.5-5.5 cm. The outer diameter of antenna 104 in FIG. 2I is about 2 mm. Alternate embodiments of antenna 104 may be designed with an outer diameter ranging from 1.5-4 mm.

Figure 2J:
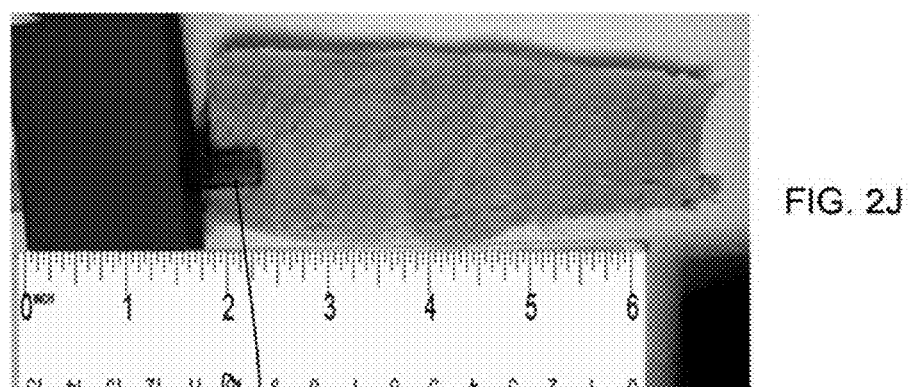
FIG. 2J shows an experimental setup for demonstrating the utility of the antenna of FIG. 2I for intra-cardiac ablation and other applications.
Figure 2K:
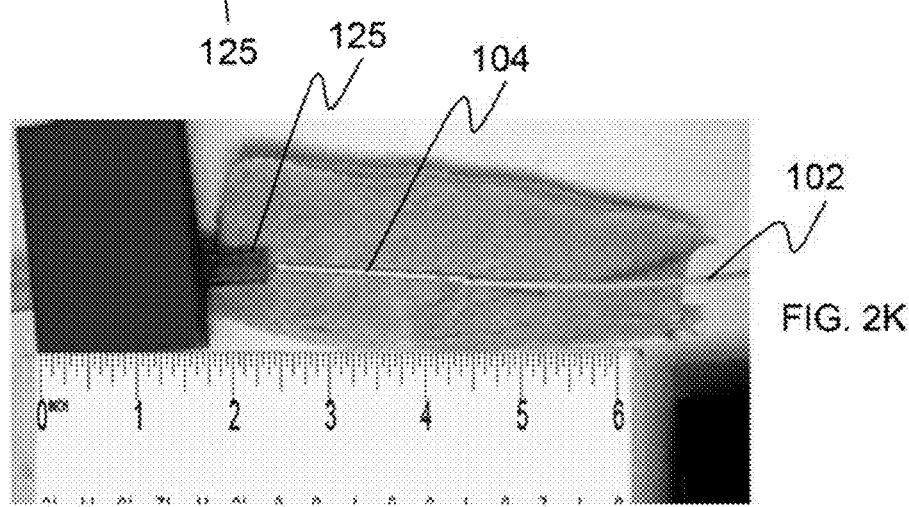
FIGS. 2K-2N show the method steps of a method of creating two overlapping lesions in a tissue.

FIG. 2J shows an experimental setup for demonstrating the utility of antenna 104 of FIG. 2I for intra-cardiac ablation and other applications. In FIG. 2J, a slice of porcine muscle tissue is kept in a water bath maintained at 37 C. Further, water is pumped in the water bath from a nozzle 125 and is continuously circulated through the water bath using a pump (not shown). This is to simulate the effect of blood flow within the heart chambers. FIG. 2J shows an unablated slice of porcine muscle tissue.

Figures 2L, 2M, 2N:
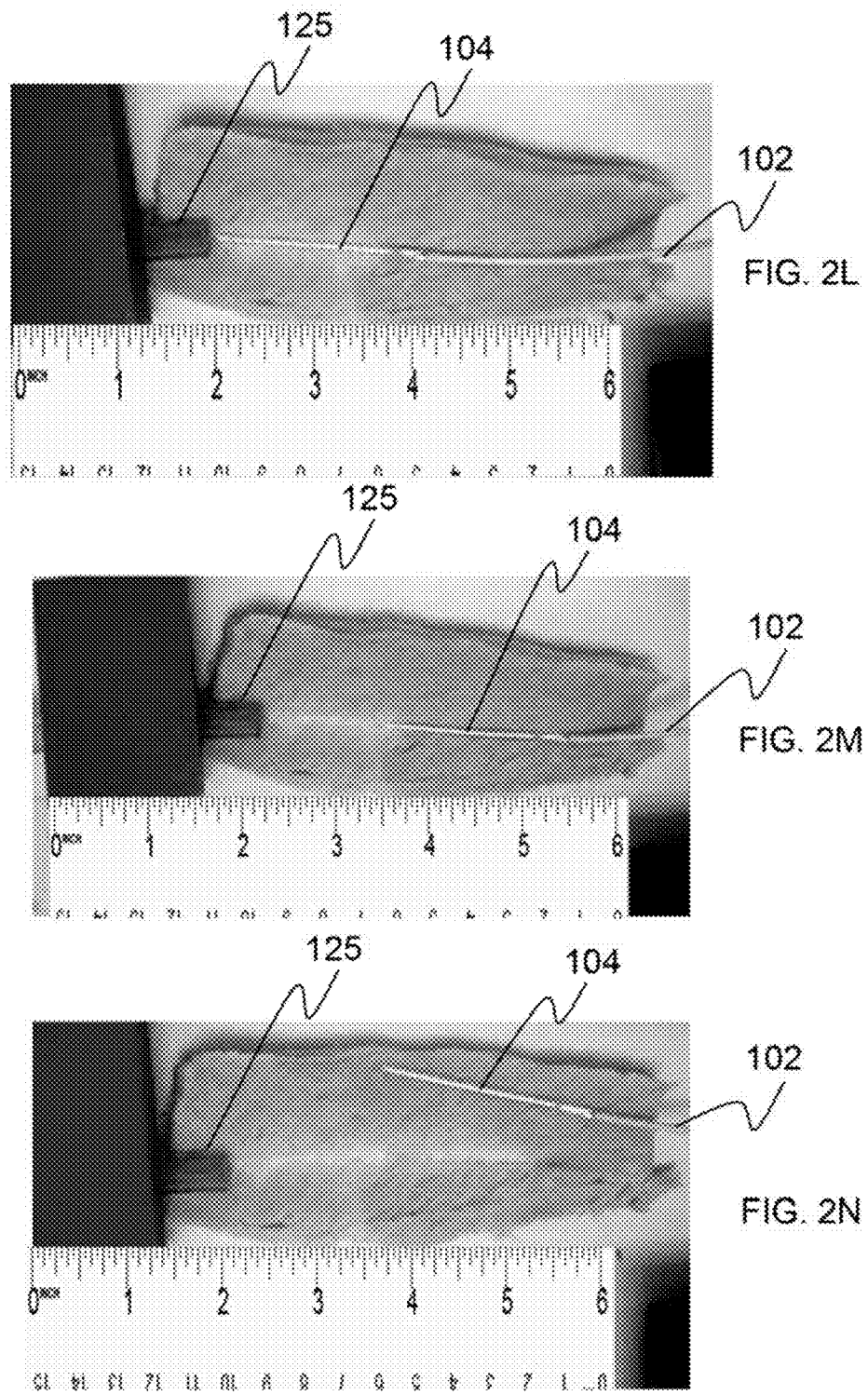

FIGS. 2J-2N show the method steps of a method of creating two overlapping lesions in a tissue. In FIGS. 2J-2N, the method is demonstrated in the setup of FIG. 2J. In FIG. 2J, a linear antenna 104 of FIG. 2I is placed in contact with the porcine tissue as shown. Thereafter, microwave power at 0.915 GHz is delivered to ablation device 100 at 80 W for 60 s. FIG. 2L shows a first ablation created around antenna 104. In FIG. 2M, antenna 104 is moved to a new location. Thereafter, microwave power is delivered to ablation device 100 at 80 W for 60 s to create a second lesion as shown in FIG. 2N. In FIG. 2N, antenna 104 is being moved away after creating the second lesion. Various patterns of multiple lesions may thus be created by repositioning any of the antennas 104 disclosed herein. Any of the antennas 104 disclosed herein may be repositioned by one or more of: rotating around an axis, moving proximally or distally, moving sideways, revolving around an axis, increasing or reducing in size, engaging a steering or deflecting mechanism on ablation device 100 and engaging a steering or deflecting mechanism on an accessory device. Further, any of the antennas 104 disclosed herein may be designed and used such that during clinical use the forces exerted by a flexible antenna 104 on surrounding tissues do not distort the surrounding tissue. In one embodiment, two lesions are created that do not intersect each other. In another embodiment, two elongate lesions are created that are joined lengthwise. In another embodiment, two elongate lesions are created that are joined breadthwise. In another embodiment, two elongate lesions are created that intersect each other to form an approximately X-shaped resulting lesion.

Figure 2O:
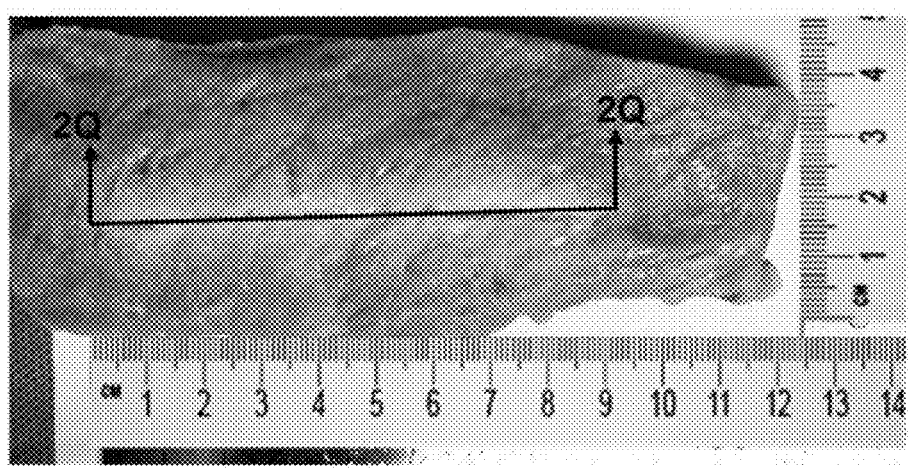
FIG. 2O shows a surface view of the two resulting overlapping lesions obtained from the method in FIGS. 2K-2N.

FIG. 2O shows a surface view of the two resulting overlapping lesions obtained from the method in FIGS. 2J-2N. In FIG. 2O, it is seen that the visual zone of ablation extends about 6-10 mm in breadth and about 9 cm in total length. By changing one or more of: ablation time, ablation power, antenna 104 design, antenna 104 position, the length and/or the breadth of the lesion may be varied.

Figure 2P:
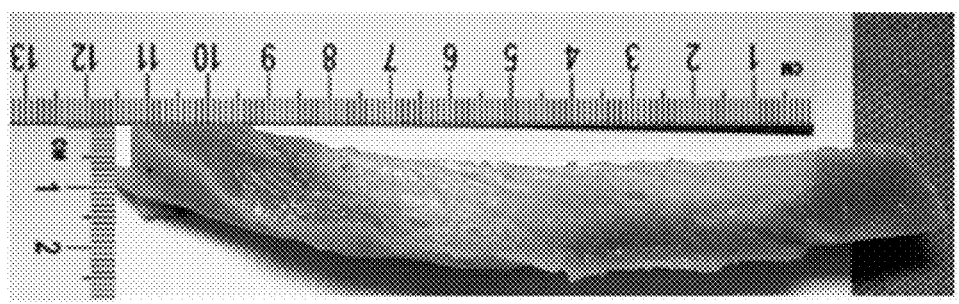
FIG. 2P shows a view of the section through the plane 2P-2P in FIG. 2O showing two deep, overlapping lesions.

FIG. 2P shows a view of the section through the plane 2P-2P in FIG. 2O showing two deep, overlapping lesions. In FIG. 2P, the length of the combined lesion is about 9 cm and the visual depth of the lesion varies from 1-1.5 cm. Thus, long, deep lesions may be created by antenna 104. The lesions may be created such that they span the entire thickness of the tissue such as a heart wall. Thus antenna 104 can be used to create trans-mural lesions. Further, there is a complete absence of charring in the lesion. Also, long, deep lesions were created even in the presence of flowing fluid. Thus antenna 104 may be used to create lesions in anatomical regions that contain flowing blood such as the vasculature (veins, arteries, etc.) and the heart chambers.

Figure 2Q:
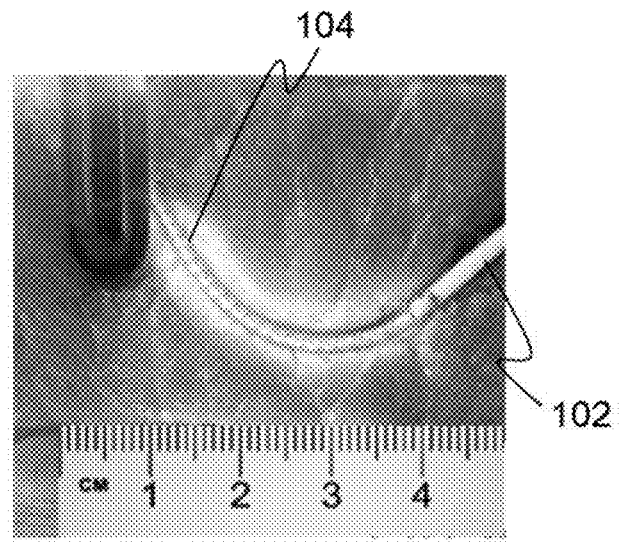
FIGS. 2Q and 2R show a uniform lesion created by the antenna in FIG. 2I in a bent or curved configuration.
Figure 2R:
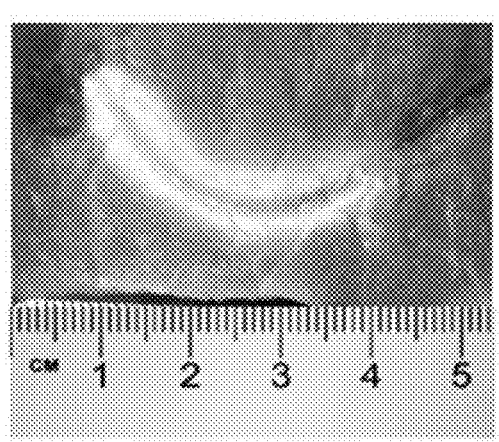

FIGS. 2Q and 2R show a uniform lesion created by the antenna in FIG. 2I in a bent or curved configuration. In FIG. 2R, the antenna 1904 has been moved away to show the underlying lesion. FIGS. 2Q and 2R show that the lesion is bent or curved and corresponds to the bent or curved profile of antenna 104. Further, there is no burning or charring of the surface of the tissue. Thus antenna 104 embodiments such as the embodiment in FIG. 1C are capable of creating uniform lesions even in a bent or curved configuration. This is very important in applications such as electrophysiological ablation of cardiac tissue for treating arrhythmias where the ability to create long, curved or bent lesions enables the user to complete the procedure faster and with improved outcomes.

Figure 3A:
FIGS. 3A-3D show embodiments of antenna 104 wherein antenna 104 has linear, curved, closed loop and helical shapes respectively.
Figure 3B:
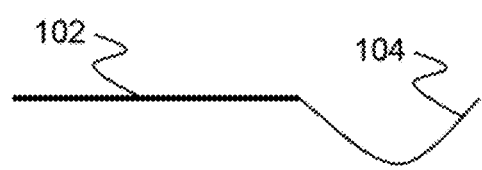
Figure 3C:
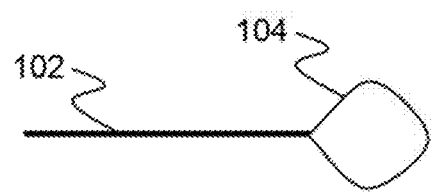
Figure 3D:
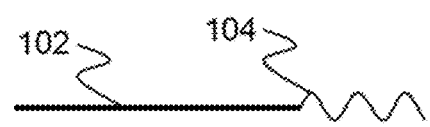

Any of the antennas 104 herein such as linear antenna 104 of FIG. 1C may be shaped or otherwise modified for a variety of specific applications. FIGS. 3A-3D show embodiments of antenna 104 wherein antenna 104 has linear, curved, closed loop and helical shapes respectively. The shape embodiments shown in FIGS. 3A-3D may have a fixed shaped or may be user-shapeable. For example, antenna 104 may be provided with a pull wire or a similar shape distorting element to reversibly change the shape of antenna 104 from a linear shape as shown in FIG. 3A to a more curved or bent shape as shown in FIG. 3B and vice versa. In another example, a distal region of antenna 104 may be provided with a pull wire or a similar shape distorting element to reversibly change the shape of antenna 104 from a linear shape as shown in FIG. 3A to a more looped shape as shown in FIG. 3C and vice versa. Examples of mechanisms that may be used to change the shape of antenna 104 include, but are not limited to internal or external pull wires, balloons, inflatable structures and straight or bent slidable stylets. Any of the antennas 104 disclosed herein may be used to create ablations that substantially correspond to the shape of antenna 104. For example, antenna 104 in FIG. 3A may be used to create a substantially linear lesion, antenna 104 in FIG. 3B may be used to create a substantially curved or bent lesion, antenna 104 in FIG. 3D may be used to create a helical lesion, etc. Any of the antennas 104 disclosed herein may be used to create ablations that do not substantially correspond to the shape of antenna 104. For example, antenna 3C may be used to create a round lesion, a point lesion or a linear lesion as better illustrated in FIGS. 3I-3L. Any of the antennas 104 disclosed herein may be used to penetrate through a body tissue to ablate a target. To facilitate the penetration though tissue, a distal end of any of antenna 104 disclosed herein may be modified (e.g. by having a sharp tip) to facilitate a penetration of tissue. For example, antenna 104 of FIG. 3A may be designed to be sufficiently stiff and have a sharp distal tip to penetrate skin to ablate abdominal and other internal organs. Alternately, antenna 104 of FIG. 3A may be designed to be sufficiently flexible to enable the introduction of antenna 104 through natural openings and passages of the body or through a catheter. In another example, antenna 104 of FIG. 3D may be designed to be sufficiently stiff and have a sharp distal tip to penetrate a tissue surface and be insertable in a corkscrew-like manner to access underlying tissue. In another embodiment, antenna 104 of FIG. 3D is designed to be sufficiently flexible and collapsible to enable the introduction of antenna 104 through natural openings and passages of the body or through a catheter. The elastic or super-elastic or shape memory nature of antenna 104 may then enable antenna 104 to regain a helical shape after reaching a target tissue such as a lumen of a body passage or cavity e.g. a blood vessel.

Figure 3E:
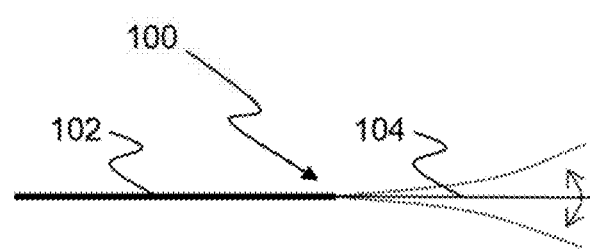
FIG. 3E shows an embodiment of an ablation device comprising a steerable or deflectable antenna.
Figure 3F:
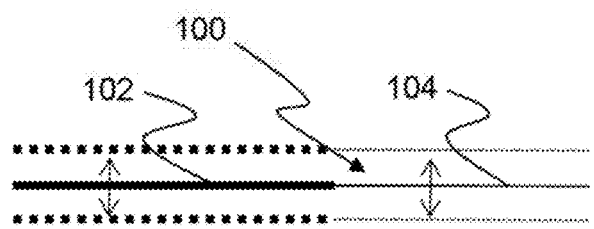
FIG. 3F shows an embodiment of an ablation device 100 that is repositioned to ablate multiple target regions.

Any of the antenna 104 disclosed herein may be repositioned once or multiple times during a procedure to access multiple regions of the body. This repositioning may be done by moving the whole or a part of ablation device 100. FIG. 3E shows an embodiment of an ablation device comprising a steerable or deflectable antenna. In FIG. 3E, ablation device 100 comprises an antenna 104 that is controllably steerable or deflectable. Thus, antenna 104 is able to access various target regions without moving entire ablation device 100. In one embodiment, ablation device 100 of FIG. 3E is inserted into a cavity or a lumen. Examples of such cavities or lumens include, but are not limited to: natural or artificially created cavities or lumens in portions of the male urinary tract, gall bladder, uterus and other portions of the female reproductive tract, regions of the vasculature, intestine and other portions of the lower alimentary tract, stomach and other portions of the upper alimentary tract, liver and other digestive organs, lungs, skin, mucus membranes, kidneys, reproductive organs, or other organs or soft tissues of the body. Antenna 104 is positioned to access a first region of tissue and is used to ablate the first region of tissue. Thereafter, antenna 104 is deflected to access a second region of tissue and is used to ablate the second region of tissue. Thus, multiple regions of tissue may be ablated by antenna 104. Examples of mechanisms that may be used to steer or deflect antenna 104 include, but are not limited to internal or external pull wires, balloons, inflatable structures and straight or bent slidable stylets. Even though a linear antenna is shown in FIGS. 3E and 3F, any of the antennas 104 disclosed herein may be used to construct ablation device 100 in FIGS. 3E and 3F. In one embodiment, an entire target tissue area is ablated without repositioning the entire ablation device 100 while repositioning antenna 104 once or more. For example, an entire uterine endometrium may be ablated by an ablation device 100 that is inserted through the cervix into the uterine cavity after positioning an antenna 104 at at least 2 positions in the uterine cavity.

FIG. 3F shows an embodiment of an ablation device 100 that is repositioned to ablate multiple target regions. In FIG. 3F, a majority or all or ablation device 100 is repositioned to access multiple target regions. In one such embodiment, antenna 104 is placed on a first position on the surface of the liver and is used to ablate a first region of the liver. Thereafter, ablation device 100 is moved to position antenna 104 at a second position on the surface of the liver and antenna 104 is used to ablate a second region of the liver. Ablation device 100 may be moved sideways, forwards or backwards or in any other suitable motion. In a method embodiment, ablation device 100 is reinserted into a tissue after a first ablation to abate another region of tissue. For example, antenna 104 may be inserted inside the liver at a first position and is used to ablate a first region in the interior of the liver. Thereafter, antenna 104 is removed from the liver. Thereafter, antenna 104 is reinserted inside the liver at a second position and is used to ablate a second region in the interior of the liver. In another example, ablation device 100 is inserted in a heart cavity and antenna 104 is used to ablate a first region of the heart cavity to create a first lesion. Thereafter, antenna 104 is moved to a second location of the heart cavity and is used to ablate the second region of the heart cavity to create a second lesion. The first and second lesions may be overlapping or non-overlapping. In case of overlapping lesions, the first and second lesions may overlap in a substantially end-to-end or side-to-side overlap.

Figure 3G:
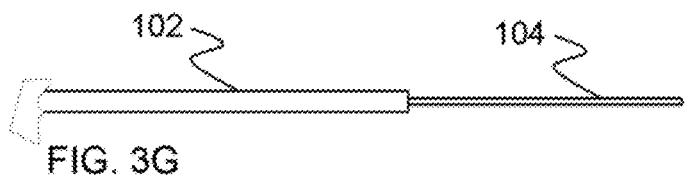
FIGS. 3G-3H show two configurations of a microwave device having an antenna that can be reversibly converted between a straight configuration and a bent configuration.
Figure 3H:
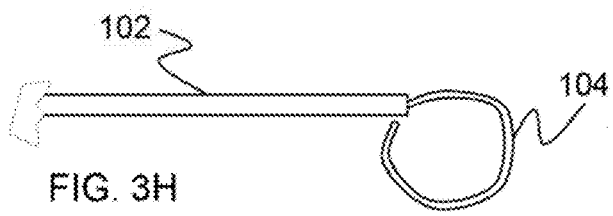

FIGS. 3G-3H show two configurations of a microwave device having an antenna that can be reversibly converted between a straight configuration and a bent configuration. In FIG. 3G, antenna 104 is substantially linear. A distal region of antenna 104 is connected to a pull wire or a tether. Tether may be located external to ablation device 100 and pass through an opening located on ablation device shaft. The opening may for example by an opening of an end-to-end lumen, an opening of a rapid-exchange lumen, an opening of a collapsible lumen, a loop etc. The proximal region of tether can be manipulated by a user. In FIG. 3H, a bending force is exerted on antenna 104. This bending force in turn causes antenna 104 to bend and assume a substantially non-linear shape such as in FIG. 3H. In FIG. 3H, antenna 104 has a substantially circular, closed loop shape. Examples of other non-linear shapes include, but are not limited to other closed loop shapes, open looped shapes, shapes enclosing one or more bends or curves, etc. Upon the release of the bending force, antenna 104 returns back to the substantially linear shape of FIG. 3G by elastic or super-elastic property of antenna 104. In an alternate embodiment, antenna 104 has a non-linear configuration that is reversibly converted to a substantially linear configuration on the application of a bending force.

Figure 3I:
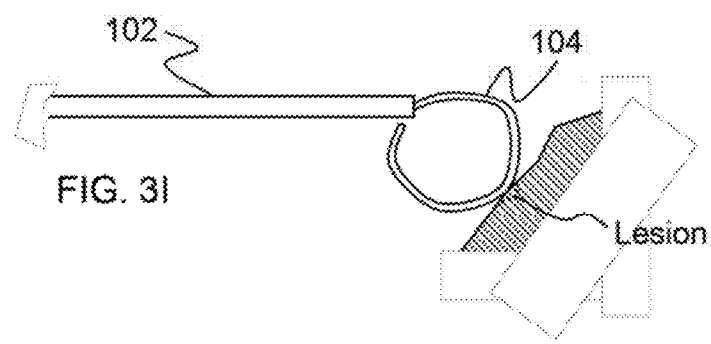
FIG. 3I shows an embodiment of a method used to create a small, localized "point" lesion on a tissue using the ablation device of FIGS. 3G and 3H.
Figure 3J:
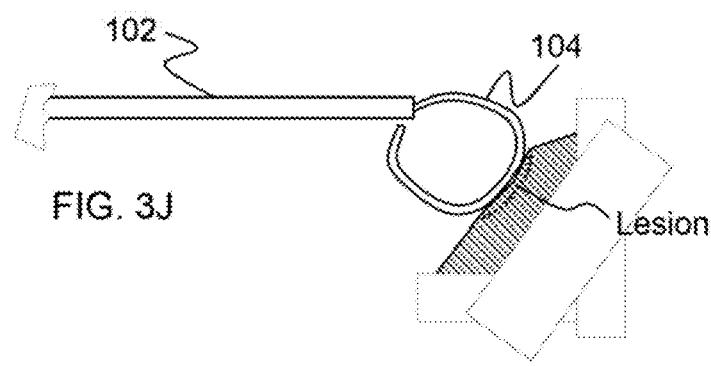
FIG. 3J shows an embodiment of a method used to create a linear lesion on a tissue using the ablation device of FIGS. 3G and 3H.
Figure 3K:
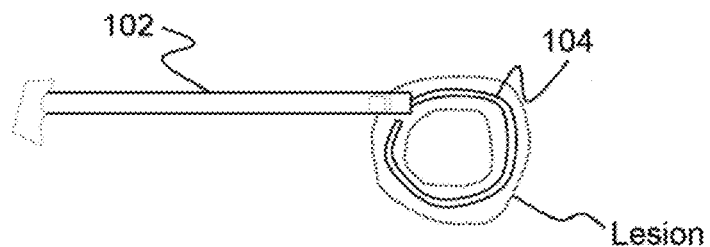
FIG. 3K shows an embodiment of a method used to create an annular lesion on a tissue using the ablation device of FIGS. 3G and 3H.
Figure 3L:
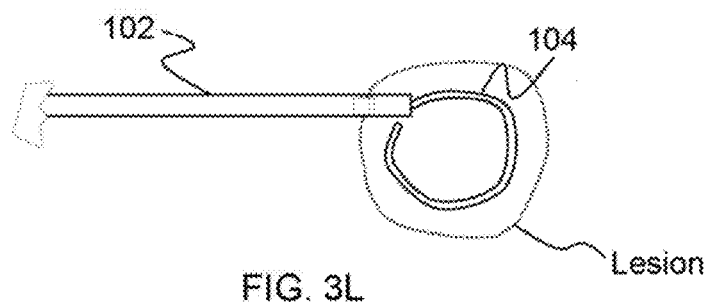
FIG. 3L shows an embodiment of a method used to create a round lesion on a tissue using the ablation device of FIGS. 3G and 3H.

The ablation device in FIGS. 3G and 3H may be used to create a variety of lesions such as small, localized "point" lesions, linear lesions, area lesions and volumetric lesions. For example, FIG. 3I shows an embodiment of a method used to create a small, localized "point" lesion on a tissue using the ablation device of FIGS. 3G and 3H. In FIG. 3I, antenna 104 is in a non-linear configuration. A portion of the antenna 104 is in contact with tissue. The contact between antenna 104 and the tissue is made with a force sufficient to enable antenna 104 to contact the tissue but not sufficient to distort or flatten antenna 104. Thereafter, energy is delivered by antenna 104 to the tissue to create the "point" lesion. FIG. 3J shows an embodiment of a method used to create a linear lesion on a tissue using the ablation device of FIGS. 3G and 3H. In FIG. 3J, antenna 104 is in a non-linear configuration. A portion of the antenna 104 is in contact with tissue. The contact between antenna 104 and the tissue is made with a force sufficient to distort or flatten antenna 104 such that the contact surface between antenna 104 and the tissue is substantially linear. Thereafter, energy is delivered by antenna 104 to the tissue to create the substantially linear lesion. FIG. 3K shows an embodiment of a method used to create an annular lesion on a tissue using the ablation device of FIGS. 3G and 3H. In FIG. 3K, antenna 104 is in a non-linear configuration. A portion of the antenna 104 is in contact with tissue. The contact between antenna 104 and the tissue is made such that antenna 104 is substantially in the plane of the tissue surface. Thereafter, energy is delivered by antenna 104 to the tissue to create the substantially annular lesion. Various parameters such as the ablation time, ablation power, etc. may be changed or manipulated in any of the methods described herein to achieve the desired clinical outcome. The microwave energy may be delivered in a continuous mode or in a discontinuous mode. In the embodiment in FIG. 3K, microwave energy is delivered such that the region of tissue immediately adjacent to antenna 104 is ablated. This creates an annular lesion as shown in FIG. 3K. FIG. 3L shows an embodiment of a method used to create a round lesion on a tissue using the ablation device of FIGS. 3G and 3H. In FIG. 3L, antenna 104 is in a non-linear configuration. A portion of the antenna 104 is in contact with tissue. The contact between antenna 104 and the tissue is made such that antenna 104 is substantially in the plane of the tissue surface. Thereafter, energy is delivered by antenna 104 to the tissue to create the substantially round lesion. In the embodiment in FIG. 3L, microwave energy is delivered for a longer time and/or with higher power than in the method in FIG. 3K such that a round shaped region of tissue adjacent to antenna 104 is ablated. This round lesion may be restricted to the surface of the tissue. Alternately, with a higher ablation power and/or longer ablation time, the lesion may extend sufficiently deep into the tissue to create a volumetric lesion.

The shape of antenna 104 may be modified during a procedure to target two different regions of target tissue. For example, antenna 104 of FIG. 1C may be inserted inside tissue (e.g. liver, brain, etc.) and used to ablate tissue deep inside the organ. In order to achieve this, antenna 104 (e.g. antenna 104 of FIG. 1C) may be inserted while enclosed inside a sufficiently stiff outer sheath made of a dielectric material. In the same procedure, antenna 104 may be bent or curved as shown in FIGS. 3K and 3L and thereafter used to ablate a surface of organ. This eliminates the need for two separate devices—one for ablating deeper tissue and one for ablating surface tissue. This in turn will reduce the procedure complexity and costs.

Figure 4A:
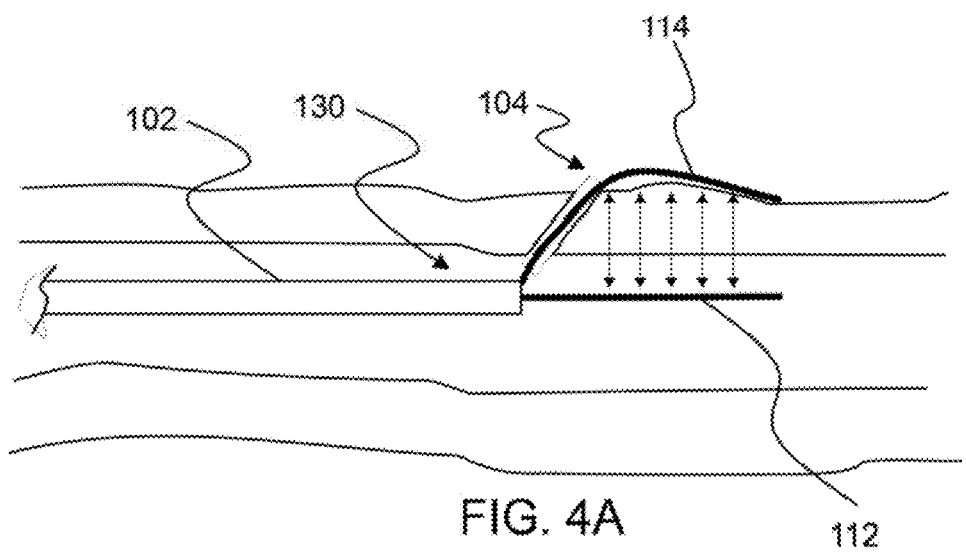
FIGS. 4A and 4B show two method embodiments of ablating tissue wherein a radiating element and a shaping element of an antenna are placed on opposite sides of the tissue.
Figure 4B:
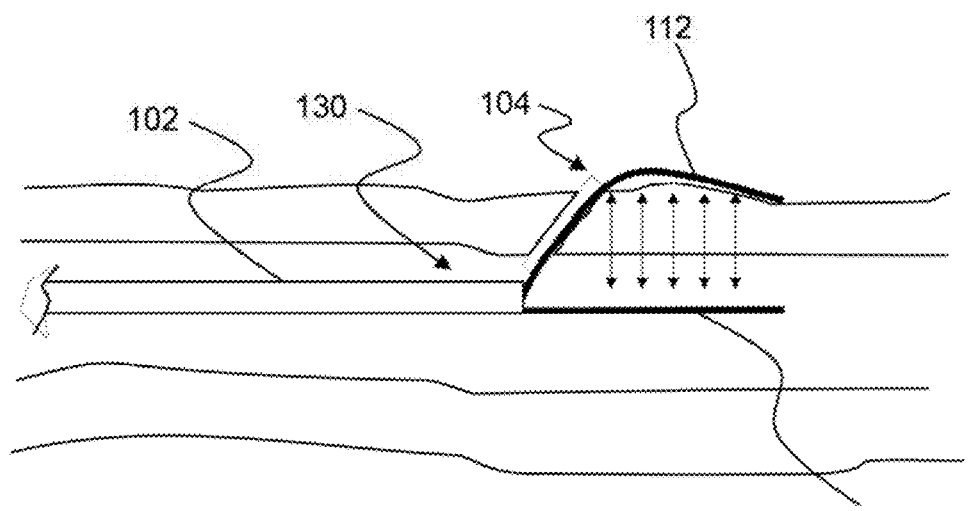

FIGS. 4A and 4B show two method embodiments of ablating tissue wherein a radiating element and a shaping element of an antenna are placed on opposite sides of the tissue. In FIG. 4A, ablation device 100 is introduced in a lumen 130 or a body cavity. Examples of such lumens 130 or body cavities include but are not limited to: natural or artificially created cavities or lumens in portions of the male urinary tract, gall bladder, uterus and other portions of the female reproductive tract, regions of the vasculature, intestine and other portions of the lower alimentary tract, stomach and other portions of the upper alimentary tract, liver and other digestive organs, lungs, skin, mucus membranes, kidneys, reproductive organs, or other organs or soft tissues of the body. Antenna 104 is positioned near the target tissue such that radiating element 112 and shaping element 114 are placed on opposite sides of the target tissue. In FIG. 4A, radiating element 112 is located in the lumen 130 while shaping element 114 is located outside lumen 130. Antenna 104 is used to ablate a portion of the wall of lumen 130. Shaping element 114 may be located inside the tissue of the wall of lumen 130 or may be passed through a natural or artificially created opening to a location outside lumen 130 as shown in FIG. 4A. Shaping element 114 shapes the microwave field emitted by radiating element 112 such that the microwave field is concentrated in the region between radiating element 112 and shaping element 114. This concentrated microwave field in the region between radiating element 112 and shaping element 114 is used to ablate tissue. In FIG. 4B, shaping element 114 is located in the lumen 130 while radiating element 112 is located outside lumen 130.

Figure 4C:
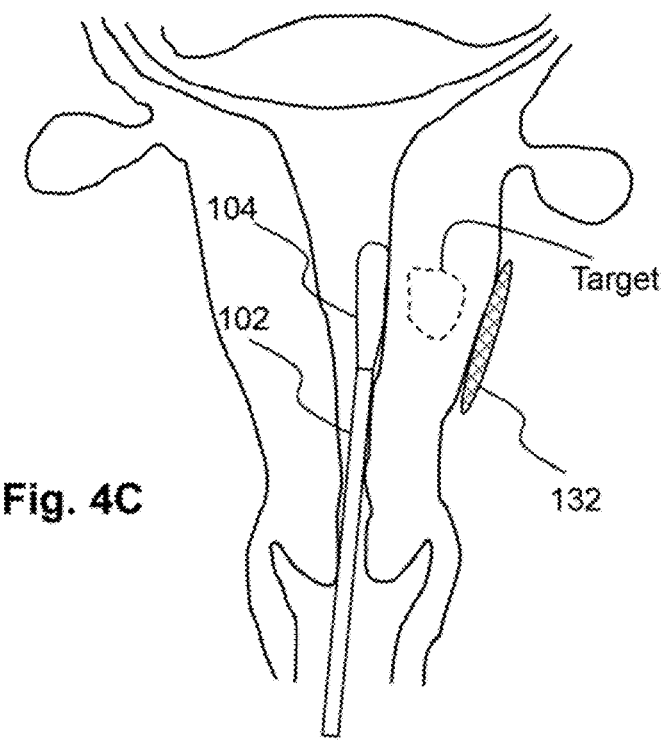
FIGS. 4C and 4D show two method embodiments of ablating tissue located between an antenna and a shaping element such as a microwave shield or reflector.
Figure 4D:
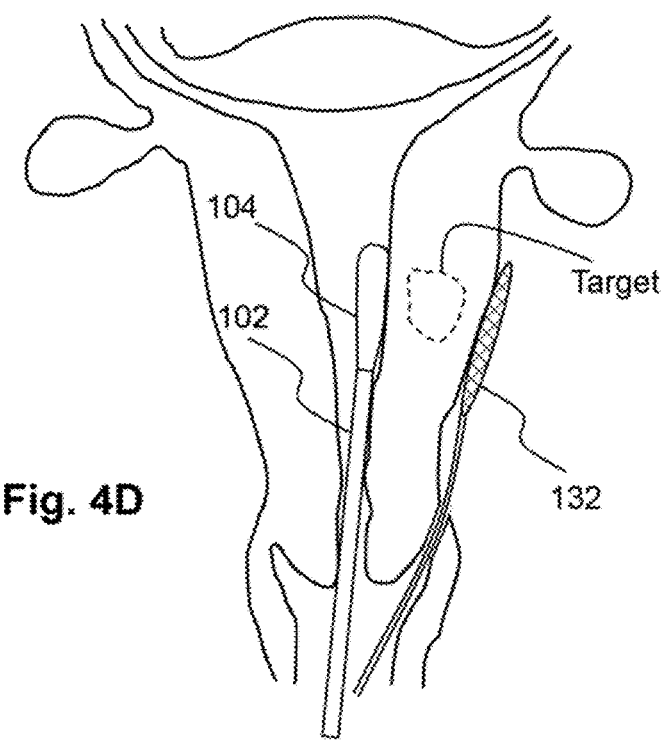

FIGS. 4C and 4D show two method embodiments of ablating tissue located between an antenna and a microwave shield or reflector. FIG. 4C shows a method embodiment of ablating tissue in a wall of the uterus located between an antenna and a microwave shield or reflector. In FIG. 4C, an antenna 104 is introduced inside the uterine cavity. Antenna 104 generates a microwave field that is used to ablate tissue adjacent to antenna 104. In FIG. 4C, antenna 104 is navigated in the uterine cavity and is placed adjacent to the target tissue to be ablated. Examples of such target tissues include, but are not limited to: fibroids, cancerous lesions, adenomyosis, polyps and portions of the endometrium. Further, in FIG. 4C, a microwave reflector or shield 132 is placed on the external surface of the uterus i.e. on the surface of the uterine serosa. Microwave reflector or shield 132 is used to shield or reflect any microwave energy that reaches the external surface of the uterus. Microwave reflector or shield 132 may be made of conductive or dielectric materials or combinations thereof. This increases the safety of the procedure by reducing the risk of collateral damage of tissue. Microwave reflector or shield 132 may be introduced through a laparoscopic incision, trans-vaginally, through a laparotomy, or through other methods known in the art to introduce devices on the surface of the uterus. In an alternate embodiment, the positions of antenna 104 and microwave reflector or shield 132 are swapped. In this embodiment, the microwave reflector or shield 132 is not a part of antenna 104.

FIG. 4D shows a method embodiment of ablating tissue in a wall of the uterus similar to the method in FIG. 4C. However, in FIG. 4D, microwave reflector or shield 132 is introduced in the desired position through a trans-vaginal approach. Microwave reflector or shield 132 may or may not be electrically connected to one or more portions of coaxial cable 102 such as outer conductor 106. In this embodiment, the microwave reflector or shield 132 may or may not be a part of antenna 104. Similar to the method in FIG. 4C, the positions of antenna 104 and microwave reflector or shield 132 may be swapped. Methods similar to those illustrated in FIGS. 4C and 4D may be used to treat other anatomical regions such as anatomical cavities or lumens or tissue volumes. In one such embodiment, an antenna 104 is placed in an endocardial location and a microwave reflector or shield 132 is placed in a pericardial location or vice versa. Microwave reflector or shield 132 may be made of conductive or dielectric materials or combinations thereof. In one antenna 104 embodiment, a shaping element 114 may act as a microwave reflector or shield 132.

Figure 5A:
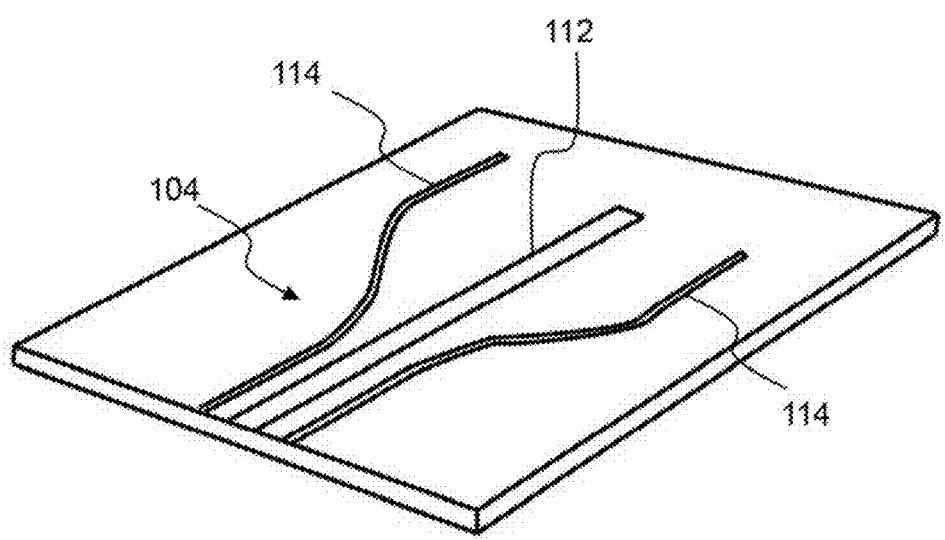
FIG. 5A shows an embodiment of a portion of an antenna built on a printed circuit board.

FIG. 5A shows an embodiment of a portion of an antenna built on a printed circuit board. In FIG. 5A, a portion of antenna 104 is printed on a rigid or flexible, generally planar printed circuit board. In any of the embodiments herein, the whole or portions of antenna 104 may be printed on one or more rigid or flexible, planar or non-planar printed circuit boards.

Figure 6A:
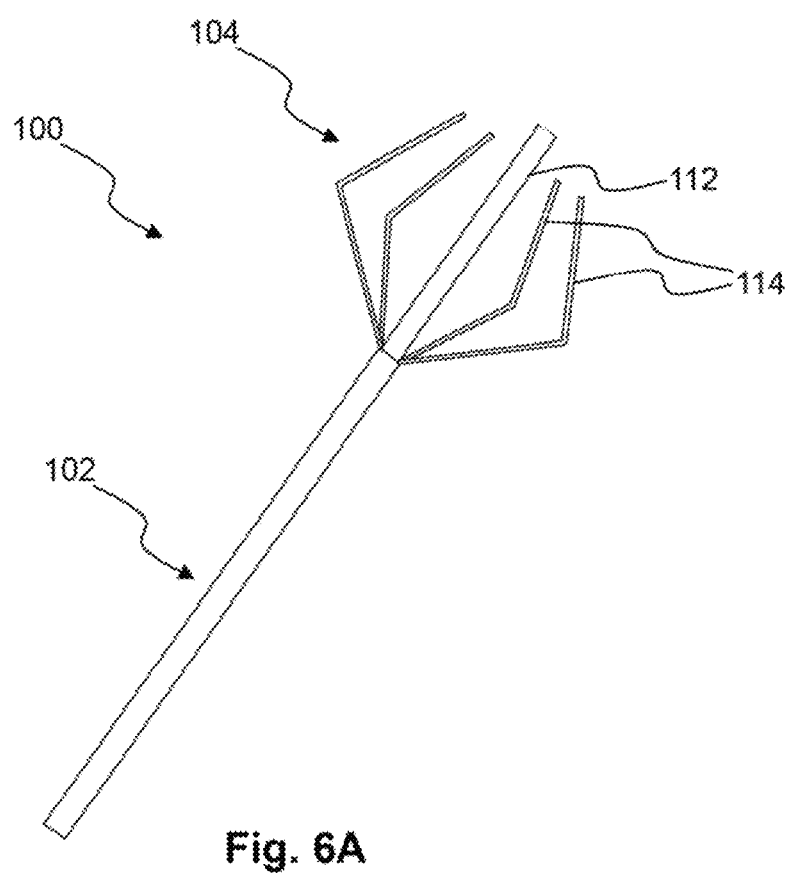
FIG. 6A shows an embodiment of an ablation device with a radiating element and multiple shaping elements adapted to ablate a volume of tissue.

The devices and methods disclosed herein and modifications thereof may be used during minimally invasive or invasive treatment of tissue. For example, FIG. 6A shows an embodiment of an ablation device with a three dimensional antenna comprising a radiating element and multiple shaping elements adapted to ablate a volume of tissue. In FIG. 6A, ablation device 100 comprises an antenna 104 comprising a substantially linear radiating element 112. Antenna 104 further comprises a plurality of shaping elements 114. In FIG. 6A, the four shaping elements 114 are identical and are arranged symmetrically around radiating element 112. Embodiments of antenna 104 may be designed with 1-10 shaping elements 114. Shaping elements 114 may be symmetrically or non-symmetrically arranged around radiating element 112. Shaping elements 114 may or may not be identical. In FIG. 6A, each shaping element 114 is elongate and comprises a bend or an angled region. In FIG. 6A, each shaping element is electrically connected to the outer conductor of coaxial cable 102 or other transmission line. The distal end of radiating element 112 and/or shaping elements 114 may comprise a sharp or penetrating tip. In one embodiment, shaping elements 114 are a retractable claw structure that extends from ablation device 100. In one embodiment, the design of radiating element 112 is similar to a 14 mm long monopole antenna. In FIG. 6A, shaping elements 114 shape and enhance the electromagnetic field in the volume between radiating element 112 and shaping elements 114.

This creates a large, volumetric lesion between radiating element 112 and shaping elements 114. The volumetric lesion will be substantially confined to the extent of shaping elements 114 as seen from FIGS. 6B and 6C. Further, shaping elements 114 reduce the leakage current that will otherwise be induced on the outer wall of the outer conductor of coaxial cable 102 or other transmission line.

When microwave energy is delivered through a transmission line to antenna 104 in FIG. 6A, a first microwave field is emitted by radiating element 112. The first microwave field interacts with shaping elements 114. This interaction induces a leakage current on shaping elements 114. The leakage current in turn creates a second microwave field. The first microwave field and the second microwave field together combine to produce a unique shaped microwave field of antenna 104 that is clinically more useful that the unshaped microwave field generated by an antenna 104 comprising only radiating element 112. Thus the original microwave field is redistributed by the design of shaping elements 114. Shaping elements 114 alone are not capable of functioning as an antenna; rather shaping elements 114 shape or redistribute the electromagnetic or microwave field emitted by radiating element 112 to produce a shaped microwave field that is clinically more useful. Further, the combination of radiating element 112 and shaping elements 114 improves the power deposition of antenna 104.

Figure 6B:
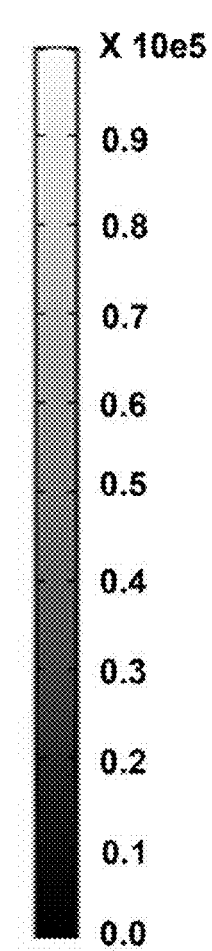
FIGS. 6B and 6C show a side view and a top view respectively of a simulated SAR profile of the embodiment of the antenna of FIG. 6A.
Figure 6B:
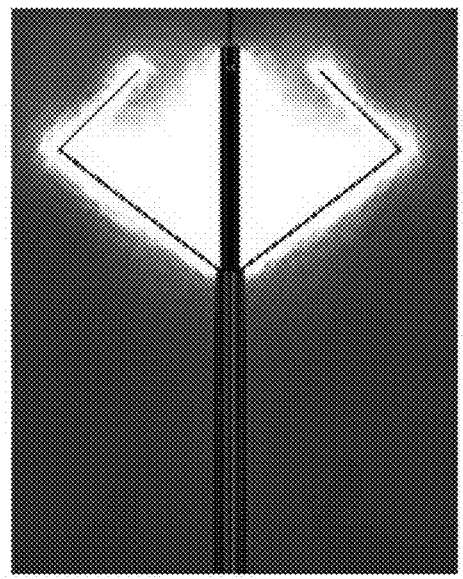

The microwave effect of shaping elements 114 can be seen by comparing FIG. 2E to FIG. 6B. In absence of shaping elements 114, antenna 104 in FIG. 6A acts as a monopole antenna similar to that shown in FIG. 2B. Thus FIG. 2B shows a first unshaped field that is not shaped by shaping elements 114. When the antenna 104 comprises shaping elements 114 as shown in FIG. 6A, the antenna generates a shaped microwave field as shown in FIG. 6B.

In an embodiment of a minimally invasive procedure, antenna 104 is inserted into the patient's body through small puncture wounds in the skin. Thereafter, antenna 104 is deployed such that the volume enclosed by the claw-like shaping elements 114 encloses the target tissue. For example, for cancer treatment, the target tissue is a tumor or a tissue with cancer cells. The degree of deployment of antenna 104 may be adjusted to suit different target tissue sizes (e.g. different tumor sizes). In one such embodiment, one or more pull wires or tethers are attached to shaping elements 114 to control the position of shaping elements 114. In another embodiment, shaping elements 114 are pre-shaped and are made of a material with shape memory properties such as Nitinol. Shaping elements 114 are retracted inside a catheter or a tubular structure in a collapsed configuration before inserting into the tissue. A low-profile catheter or a tubular structure is preferably used to reduce the trauma to healthy tissues during the insertion procedure. Once a portion of the catheter or tubular structure is inserted inside the target tissue, shaping elements 114 and radiating element 112 are deployed. Shaping elements 114 are deployed to their un-collapsed, preset shape by extending them from the catheter or tubular structure. Even though antenna 104 of FIG. 6A can be used for a variety of procedures, it is especially suited for ablating solid tumors such as those found in cancer (e.g. liver and lung cancer) and benign tumors (e.g. uterine fibroids).

Figure 6C:
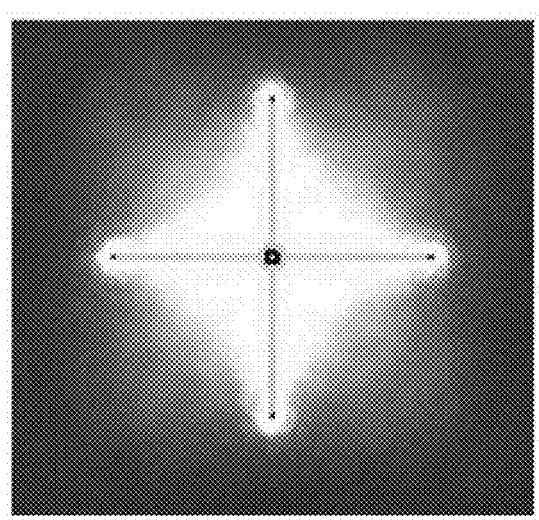
Figure 6C:
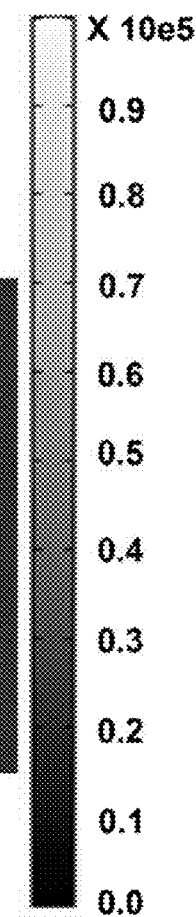

FIGS. 6B and 6C show a side view and a top view of a simulated SAR profile of an embodiment of the antenna of FIG. 6A. The SAR profile was simulated at 2.45 GHz using the COMSOL Multiphysics package to simulate an ablation in the liver. FIGS. 6B and 6C illustrate that a volumetric lesion created by antenna 104 will be substantially confined to the extent of shaping elements 114. Also, FIGS. 6B and 6C show that the microwave field volumetrically envelops entire antenna 104.

Figure 6D:
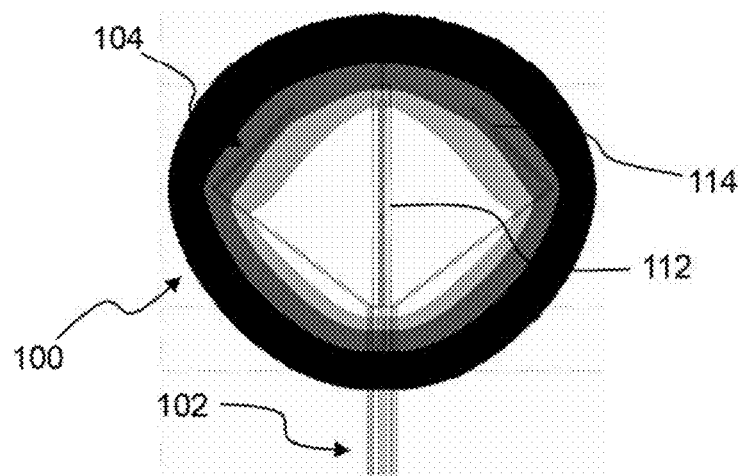
FIGS. 6D and 6E show a side view and a top view of a thermal simulation of the embodiment of the antenna of FIG. 6A.
Figure 6E:
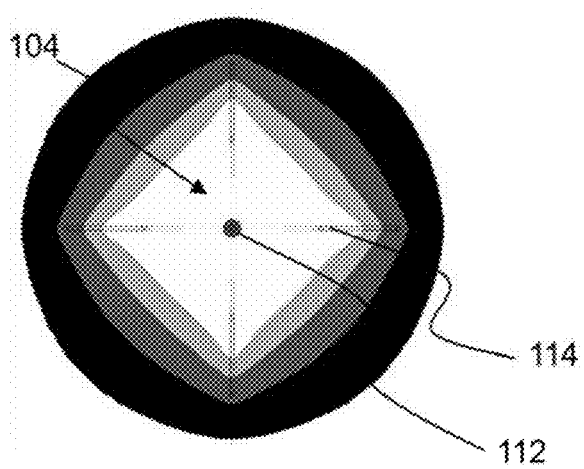

FIGS. 6D and 6E show a side view and a top view of a thermal simulation of an embodiment of the antenna of FIG. 6A. The outer most surface of the black zone is a 50° C. isosurface with a diameter or width of about 28 mm and longitudinal length of about 22 mm at steady state. Thus, antenna 104 is capable for forming a lesion with a diameter or width of about 28 mm and longitudinal length of about 22 mm. The 50° C. isosurface encloses the 60° C. isosurface (boundary between the black and dark grey zones) which in turn encloses the 70° C. isosurface (boundary between the dark grey and light grey zones) which in turn encloses the 80° C. isosurface (boundary between the light grey and white zones).

Figure 6F:
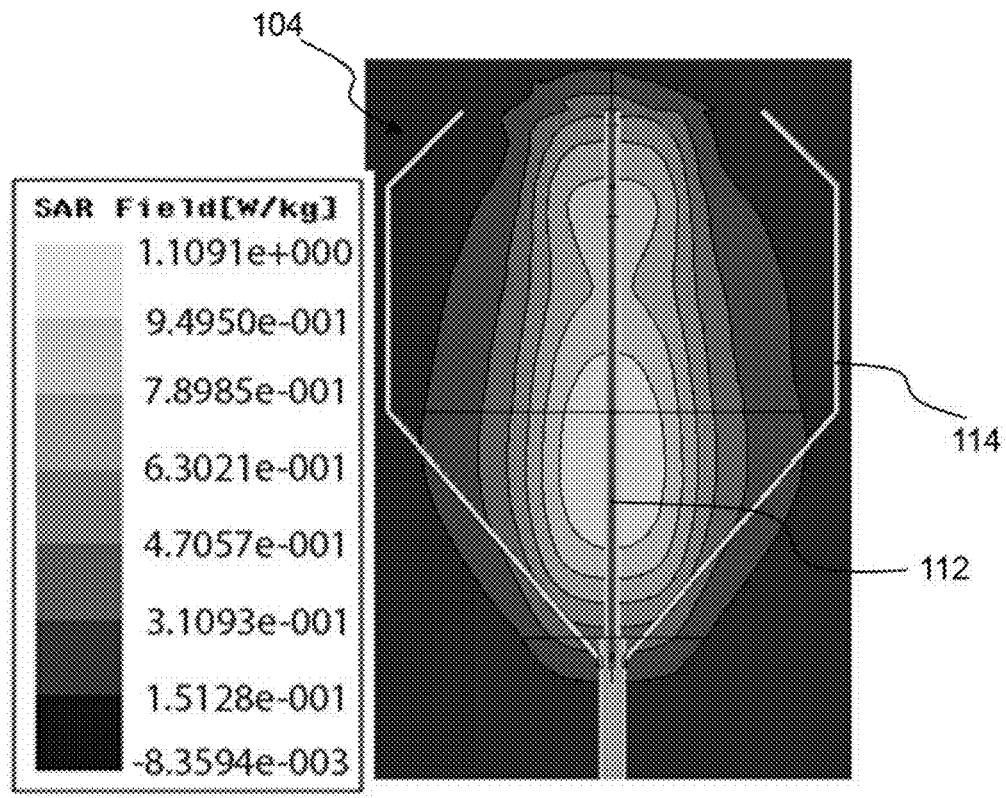
FIGS. 6F and 6G show a side view and a top view of a simulated SAR profile at 0.915 GHz of an embodiment of an antenna similar to the antenna of FIG. 6A.
Figure 6G:
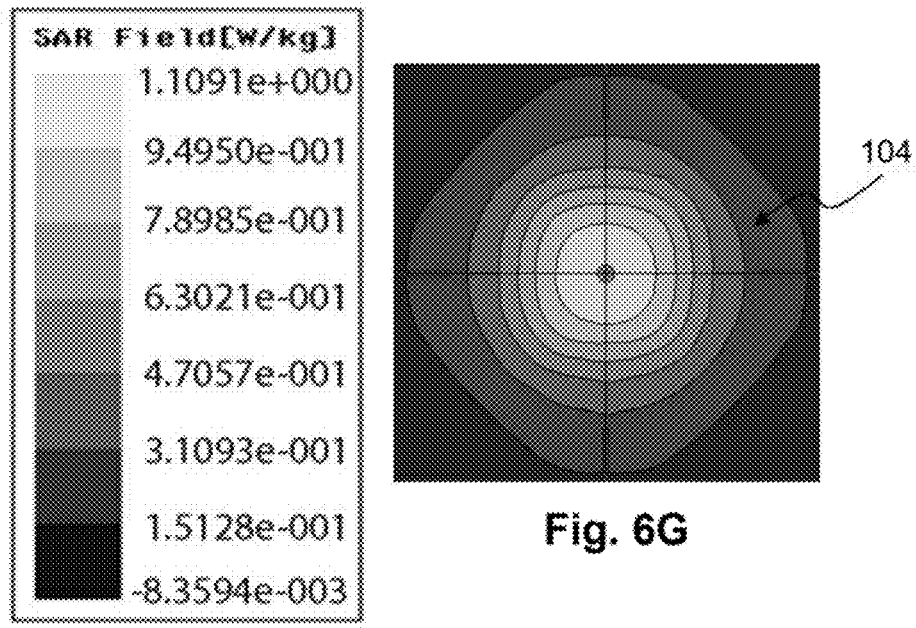

FIGS. 6F and 6G show a side view and a top view of a simulated SAR profile at 0.915 GHz of an embodiment of an antenna similar to the antenna of FIG. 6A. The SAR profile was simulated at 0.915 GHz using the Ansoft HFSS package to simulate an ablation in the liver. Radiating element 112 in FIGS. 6F and 6G is linear and has a length of about a quarter of the effective wavelength. FIGS. 6F and 6G illustrate that the volumetric lesion will be substantially confined to the extent of shaping elements 114.

The antenna 104 shown in FIGS. 6F and 6G comprises a substantially linear radiating element 112 with a plurality of shaping elements 114. The four shaping elements 114 shown in FIGS. 6F and 6G are identical and are arranged symmetrically around radiating element 112. Embodiments of antenna 104 may be designed with 1-10 shaping elements 114 arranged symmetrically or non-symmetrically arranged around radiating element 112. Shaping elements 114 may or may not be identical. In FIGS. 6F and 6G, each shaping element is elongate and comprises two bends or angled regions. Similar to the embodiment in FIG. 6A, each shaping element is electrically connected to the outer conductor of coaxial cable 102. The distal end of radiating element 112 and/or shaping elements 114 may comprise a sharp or penetrating tip. In one embodiment, shaping elements 114 are a retractable claw structure that extends from ablation device 100. In FIGS. 6F and 6G, shaping elements 114 enhance the electromagnetic field in the space between radiating element 112 and shaping elements 114. This creates a large, volumetric lesion between radiating element 112 and shaping elements 114. The volumetric lesion is substantially confined to the extent of shaping elements 114 as shown in FIGS. 6F and 6G. Further, shaping elements 114 reduce the leakage current that will otherwise be induced on the outer wall of the outer conductor of coaxial cable 102.

In FIGS. 6F and 6G, radiating element 112 comprises an elongate conductor that is about 34 mm long. The distal end of the elongate conductor is covered by a metallic tubular cap that is in conductive contact with the elongate conductor. The outer diameter of the conductive cap is about 0.8 mm and the length of the conductive cap is about 6 mm. The conductive cap is arranged such that the distance between the proximal end of the conductive cap and the distal end of the coaxial cable is about 28 mm. Entire radiating element 112 is covered with a layer of dielectric material. Each shaping element 114 comprises a proximal bend and a distal bend. The proximal bend is arranged at a longitudinal distance of about 15 mm measured along the length of the radiating element 112. The longitudinal distance between the proximal bend and the distal bend measured along the length of the radiating element 112 is about 15 mm. The longitudinal distance between the distal bend and the distal end of shaping element 114 measured along the length of the radiating element 112 is about 4 mm. Thus the total longitudinal length of each shaping element 114 measured along the length of radiating element 112 is about 34 mm. The total diameter of the structure formed by shaping elements 114 is about 30 mm. The use of antenna 104 in FIGS. 6F and 6G is similar to antenna 104 of FIG. 6A.

Figure 6H:
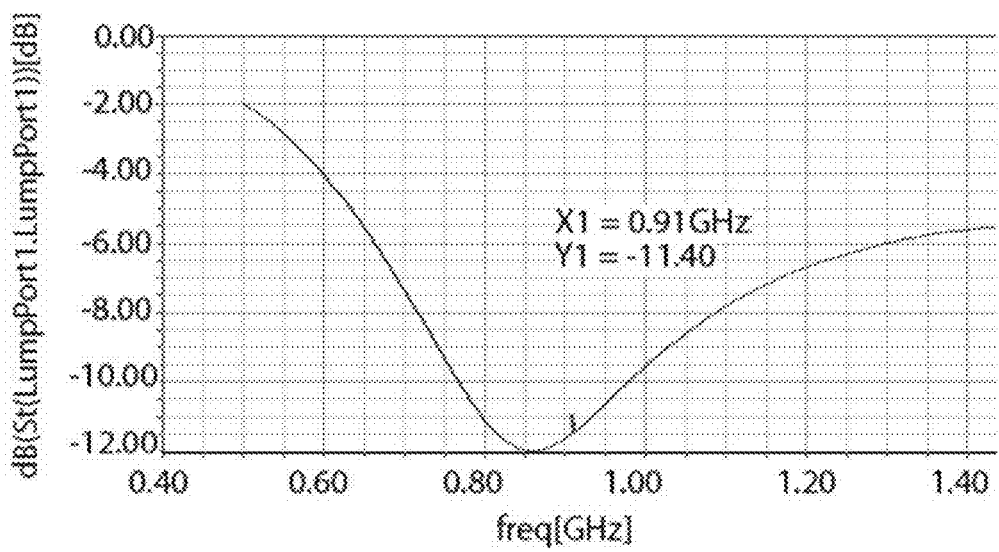
FIG. 6H shows the simulated return loss of an ablation device with an antenna of FIGS. 6F and 6G.

FIG. 6H shows the simulated return loss of an ablation device with an antenna of FIGS. 6F and 6G. The simulated return loss shows good matching (about −11.4 dB) at 0.915 GHz.

FIG. 7A shows an embodiment of a substantially linear antenna used to penetrate a bodily tissue and ablate a tumor. In FIG. 7A, antenna 104 is similar to antenna 104 of FIG. 1C with a helical radiating element 112 and a substantially linear shaping element 114. However, antenna 104 in FIG. 7A has a sufficient mechanical strength to penetrate tissue. Further, antenna 104 in FIG. 7A comprises a distal penetrating tip 134. The length of ablation device 100 may range from 5 cm to 60 cm. Ablation device 100 may be introduced through a surgical incision such as a laparotomy or a thoracotomy. Ablation device 100 may also be introduced through a surgical instrument port such as a port for laparoscopic or thoracoscopic instruments. Ablation device 100 may be introduced percutaneously by penetrating the skin using distal penetrating tip 134 and advancing antenna 104 into target tissue. Such percutaneous introduction may be used for example, to ablate liver or lung or uterine tumors with appropriate guidance such as radiological guidance or visual or endoscopic guidance. The low profile of antenna 104 enables antenna 104 to be introduced multiple times at different regions in the target tissue sequentially without causing excessive damage to healthy tissue. Multiple ablation devices 100 may also be introduced simultaneously in the target tissue to ablate a larger region of tissue.

Figure 8A:
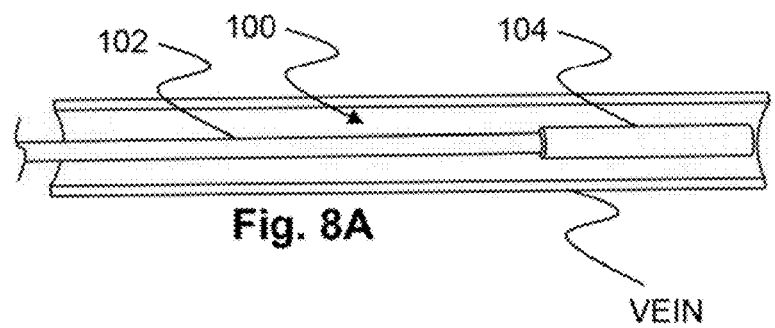
FIGS. 8A-8D show the steps of a method of minimally invasive treatment for treating venous reflux disease.
Figure 8B:
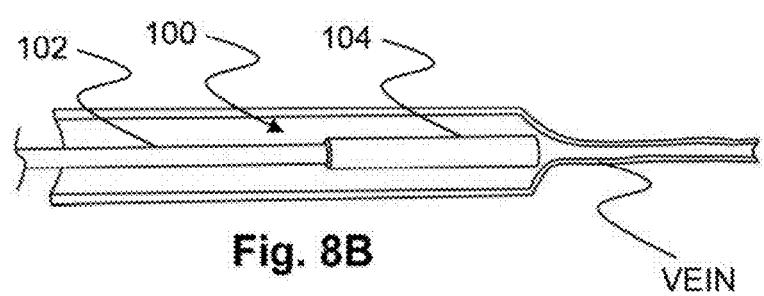
Figure 8C:
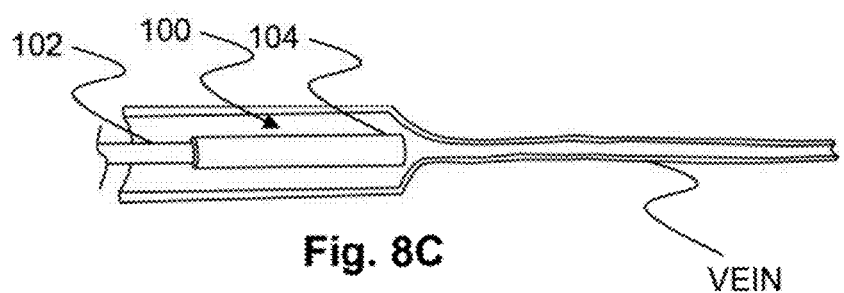
Figure 8D:
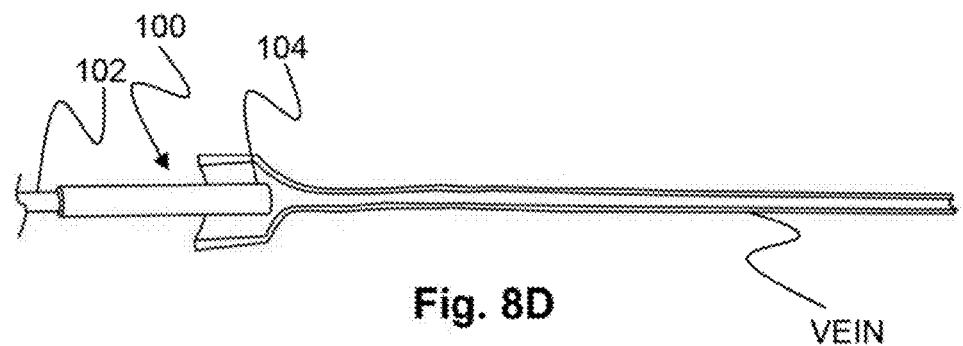

FIGS. 8A-8D show the steps of a method of minimally invasive treatment for treating venous reflux disease or varicose veins. In this method, a microwave device 100 is used to heat one or more regions of a target vein. In one embodiment, one or more regions of a target vein are heated to a temperature ranging between 80° C.-85° C. This temperature may be performed as an outpatient procedure to cause therapeutic fibrotic vein occlusion by controlled heating of the vein. The fibrotic vein occlusion may be caused by one or more of endothelial destruction, collagen contraction and vein wall thickening. In FIG. 8A, microwave device 100 is introduced into the target vein lumen through a small skin incision. Microwave device 100 is positioned at a distal region within the lumen of the target vein. The introduction and/or the navigation of microwave device 100 in the body may be guided using a suitable guidance modality. Examples of such modalities include, but are not limited to: ultrasound imaging (e.g. duplex ultrasound imaging), trans-illumination, fluoroscopic imaging and X-ray imaging. Once antenna 104 is positioned at the desired position, antenna 104 is used to deliver microwave energy to the target vein. Thereafter, in FIG. 8B, antenna 104 is positioned in the target vein at a position proximal to the position of FIG. 8A. Once antenna 104 is positioned at the desired position, antenna 104 is again used to deliver microwave energy to the target vein. The areas of the target vein that are treated in FIGS. 8A and 8B may overlap. This process is continued as shown in FIGS. 8C and 8D until the target vein is treated. The delivered microwave energy heats the vein and causes the vein to shrink. In one embodiment, microwave device 100 is delivered over a guidewire such as a 0.025" guidewire or a 0.035" guidewire or a 0.014" guidewire. Temperature sensing and/or impedance measurement at one or more locations on microwave device 100 and/or the target vein may be used to control the procedure. Such temperature sensing and/or impedance measurement may be used to adjust the power and/or time of microwave energy delivery. Although a substantially linear antenna 104 is depicted in FIGS. 8A-8D, any of the suitable antenna 104 embodiments disclosed herein may be used. For example, a helical antenna 104 in FIG. 3D may be used for this procedure. In one such embodiment, antenna 104 e.g. helical antenna 104 in FIG. 3D is collapsible to facilitate insertion through narrow openings and lumens and has a sufficient elasticity to regain its shape inside the target vein. In one embodiment, the diameter of antenna 104 is larger than the diameter of the vein lumen. This causes at least a portion of antenna 104 to come into physical contact with the wall of the target lumen. However, microwave energy delivery does not necessary need a perfect contact with target tissue. Hence embodiments of antenna 104 may be used wherein antenna 104 delivers microwave energy to a portion of the target vein even when antenna 104 does not contact that portion of the target vein.

Figure 9A:
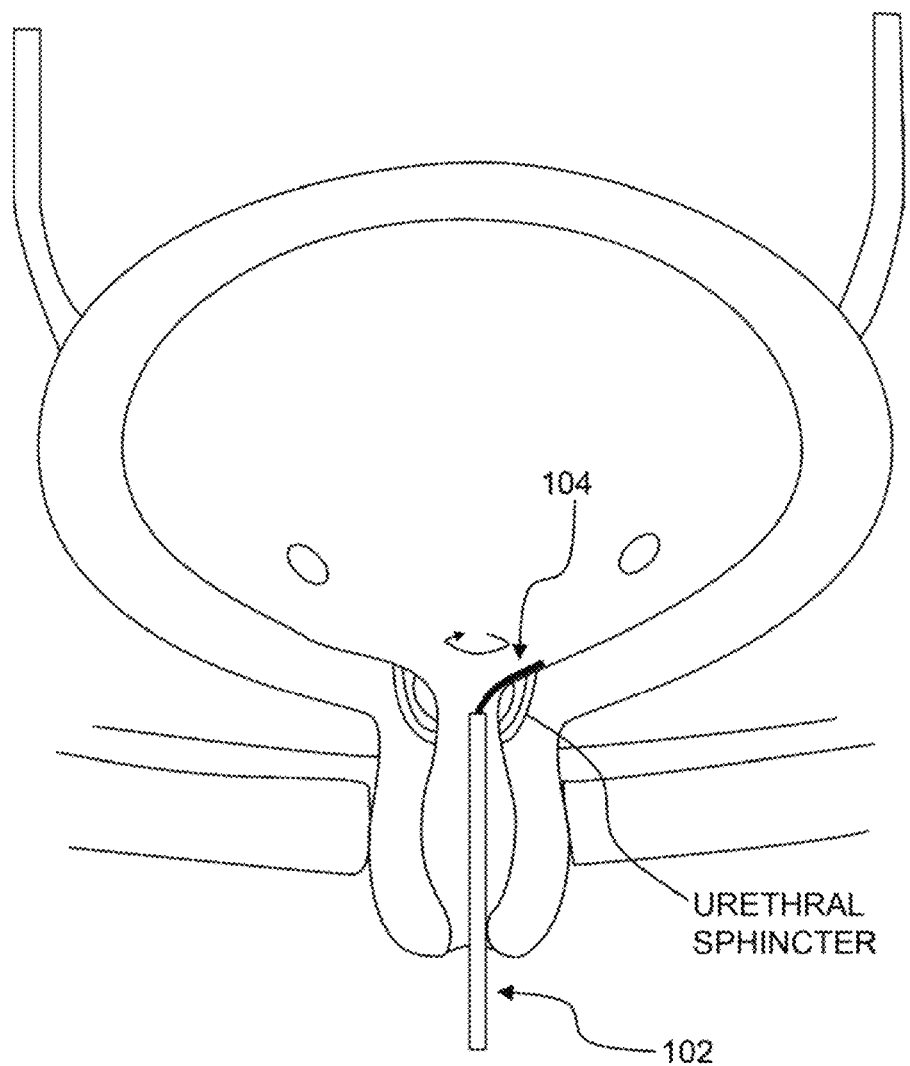
FIGS. 9A and 9B show a method of transurethral treatment of an internal urethral sphincter for treating stress urinary incontinence (SUI).
Figure 9B:
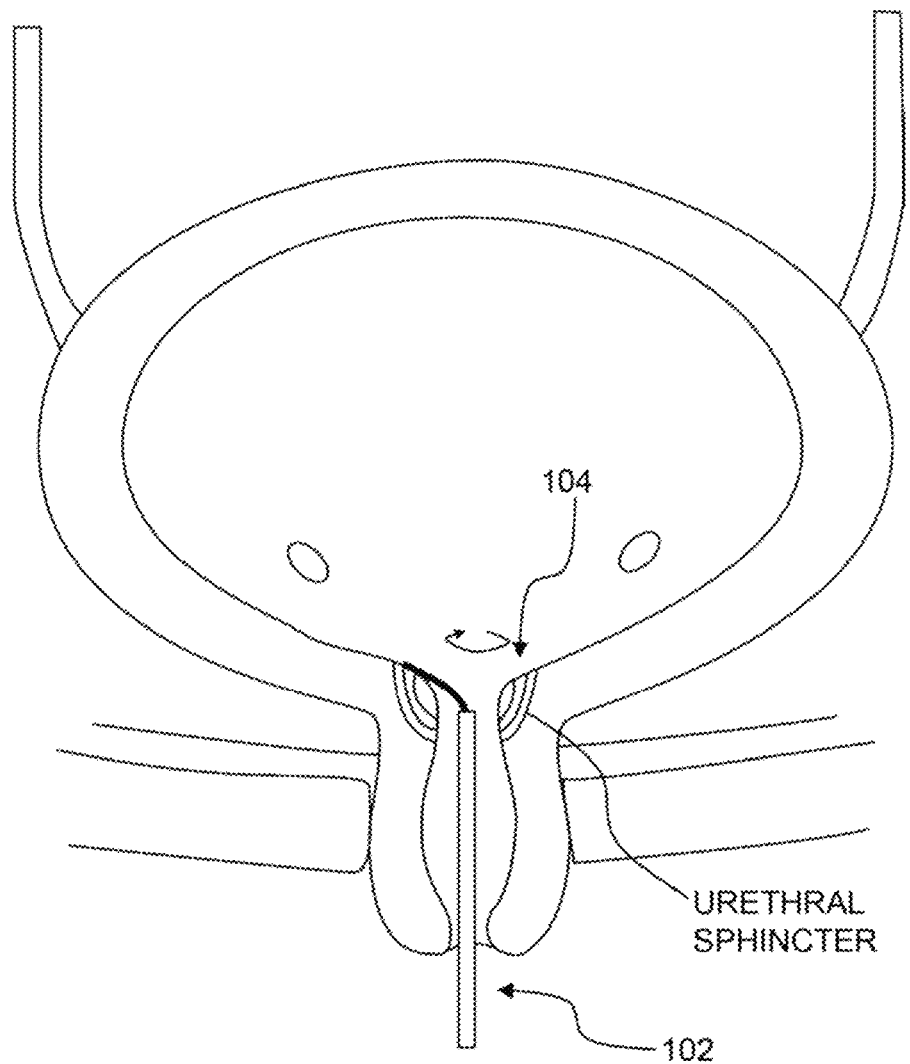

FIGS. 9A and 9B show a method of transurethral treatment of an internal urethral sphincter for treating stress urinary incontinence (SUI). In FIG. 9A, microwave energy is delivered to the internal urethral sphincter to achieve therapeutic collagen denaturation. In FIG. 9A, a microwave device 100 comprising an antenna 104 is introduced via a trans-urethral approach into the urinary system. Any suitable antenna 104 design disclosed herein may be used for the embodiment in FIGS. 9A and 9B. In one embodiment, antenna 104 is a monopole antenna with or without any shaping element 114. Antenna 104 is positioned such that it is in the vicinity of the internal urethral sphincter as shown in FIG. 9A. Antenna 104 may comprise a steering or deflecting modality to change the orientation of antenna 104 relative to coaxial cable 102. In one embodiment, antenna 104 is introduced through a sheath comprising a steering or deflecting modality such as one or more pull wires. This steering or deflecting modality may be used to position antenna 104 at various points in the urinary system to deliver microwave energy to internal urinary sphincter. Microwave device 100 may comprise a bent region such that antenna 104 is oriented at an angle relative to coaxial cable 102. Also, microwave device 100 may be twisted as shown in FIG. 9B and/or advanced distally and/or withdrawn proximally to further position antenna 104 at various points in the urinary system to deliver microwave energy to internal urinary sphincter. In an alternate embodiment, antenna 104 is positioned substantially at the center of a lumen or a passage of the urinary system and is used to treat the desired target tissue without direct physical contact of antenna 104 with the target tissue. In such embodiments, the desired clinical effect may be obtained by delivering microwave energy only once with antenna 104 at a first position and thereafter re-delivering microwave energy with antenna 104 at a second position. Antenna 104 is used to transmit controlled microwave energy to create controlled heating in one or more regions of the internal urinary sphincter. In one embodiment, this heating is carried out at a lower temperature such that there is minimal or no cell death in the internal urinary sphincter. The heating denatures collagen in the internal urinary sphincter. This denaturation may be carried out at multiple sites by re-positioning antenna 104 or may be carried out without re-positioning antenna 104. The collagen denaturation may be used to create firmer tissue that has an increased resistance to the effects of heightened intra-abdominal pressure, which in turn reduces or eliminates SUI episodes. Any of the methods and devices disclosed herein may be used along with a surface cooling modality to cool the surface of a tissue that is being treated. This allows the surface of the tissue to remain relatively unchanged while microwave energy is delivered to create a desired therapeutic effect in deeper regions of the tissue. For example, in FIG. 9A, a surface cooling modality may be used to protect the surface of the lumen of the urinary tract while delivering microwave energy to deeper tissues such as the internal urinary sphincter.

In FIG. 9A, the method can be performed under local anesthesia in an outpatient or office setting. Such methods are especially useful for treating SUI due to hypermobility in women who have failed conservative care and who do not desire or are not eligible for surgical therapy.

Since the devices disclosed herein may be designed as low-profile (less than 6 F), flexible devices, the devices may be used for treating SUI in both male as well as female patients. Rigid and larger profile devices for collagen denaturation in the prior art are restricted to use in women because of their short and relatively straight urethra. However, the use of such prior art devices in male patients is difficult because the male urethra is longer and much less straight.

Methods similar to those shown in FIGS. 9A and 9B that involve the delivery of microwave energy to cause controlled heating of tissue may also be used to treat other disorders of anatomical lumens. Examples of such disorders of anatomical lumens include, but are not limited to: gastroesophageal reflux disease and fecal incontinence. In one embodiment, a device or method disclosed herein may be used for deeper tissue heating to cause tissue shrinkage for treating conditions such as fecal incontinence, GERD, urinary incontinence, etc. Such deeper heating may be carried out with the device placed within the lumens or other bodily cavities.

Figure 9C:
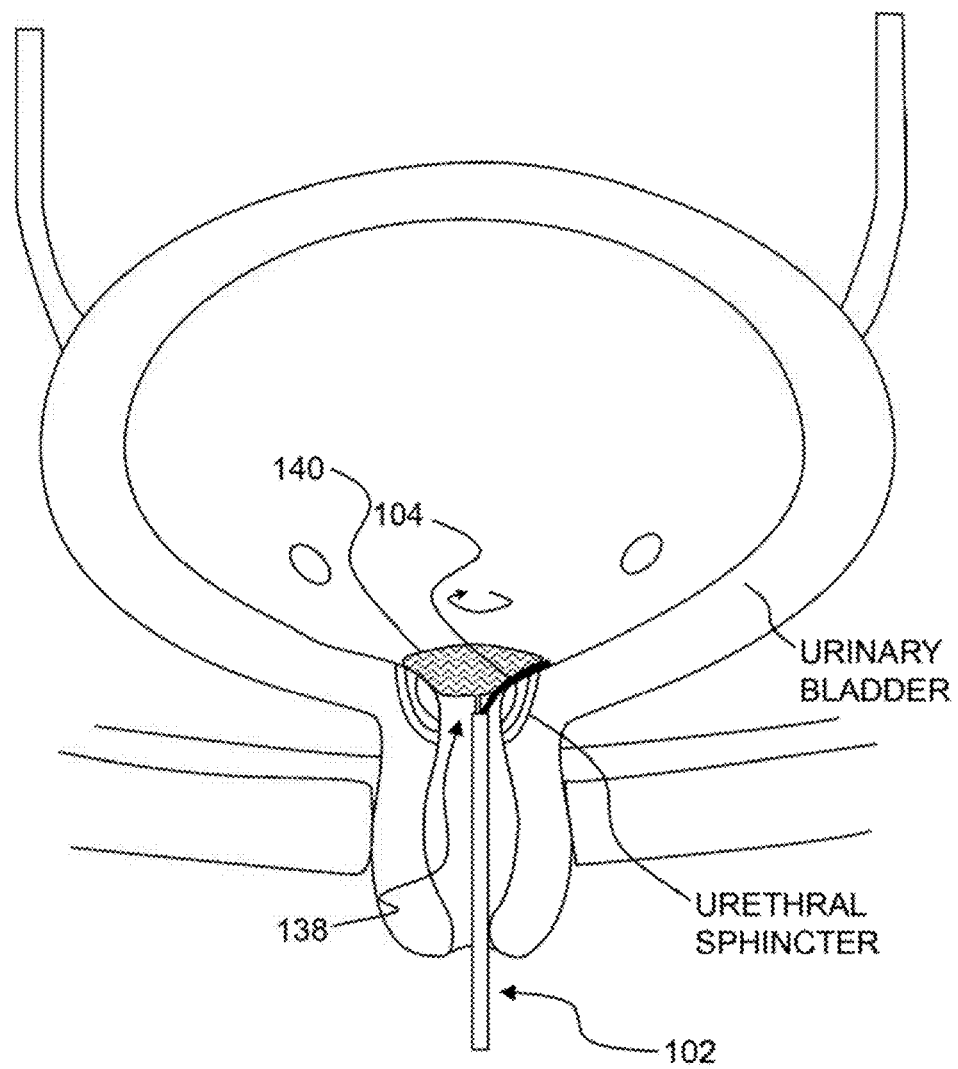
FIG. 9C shows a method embodiment of transurethral treatment of an internal urethral sphincter for treating stress urinary incontinence (SUI) by an energy delivery device cooperating with a positioning element.

FIG. 9C shows a method embodiment of transurethral treatment of an internal urethral sphincter for treating stress urinary incontinence (SUI) by an energy delivery device cooperating with a positioning element. In FIG. 9C, antenna 104 is similar to antenna 104 in FIGS. 9A and 9B. The shaft of microwave device 100 comprises a microwave transmission line such as a coaxial cable 102 and a lumen through which one or more device or fluids may be passed. In FIG. 9C, microwave device 100 is introduced by a trans-urethral approach into the urinary tract such that antenna 104 is positioned in the vicinity of the internal urethral sphincter. Thereafter, a positioning device 138 is passed through the lumen of shaft 102. Thereafter, a positioning element 140 located at the distal region of positioning device 138 is deployed in the urinary bladder. In the embodiment shown in FIG. 9C, positioning element 140 in its deployed configuration has a width that is greater than the width of the urethra but less than the width of the urinary bladder such that positioning element 140 in its deployed configuration is lodged in the urinary bladder. Thereafter, positioning device 138 is pulled in the proximal direction such that positioning element 140 is positioned against the internal urethral orifice. Thus, by feeling the forces experiences when positioning device 138 is pulled, the location of the internal urethral orifice can be easily determined without using any imaging modality. Positioning element 140 positioned against the internal urethral orifice is then used to position antenna 104 accurately at the desired position. In one embodiment, antenna 104 is located between tissue and positioning element 140. In this embodiment, positioning element 140 may be used to press antenna 104 against tissue. Positioning element 140 may comprise a cooling modality to cool the surface of tissue. Positioning element 140 is controllably deployable from a collapsed, low-profile configuration to a deployed, larger-profile configuration. Thus positioning element 140 may be a non-compliant, semi-compliant or a compliant balloon, an umbrella-like structure, elastic or super-elastic or shape memory structures, structure comprising one or more bendable splines, etc. Antenna 104 may be repositioned if necessary to delivery energy to multiple sites in the target tissue. After a procedure is completed, positioning element is converted to a collapsed, low-profile configuration and microwave device 100 and positioning device 138 are both removed from the anatomy.

Figure 9D:
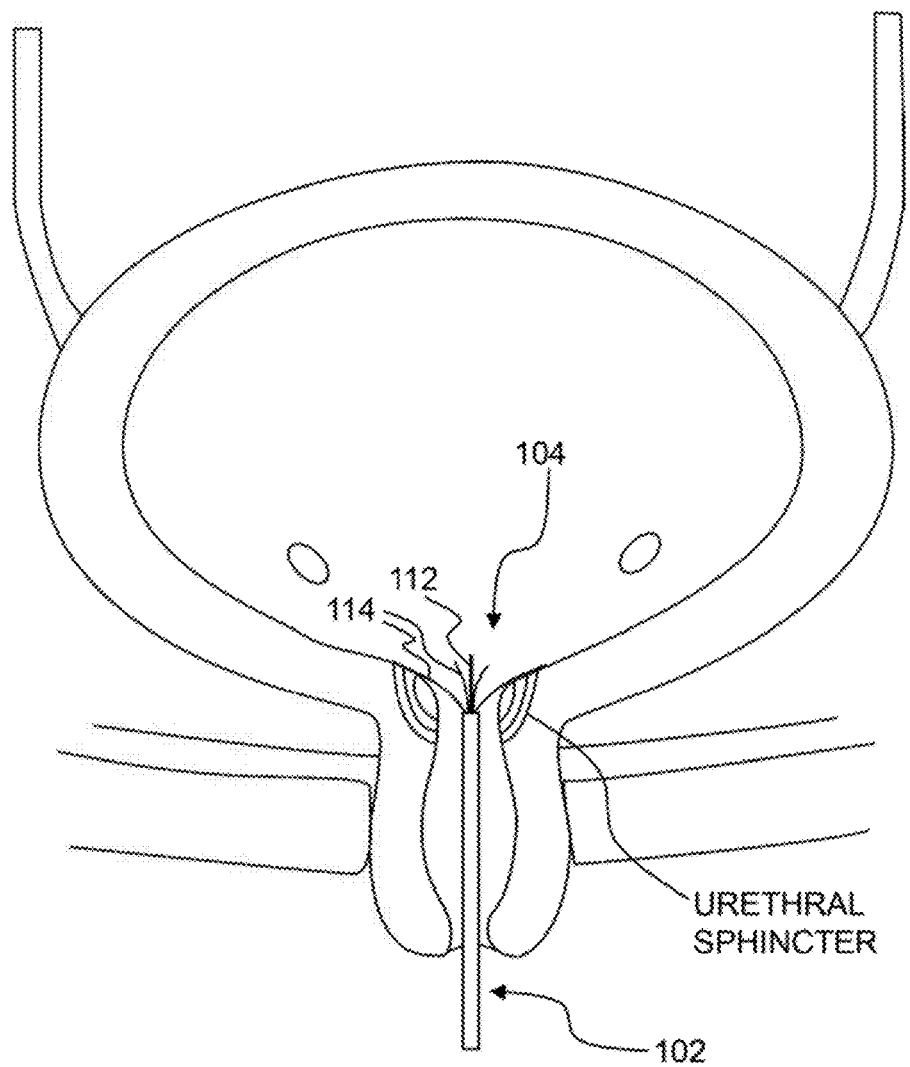
FIG. 9D shows a method embodiment of transurethral treatment of an internal urethral sphincter for treating stress urinary incontinence (SUI) by an energy delivery device with an antenna that simultaneously delivers energy to a larger volume of tissue.

FIG. 9D shows a method embodiment of transurethral treatment of an internal urethral sphincter for treating stress urinary incontinence (SUI) by an energy delivery device with an antenna that simultaneously delivers energy to a larger volume of tissue. In FIG. 9D, antenna 104 comprises a radiating element 112 and one or more shaping elements 114. In one embodiment, antenna 104 is used to generate a microwave field that envelopes a majority of the internal urethral sphincter. Although antenna 104 may be repositioned if necessary after a first energy delivery, in this embodiment, antenna 104 is designed to create the desired clinical effect through energy delivery from a single site.

Figure 10A:
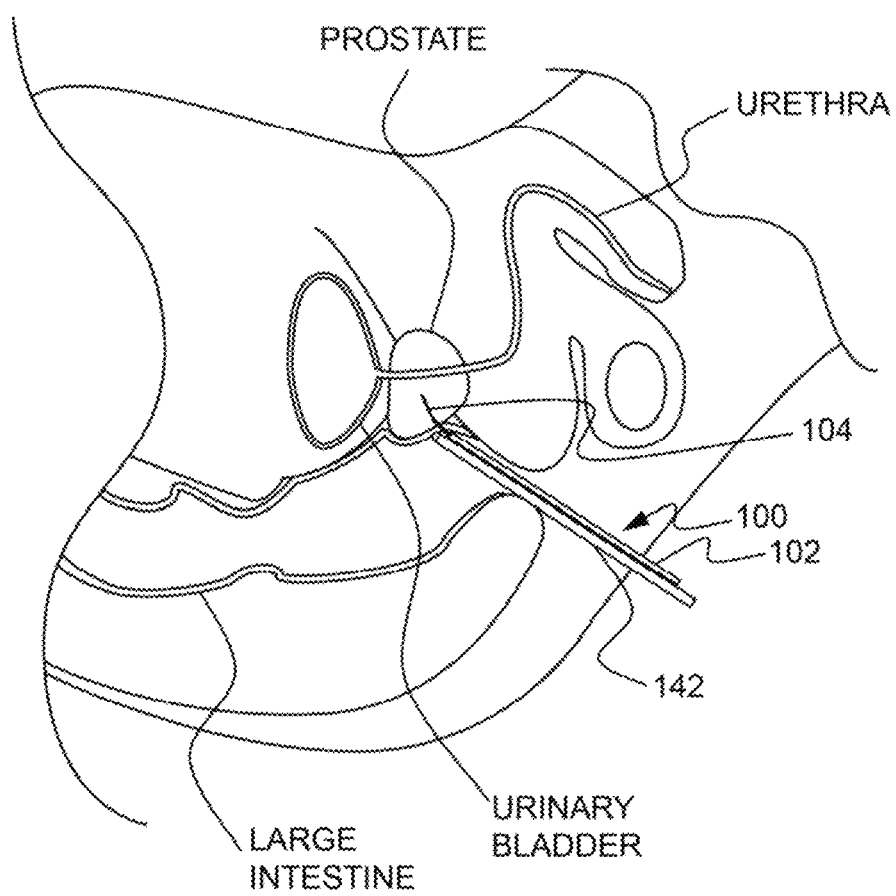
FIG. 10A shows an embodiment of a method for treating Benign Prostatic Hyperplasia (BPH) by an energy delivering device.

FIG. 10A shows an embodiment of a method for treating Benign Prostatic Hyperplasia (BPH) by an energy delivering device. BPH is a benign enlargement of the prostate i.e. an increase in size of the prostate seen in middle-aged and elderly men. The enlarged prostate compresses the urethral canal and causes partial, or sometimes virtually complete, obstruction of the urethra. This in turn interferes with the normal flow of urine. Thus BPH may lead to symptoms of urinary hesitancy, frequent urination, increased risk of urinary tract infections and urinary retention. BPH may be treated by reducing the volume of the prostate. FIG. 10A illustrates a method of ablating prostate tissue to reduce the volume of the prostate. In FIG. 10A, a trans-rectal ultrasound probe 142 is used to visualize the anatomy and/or a microwave device 100. Antenna 104 of microwave device 100 is inserted into prostate tissue through the wall of the rectum. The distal end of microwave device 100 may comprise a cutting or penetrating edge. The BPH treatment procedure may be similar to a trans-rectal prostate biopsy procedure by replacing the biopsy device such as a biopsy needle with microwave device 100.

In one method embodiment, the rectal area is cleaned and a numbing gel is applied. Thereafter, a thin ultrasound probe 142 is inserted into the rectum. In one embodiment, ultrasound probe 142 comprises a 5.0 to 7.5 MHz transducer. Trans-rectal ultrasonography is then used to image the prostate. The ultrasonography is used to identify one or more of: the site of penetration of microwave device 100, the one or more areas that need to be anesthetized with an anesthetic injection and the one or more sites of ablation. Trans-rectal ultrasonography is thereafter used to guide antenna 104 to a first desired location. Thereafter, ablation energy is delivered by antenna 104. A single area or multiple areas of the prostate may be ablated by repositioning antenna 104 and delivering microwave energy. The protocol for deciding the number and location of prostate areas to be ablated may be similar to protocol for deciding the number and location of prostate areas for prostate needle biopsy. For example, protocols similar to five-region, eight systematic core template and the 11-multisite biopsy protocols may be used for ablating the prostate.

Antenna 104 in FIG. 10A may comprise a radiating element 112 and one or more shaping elements 114. Alternately, one or more shaping elements 114 may be introduced through a separate device or a separate introduction path to shape the microwave energy profile generated by antenna 104. In one such embodiment, antenna 104 comprises a radiating element 112 and is introduced trans-rectally into the prostate while one or more shaping elements 114 are introduced in the urethral lumen. In another such embodiment, antenna 104 comprises a radiating element 112 and is introduced trans-rectally or trans-urethrally into the prostate while one or more shaping elements 114 are located on a separate device that is introduced trans-rectally into the prostate. Microwave device 100 may be mechanically coupled to ultrasound probe 142 or may be mechanically independent from ultrasound probe 142.

In alternate method embodiments, one or more regions of the prostate may be accessed through the urethra, or through the space between the anus and scrotum (perineum).

Figure 10B:
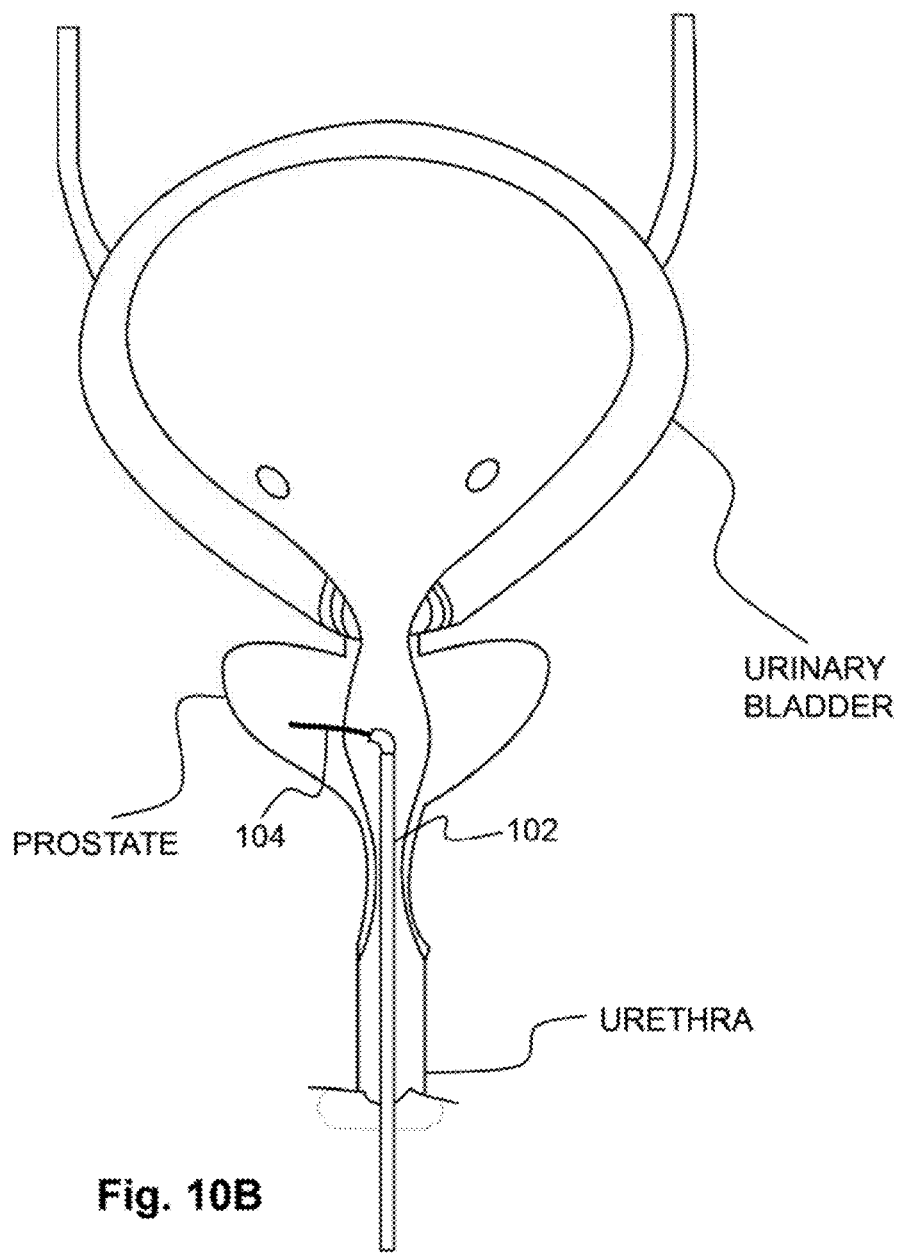
FIG. 10B shows an embodiment of a method for treating Benign Prostatic Hyperplasia (BPH) by an energy delivering device inserted through the urethral lumen.

FIG. 10B shows an embodiment of a method for treating Benign Prostatic Hyperplasia (BPH) by an energy delivering device inserted through the urethral lumen. FIG. 10B illustrates a method of ablating prostate tissue to reduce the volume of the prostate. In FIG. 10B, a trans-rectal ultrasound probe may be used to visualize the anatomy and/or a microwave device 100. Antenna 104 of microwave device 100 is inserted into prostate tissue through the wall of the urethra. The distal end of microwave device 100 may comprise a cutting or penetrating edge. One or more regions of microwave device 100 may be bent or curved or may be controllably deflectable to facilitate insertion of antenna 104 into prostate tissue.

In one method embodiment, ultrasonography may be used to identify one or more of: the site of penetration of microwave device 100, the one or more areas that need to be anesthetized with an anesthetic injection and the one or more sites of ablation. An imaging modality such as trans-rectal ultrasonography, cystoscopy or fluoroscopy may be used to guide antenna 104 at a first desired location. Thereafter, ablation energy is delivered by antenna 104. A single area or multiple areas of the prostate may be ablated by repositioning antenna 104 and delivering microwave energy.

Antenna 104 in FIG. 10B may comprise a radiating element 112 and one or more shaping elements 114. Alternately, one or more shaping elements 114 are introduced through a separate device or a separate introduction path to shape the microwave energy profile generated by antenna 104. In one such embodiment, antenna 104 comprises a radiating element 112 and is introduced trans-urethrally into the prostate while one or more shaping elements 114 are introduced trans-rectally. In another such embodiment, antenna 104 comprises a radiating element 112 and is introduced trans-urethrally into the prostate while one or more shaping elements 114 are located on a separate device that is introduced trans-urethrally into the prostate.

Figure 10C:
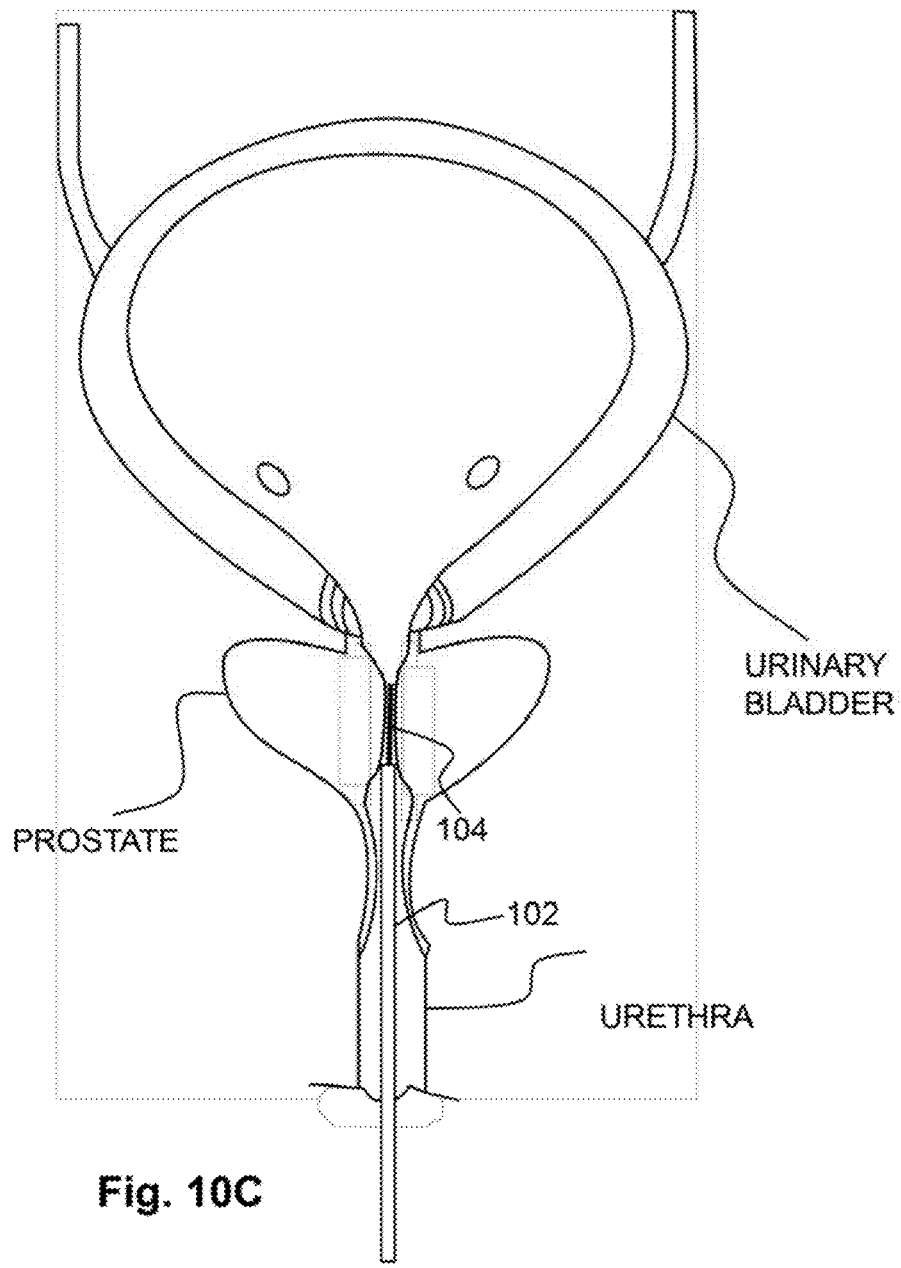
FIG. 10C shows an embodiment of a method for treating Benign Prostatic Hyperplasia (BPH) by an energy delivering device inserted in the urethral lumen.

FIG. 10C shows an embodiment of a method for treating Benign Prostatic Hyperplasia (BPH) by an energy delivering device inserted in the urethral lumen. FIG. 10C illustrates a method of ablating prostate tissue to reduce the volume of the prostate. In FIG. 10C, suction is applied inside the lumen of the urethra to collapse the urethra around antenna 104. Thus, the urethral lumen wall comes into contact with or comes in the vicinity of antenna 104. Thereafter, microwave energy is delivered by antenna 104 to achieve the desired therapeutic outcome. Thus, the method is non-invasive. In FIG. 10C, antenna 104 may be introduced under cystoscopic guidance either through a cystoscopic sheath or simple co-introduced along with a cystoscope. In FIG. 10C, a trans-rectal ultrasound probe may be used to visualize the anatomy and/or a microwave device 100. In one embodiment, microwave device 100 is positioned at a single location inside the prostatic urethra and microwave energy delivery is carried out from this single location. Alternately, antenna 104 may be repositioned one or more times inside the prostatic urethra. One or more regions of microwave device 100 may be bent or curved or may be controllably deflectable.

Figure 11A:
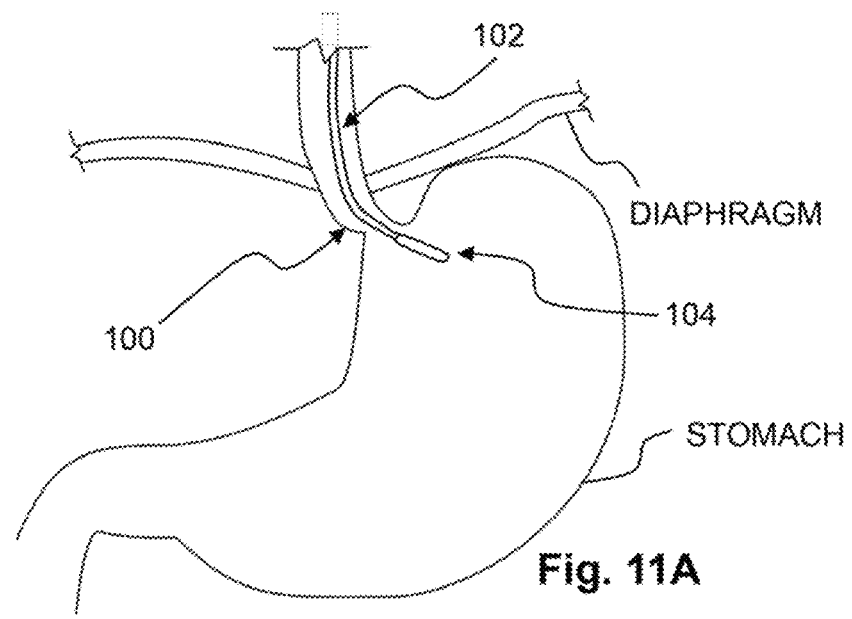
FIGS. 11A-11C illustrate the use of a microwave device with a steerable or deflectable antenna used to treat Gastroesophageal Reflux Disease (GERD).
Figure 11B:
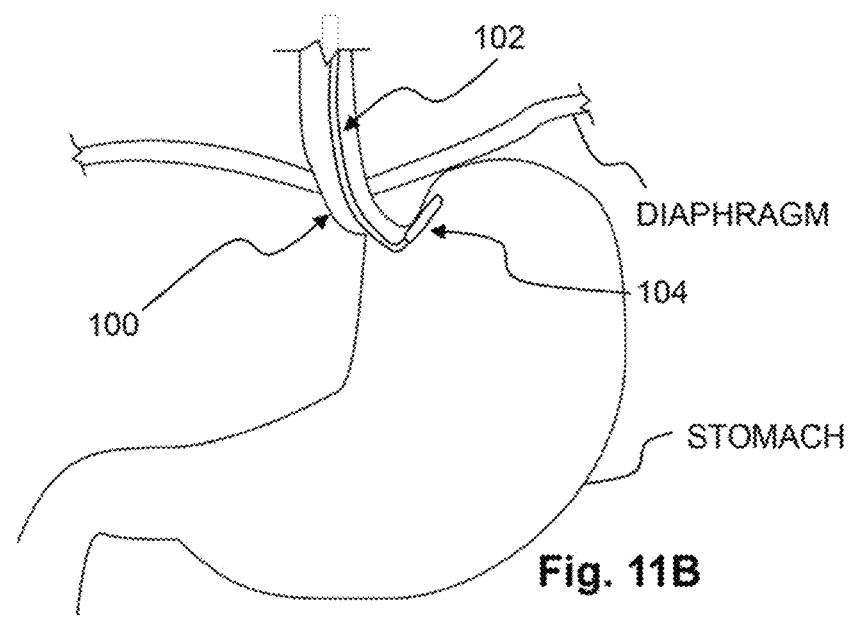
Figure 11C:
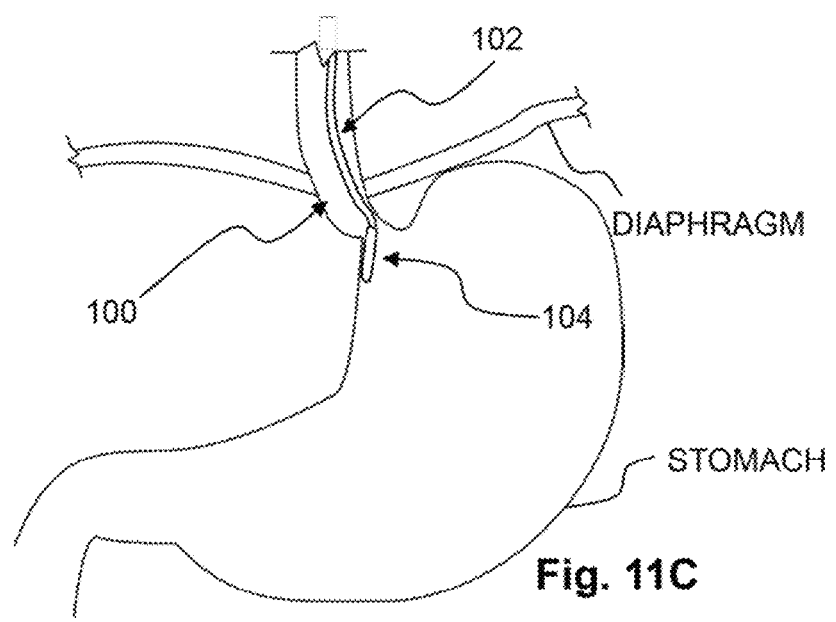

FIGS. 11A-11C illustrate the use of a microwave device with a steerable or deflectable antenna used to treat Gastroesophageal Reflux Disease (GERD). In FIGS. 11A-11C, the orientation of antenna 104 relative to the orientation of the distal region of coaxial cable 102 can be changed by engaging a steering or deflecting mechanism located on microwave device 100 or on a sheath that encloses microwave device 100. This steering or deflecting mechanism (e.g. one or more pull wires) may be used to position antenna 104 at various points in the digestive system to deliver microwave energy to the smooth muscle of the gastroesophageal junction. In FIG. 11A, a microwave device 100 e.g. a microwave catheter comprising an antenna 104 is introduced via a trans-esophageal approach into the stomach. Any suitable antenna 104 design disclosed herein may be used for the embodiment in FIG. 11A. In one embodiment, antenna 104 is a monopole antenna with or without any shaping element 114. In another embodiment, antenna 104 of FIG. 11A is similar to antenna 104 of FIG. 1C. Microwave device 100 may be introduced into the stomach under endoscopic guidance with the patient under conscious sedation. Antenna 104 is positioned such that it is in the vicinity of the smooth muscle of the gastroesophageal junction as shown in FIG. 11A. Also, microwave device 100 may be rotated and/or advanced distally and/or withdrawn proximally to further position antenna 104 at various points in the digestive system to deliver microwave energy to the smooth muscle of the gastroesophageal junction. Antenna 104 is used to transmit controlled microwave energy to create thermal lesions below the mucosa at the gastroesophageal junction. This in turn may be used to create one or more of the following clinical effects: controlling reflux by inhibiting transient, inappropriate lower esophageal sphincter (LES) relaxation, increasing postprandial LES pressure and decreasing LES compliance. A surface cooling modality may be used to protect the surface of the mucosa of the gastrointestinal tract while delivering microwave energy to deeper tissues such as the LES.

In FIG. 11B, antenna 104 is moved to a second location in the vicinity of the smooth muscle of the gastroesophageal junction in the greater curvature of the stomach. This may be done by one or more of: engaging a steering or deflecting mechanism on microwave device 100 or on a sheath that encloses microwave device 100, rotating microwave device 100, advancing microwave device 100 distally and withdrawing microwave device 100 proximally. In FIG. 11C, antenna 104 is moved to a third location in the vicinity of the smooth muscle of the gastroesophageal junction in the lesser curvature of the stomach. This may be done by one or more of: engaging a steering or deflecting mechanism on microwave device 100 or on a sheath that encloses microwave device 100, rotating microwave device 100, advancing microwave device 100 and withdrawing microwave device 100 proximally. Thus, antenna 104 may be used to treat multiple locations in the gastrointestinal tract to treat GERD.

Figure 12A:
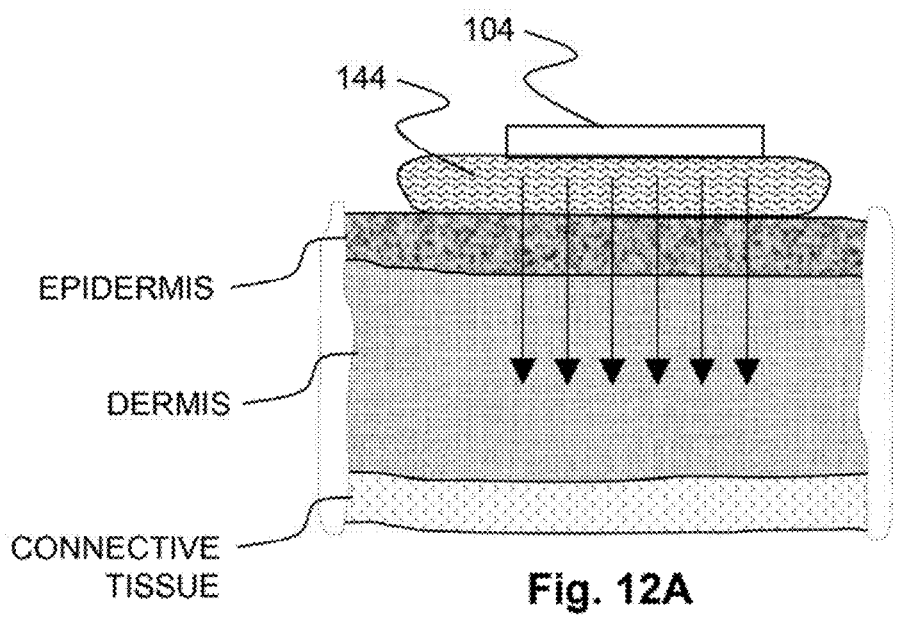
FIG. 12A shows a method embodiment of using an antenna along with a surface cooling modality to improve the cosmetic appearance of skin.

FIG. 12A shows a method embodiment of using an antenna along with a surface cooling modality to improve the cosmetic appearance of skin. In FIG. 12A, an antenna 104 delivers microwave energy to the skin to heat one or more skin layers. This heating may be carried out at a lower temperature such that there is minimal or no cell death. In the embodiment shown in FIG. 12A, antenna 104 does not directly contact the skin. Various designs of antennas 104 disclosed herein may be used to the method in FIG. 12A. The antennas 104 may have a suitable cross section tailored for a particular application. For example, antennas 104 may be designed with a cross sectional areas ranging from 0.5 sq. cm to 9 sq. cm. The antenna 104 may be linear such as shown in FIG. 1C or may be in a bent or curved configuration such as shown in FIG. 3 series. Any suitable frequency of microwave energy may be used for this application and any other applications disclosed herein. A surface cooling modality 144 is used to cool the surface of the skin to prevent undesired damage to the superficial skin layers. Examples of suitable surface cooling modalities 144 include, but are not limited to: inflatable structures inflated with a cooling fluid, gels or other conformable structures and structures designed to circulate one or more fluids on the skin surface. In one embodiment, surface cooling modality 144 does not interfere with the passage of microwave energy. Thus, surface cooling modality 144 may be an inflatable balloon inflated with a circulating, non-polar cooling fluid. Antenna 104 may be used for volumetric heating of deeper layers of the skin while protecting the epidermis. This may be used to non-invasively create one or more of the following effects: smoothening skin, tightening skin and contouring skin. This method may also be used to reduce the appearance of cellulite. This method may also be used to reduce skin dimpling for the thigh and buttock areas. In one embodiment, microwave energy is used to heat the dermis and subcutaneous tissue to cause contraction of collagen fibrils. This may be followed by secondary collagen synthesis and remodeling to achieve the desired cosmetic effect. A compression garment may be worn by the patient after the treatment. The treatment may be carried out in a single treatment session or in multiple treatment sessions. In each treatment session, a surface of the skin may be treated by delivering microwave energy in multiple staggered passes, multiple non-staggered passes or in a single pass.

Various antenna embodiments disclosed herein may be used to build ablation catheters for treating a variety of electrophysiological conditions (e.g. atrial fibrillation, Ventricular Tachycardia, Bradycardia, flutter and other arrhythmias) and for treating heart structures including, but not limited to walls of the atria or the ventricles, valves and the regions surrounding the valves to treat non-electrophysiological conditions. Antenna 104 may be used to create a series of ablations in the left atrium to treat atrial fibrillation. Antenna 104 may be used to create long and transmural lesions in the left atrium. The lesions in the left atrium may be used to imitate a Maze procedure. Antenna 104 may be positioned at various locations around the pulmonary vein and used to ablate various locations around the pulmonary vein for electrophysiological isolation of the pulmonary vein.

Figure 13A:
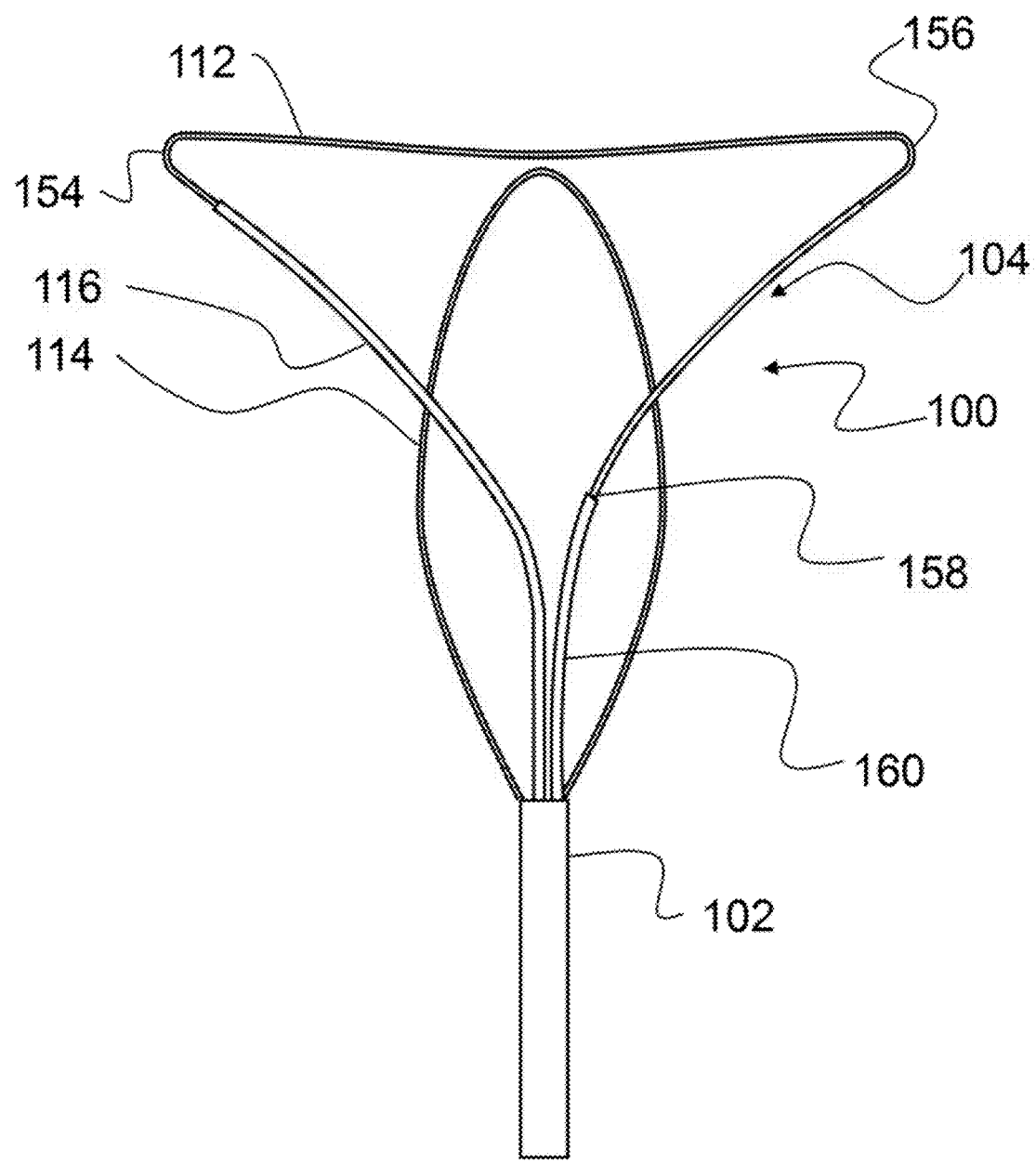
FIG. 13A shows a view of an antenna of a microwave ablation device optimized for endometrial ablation.

Several embodiments of planar antennas 104 are also included in the scope of the invention. Such planar antennas 104 may be used to ablate or otherwise treat planar or non-planar tissue regions. Such planar antennas 104 may comprise single or multiple splines, curves or loops in a generally planar arrangement. Planar antennas 104 may be used for ablating a surface such as the surface of organs such as liver, stomach, esophagus, etc. For example, FIG. 13A shows a view of a planar antenna of a microwave ablation device designed for endometrial ablation. In FIG. 13A, microwave ablation device 100 comprises a transmission line (such as a coaxial cable 102) terminating in an antenna 104 at the distal end of the transmission line. In one embodiment, a single microwave signal is fed to antenna 104 through coaxial cable 102. Antenna 104 generates a microwave field. The near field of the microwave field generated by antenna 104 is used for endometrial ablation. In FIG. 13A, antenna 104 comprises a radiating element in the form of an outer loop 112 and a shaping element in the form of a metallic center loop 114. Outer loop 112 and center loop 114 may touch each other when deployed in the anatomy. In one embodiment, outer loop 112 is a continuation of the inner conductor of coaxial cable 102. Center loop 114 shapes or redistributes the microwave field radiated by outer loop 112. It should be noted that there is no direct electrical conduction between outer loop 112 and center loop 114. When microwave energy is delivered through coaxial cable 102 to antenna 104, a first microwave field is emitted by outer loop 112. The first microwave field interacts with center loop 114. This interaction induces a leakage current on center loop 114. The leakage current in turn creates a second microwave field. The first microwave field and the second microwave field together combine to produce a unique shaped microwave field of antenna 104 that is clinically more useful that the unshaped microwave field generated by an antenna 104 comprising only outer loop 112. Thus the original microwave field is redistributed by the design of center loop 114. Center loop 114 alone is not capable of functioning as an antenna; rather center loop 114 shapes or redistributes the electromagnetic or microwave field emitted by outer loop 112 to produce a shaped microwave field that is clinically more useful. Further, the combination of outer loop 112 and center loop 114 improves the power deposition of antenna 104.

In one embodiment, outer loop 112 has no sharp corners. Sharp corners in outer loop 112 may cause the field to concentrate in the vicinity of the sharp corners. In one embodiment, the minimal radius of curvature of a corner in outer loop 112 is at least 0.5 mm. In the embodiment in FIG. 13A, the radius of curvature of corner regions 154 and 156 in outer loop 112 is about 1 mm+/−0.3 mm.

In one embodiment, antenna 104 has a shape that substantially approximates the shape of the body organ to be ablated. For example, antenna in FIG. 13A has a roughly triangular shape that approximates the shape of the uterine cavity and is especially suited for endometrial ablation. The proximal portion of the antenna 104 is directed towards the cervix and corner regions 154 and 156 of outer loop 112 are directed towards the fallopian tubes. However, as mentioned before, microwave thermal ablation does not necessarily require perfect contact with all of the target tissue. Thus antenna 104 is able to ablate all or substantially all of the endometrium. The entire endometrium can be ablated in a single ablation by antenna 104 having a single microwave antenna. Thus, repositioning of antenna 104 after an ablation is not needed. This greatly reduces the amount of physician skill needed for the procedure. Further, multiple antennas 104 are not needed in ablation device 100. A single antenna 104 positioned at a single location is able to ablate a therapeutically sufficient amount of the endometrium. This simplifies the design of ablation device 100.

Further, antenna 104 in the working configuration is generally flat and flexible. The plane of outer loop 112 is substantially parallel to the plane of center loop 114. Thus, the uterine walls experience only slight forces from antenna 104. This in turn reduces or eliminates the distension of the uterine wall thereby reducing the discomfort to the patient. This in turn further reduces the anesthesia requirements. Flexible antenna 104 may easily be introduced in a collapsed configuration through a small lumen thereby eliminating or minimizing any cervical dilation. This dramatically reduces the discomfort to the patient consequently significantly reducing the requirement of anesthesia. This has tremendous clinical advantages since now the procedure can be performed in the physician's office under local anesthesia.

Further, flat and flexible antenna 104 in FIG. 13A in its deployed configuration has an atraumatic distal end in which the distal region of antenna 104 is wider than the proximal portion of antenna 104. This reduces the risk of perforation of the uterus. The flexible nature of antenna enables antenna 104 to take the natural shape of passage during introduction instead of distorting the passage. For example, when antenna 104 is introduced trans-cervically into the uterus, antenna 104 may acquire the shape of introduction passage comprising the vagina, cervical canal and uterine cavity instead of distorting one or more of the vagina, cervical canal and uterine cavity.

In one embodiment of a deployed configuration of antenna 104 as shown in FIG. 13A, the length of outer loop 112 measured along the outer loop 112 from the distal end of coaxial cable 102 until the distal end 158 of outer loop 112 is about three quarters of the effective wavelength at the 915 MHz ISM band. The effective wavelength is dependent on the medium surrounding the antenna and the design of an antenna dielectric on the outer loop 112. The design of the antenna dielectric includes features such as the type of dielectric(s) and thickness of the dielectric layer(s). The exact length of the outer loop 112 is determined after tuning the length of outer loop 112 to get good impedance matching. The length of the outer loop 112 in one embodiment is 100+/−15 mm. In one embodiment, the width of deployed outer loop 112 is 40+/−15 mm and the longitudinal length of deployed outer loop 112 measured along the axis of coaxial cable 102 is 35+/−10 mm. In the embodiment shown in FIG. 13A, distal end 158 of outer loop 112 is mechanically connected to the distal end of coaxial cable 102 by an elongate dielectric piece 160.

In one embodiment, the proximal portion of outer loop 112 is designed to be stiffer and have greater mechanical strength than the distal portion. In the embodiment shown in FIG. 13A, this may be achieved by leaving original dielectric material 110 of coaxial cable 102 on the proximal portion of outer loop 112. In an alternate embodiment, this is achieved by coating the proximal portion of outer loop 112 by a layer of antenna dielectric.

In the embodiment shown in FIG. 13A, the cross sectional shape of outer loop 112 is not uniform along the entire length of outer loop 112. In this embodiment, the proximal portion of outer loop 112 is a continuation of the inner conductor of coaxial cable 102. This portion has a substantially circular cross section. A middle portion of outer loop 112 has a substantially flattened or oval or rectangular cross section. The middle portion may be oriented generally perpendicular to the distal region of coaxial cable 102 in the deployed configuration. The middle portion of outer loop 112 is mechanically designed to bend in a plane after deployment in the anatomy. This in turn ensures that the distal most region of ablation device 100 is atraumatic and flexible enough to conform to the target tissue anatomy. This helps in the proper deployment of outer loop 112 in the uterus. In one embodiment, the middle portion of outer loop 112 is a continuation of inner conductor of coaxial cable 102 and is flattened. In one embodiment, the distal most portion of outer loop 112 is a continuation of inner conductor of coaxial cable 102 and is non-flattened such that it has a circular cross section.

One or more outer surfaces of outer loop 112 may be covered with one or more layers of antenna dielectrics 116. One or more outer surfaces of center loop 114 may be covered with one or more layers of antenna dielectrics 116. The thickness and type of antenna dielectric material along the length of outer loop 112 is engineered to optimize the microwave field shape. In one embodiment shown in FIG. 13A, every portion of outer loop 112 is covered with some antenna dielectric material such that no metallic surface of outer loop 112 is exposed to tissue. Thus, in the embodiment of FIG. 13A, outer loop 112 is able to transmit a microwave field into tissue, but unable to conduct electricity to tissue. Thus, in the embodiment of FIG. 13A, there is no electrical conduction and no conductive path between outer loop 112 and center loop 114 even though outer loop 112 and center loop 114 may physically touch each other when deployed in the anatomy. Examples of dielectric materials that can be used as antenna dielectrics in one or more embodiments disclosed herein include, but are not limited to EPTFE, PTFE, FEP and other floropolymers, Silicone, Air, PEEK, polyimides, cyanoacrylates, epoxy, natural or artificial rubbers and combinations thereof. In the embodiment of FIG. 13A, the antenna dielectric 116 on the proximal portion of outer loop 112 is a continuation of the dielectric 110 of coaxial cable 102. There may be an additional layer of a stiffer antenna dielectric 116 over this later of antenna dielectric 116. In the embodiment of FIG. 13A, the dielectric on the middle portion of outer loop 112 is a silicone layer with or without impregnated air or a silicone tube enclosing a layer of air. In the embodiment of FIG. 13A, the dielectric on the distal most portion of outer loop 112 is a silicone layer with or without impregnated air or a silicone tube enclosing a layer of air or EPTFE. The thickness of an antenna dielectric on any portion of outer loop 112 may vary along the length of outer loop 112. Further, the crossection of an antenna dielectric on any portion of outer loop 112 may not be symmetric. The various configurations of the antenna dielectric are designed to achieve the desired ablation profile as well as achieve the desired impedance matching or power efficiency. In an alternate embodiment, entire outer loop 112 is covered with silicone dielectric. In one such embodiment, the layer of silicone used to coat the distal most portion of outer loop 112 may be thinner than the layer of silicone used to coat the middle portion of outer loop 112. The thinner silicone dielectric compensates for the lower field strength that normally exists at the distal most portion of a radiating element such as outer loop in FIG. 13A. Thus, the microwave field is made more uniform along the length of outer loop 112. In one device embodiment, outer loop 112 is made of a metallic material and the circumference of the metallic material of the distal region of outer loop 112 is more than the circumference of the metallic material of the middle portion of outer loop 112. This causes the silicone dielectric to stretch more at the distal portion than at the middle portion of outer loop 112. This in turn generates a thinner layer of antenna dielectric at the distal portion of outer loop 112 than at the middle portion of outer loop 112. In another embodiment, entire outer loop 112 is made from a single length of metallic wire of a uniform crossection. In this embodiment, a tubular piece of silicone dielectric of varying thickness is used to cover outer loop 112. The tubular silicone dielectric is used to cover the distal and middle portions of outer loop 112 such that the layer of silicone dielectric is thinner near the distal portion and thicker near the middle portion of outer loop 112.

In FIG. 13A, the shape of outer loop 112 is different from the shape of center loop 114. Further, in FIG. 13A, outer loop 112 and center loop 114 are substantially planar and the plane of outer loop 112 is substantially parallel to the plane of center loop 114. Further, in FIG. 13A, both outer loop 112 and center loop 114 are non-linear.

FIG. 13B shows a section of ablation device 100 of FIG. 13A through the distal end of coaxial cable 102. In FIG. 13B, the identity of coaxial cable 102 ends at the distal end of outer conductor 106. The outer jacket 118 ends a small distance proximal to the distal end of outer conductor 106. Inner conductor 108, cladding 120 and dielectric material 110 extend distally from the distal end of outer conductor 106 into antenna 104. Two proximal ends of center loop 114 are electrically connected to two regions on the outer conductor 106. In one embodiment, the two proximal ends of center loop 114 are electrically connected to diametrically opposite regions on the distal end of outer conductor 106. In one embodiment, the two proximal ends of center loop 114 are soldered to the distal end of outer conductor 106. In another embodiment, the two proximal ends of center loop 114 are laser welded to the distal end of outer conductor 106. The two proximal ends of center loop 114 may be connected to the distal end of outer conductor 106 in various configurations including, but not limited to lap joint and butt joint. In an alternate embodiment, at least one of the two proximal ends of center loop 114 is not connected to the distal end of outer conductor 106. For example, at least one of the two proximal ends of center loop 114 may be electrically connected to a region of outer conductor 106 that is proximal to the distal end of outer conductor 106.

Figure 14A:
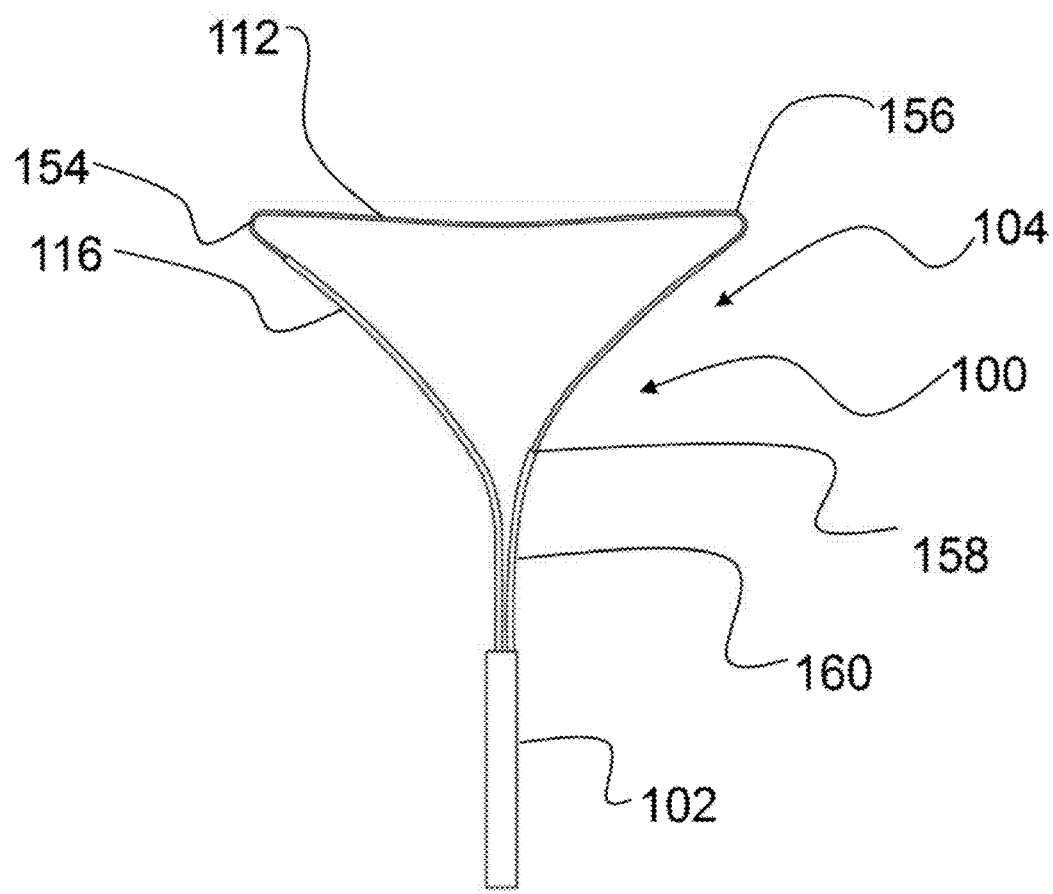
FIG. 14A shows a view of an antenna similar to the antenna of FIG. 13A without a center loop.
Figure 14B:
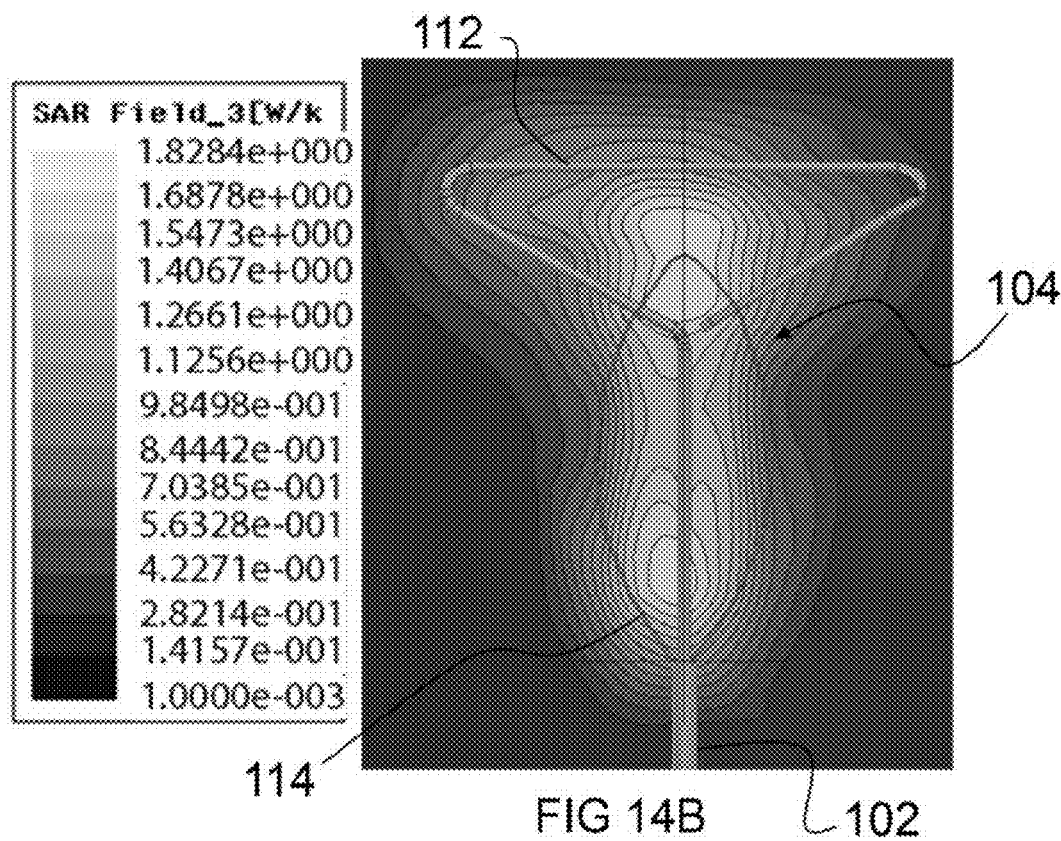
FIGS. 14B and 14C show the front and side views respectively of the SAR profile generated by an antenna with a center loop similar to the antenna of FIG. 13A.

In a method embodiment, when ablation device 100 is used for endometrial ablation, antenna 104 of FIG. 13A generates a substantially uniform microwave field that is more concentrated in the center of the uterus and is less concentrated towards the cornual regions and towards the cervix. Thus, the depth of ablation generated by antenna 104 is deeper in the center of the uterus and is less deep towards the cornual regions and towards the cervix. Such a profile is clinically desired for improved safety and efficacy. In one embodiment, the ablation profile is shaped to ablate a majority of the basalis layer of the uterine endometrium. In one embodiment, center loop 114 is made of a round or flat wire. Examples of flat wires that can be used to make center loop 114 are flat wires made of Ag or Au plated Nitinol or stainless steel with a cross sectional profile of about 0.025"× about 0.007". Such a loop shaped shaping element does not act as a shield for the microwave field. This non-shielding action is visible in the SAR pattern in FIG. 14B. In FIG. 14B, there is no sharp drop in the microwave field intensity past center loop 114. In the embodiment of FIG. 13A, center loop 114 is roughly oval in shape. Two proximal ends of center loop 114 are electrically attached to two circumferentially opposite regions of the outer conductor of coaxial cable 102. In the embodiment of FIG. 13A, the width of center loop 114 is 13+/−5 mm and the length of center loop 114 is 33+/−8 mm. When ablation device 100 is used for endometrial ablation, outer loop 112 and center loop 114 both contact the endometrial tissue surface.

Center loop 114 may be mechanically independent from outer loop 112 or may be mechanically attached to outer loop 112. In the embodiment shown in FIG. 13A, center loop 114 is mechanically independent from outer loop 112 and lies on one side of outer loop 112. In an alternate embodiment, a portion of center loop 114 passes through the interior of outer loop 112. In an alternate embodiment, a portion of center loop 114 is mechanically connected to outer loop 112. This may be done for example, by using an adhesive to connect a portion of center loop 114 to outer loop 112. In an alternate embodiment, one or more portions of center loop 114 are mechanically connected to one or more portions of outer loop 112 by one or more flexible attachments.

Parts of center loop 114 may or may not be covered by one or more layers of antenna dielectric materials 116. In the embodiment of FIG. 13A, one or more or all metallic surfaces of center loop 114 are exposed to the device environment.

Portions of outer loop 112 and center loop 114 may be made from one or more of lengths of metals such as copper, Nitinol, aluminum, silver or any other conductive metals or alloys. One or more portions of outer loop 112 and center loop 114 may also be made from a metallized fabric or plastics.

Figure 14C:
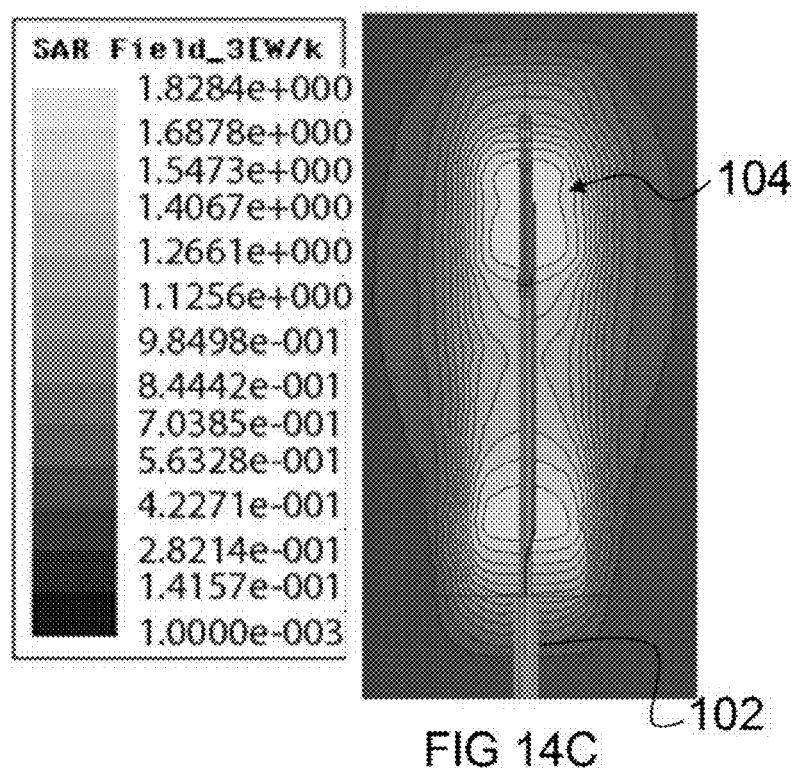

FIGS. 14B and 14C show the front and side views respectively of the SAR profile generated by an antenna with a center loop similar to the antenna of FIG. 13A. In the embodiment in FIG. 14B, the distal end of outer loop 112 is mechanically and non-conductively attached to a region of outer loop 112 proximal to the distal end of outer loop 112. Thus, outer loop 112 has a substantially linear proximal region and a looped distal region. In one embodiment, the looped distal region may be substantially triangular in shape as shown in FIG. 14B. Outer diameter of antenna dielectric 116 on the proximal region of outer loop 112 may be larger than or substantially the same as the outer diameter of antenna dielectric 116 on the looped distal region of outer loop 112. Antenna dielectric 116 on the looped distal region of outer loop 112 may be a layer of silicone of varying thickness. Outer loop 112 may be made of a silver or gold clad metal such as Nitinol. Center loop 114 may be made of a silver or gold clad metal such as Nitinol. In the embodiment shown in FIGS. 14B and 14C, center loop 114 is not covered with any antenna dielectric 116. Thus the metallic surface of center loop 114 may be exposed to the surrounding. Outer loop 112 and center loop 114 may physically touch each other when deployed in the anatomy as shown in FIG. 14E. In FIG. 14B, the microwave field is shaped such that the ablation at the center of antenna 104 will be deeper than the ablation at the corners of antenna 104. This is clinically desirable for endometrial ablation. Also, FIGS. 14B and 14C show that the microwave field volumetrically envelops entire antenna 104. Also, FIGS. 14B and 14E show that the microwave field is substantially bilaterally symmetric. FIG. 14E shows the front view of the SAR profile generated by antenna 104 of FIG. 14B without center loop 114. The microwave effect of shaping element 114 in FIG. 14B can be seen by comparing FIG. 14B to FIG. 14E. FIG. 14E shows a first unshaped field that is not shaped by shaping element 114. When the antenna 104 comprises a shaping element 114 as shown in FIG. 14B, the antenna generates a shaped microwave field as shown in FIG. 14B. It should be noted that in FIGS. 14B and 14C, the shaped microwave field is more uniformly distributed over a wider area of the endometrium than in FIG. 14E. In FIG. 14E, the unshaped microwave field is more concentrated at the distal end of coaxial cable 102. A more uniformly distributed, shaped microwave field such as in FIGS. 14B and 14E is clinically desirable for endometrial ablation. Further when antenna 104 of FIG. 14B is used for endometrial ablation, the microwave field is distributed over a wider area of the endometrium that the microwave field generated by antenna 104 of FIG. 14E. This can be seen by comparing the SAR profile distal to the distal end of coaxial cable 102 in FIGS. 14B and 14C to the SAR profile distal to the distal end of coaxial cable 102 in FIG. 14E. Further, in FIG. 14E, a portion of the unshaped microwave field extends to a significant distance proximal to the distal end of coaxial cable 102. In FIGS. 14B and 14E, an insignificant portion of the microwave field extends proximally to the distal end of coaxial cable 102. Thus the microwave field profile of FIGS. 14B and 14C is advantageous over the microwave field profile of FIG. 14E since it limits collateral damage to healthy tissue. Thus the presence of center loop 114 shapes the microwave field such that the microwave field is more distributed. In absence of center loop 114, the microwave field interacts with an element of transmission line 102 such as the outer conductor of a coaxial cable. This results in a non-desirable profile of the microwave field e.g. a concentrated field around the distal end of the transmission line 102 as shown in FIG. 14E. This interaction can also cause backward heating of coaxial cable 102 that may lead to collateral damage of healthy tissue. Further, the combination of outer loop 112 and center loop 114 creates a more robust antenna 104 wherein the performance of antenna 104 is less affected by distortions during clinical use. Also, FIGS. 14B and 14C show that the microwave field volumetrically envelops entire antenna 104.

Further, the SAR profile of FIG. 14B demonstrates that the entire uterine endometrium can be ablated in a single ablation. Thus the physician does not need to reposition antenna 104 after a first endometrial ablation. This novel aspect of the device and procedure greatly reduces the amount of time needed for the procedure and also reduces the procedure risks and physician skill requirements. In the embodiments disclosed herein, a combination of direct microwave dielectric heating and thermal conduction through tissue is used to achieve the desired therapeutic effect. The thermal conduction evens out any minor variations in the microwave field and enables the creation of a smooth, uniform ablation. Further, the SAR profile of FIGS. 14B and 14C demonstrates that antenna 104 is capable of ablating an entire volume surrounding antenna 104 not just ablating between the surfaces of outer loop 112 and center loop 114. Further, the SAR profile of FIGS. 14B and 14C demonstrates that antenna 104 is capable of ablating a tissue region without leaving any "gaps" of unablated tissue within that tissue region. Further, the SAR profile of FIGS. 14B and 14C demonstrates that the entire microwave field generated by antenna 104 is used for ablation. The entire microwave field comprises the microwave field around outer loop 112, the microwave field around center loop 114, the microwave field between outer loop 112 and center loop 114 and the field within center loop 114. Further, the SAR profile of FIGS. 14B and 14C demonstrates that the microwave field is located all around outer loop 112 and is not shielded or reflected by center loop 114. Thus center loop 114 does not act as a shield or reflector in the embodiment shown in FIGS. 14B and 14C.

Various embodiments of antenna 104 may be designed to generate a variety of shapes of SAR and/or the ablation profile. For example, antennas 104 may be designed to generate substantially square, triangular, pentagonal, rectangular, round or part round (e.g. half round, quarter round, etc.), spindle-shaped or oval SARs or ablation patterns.

Figure 14D:
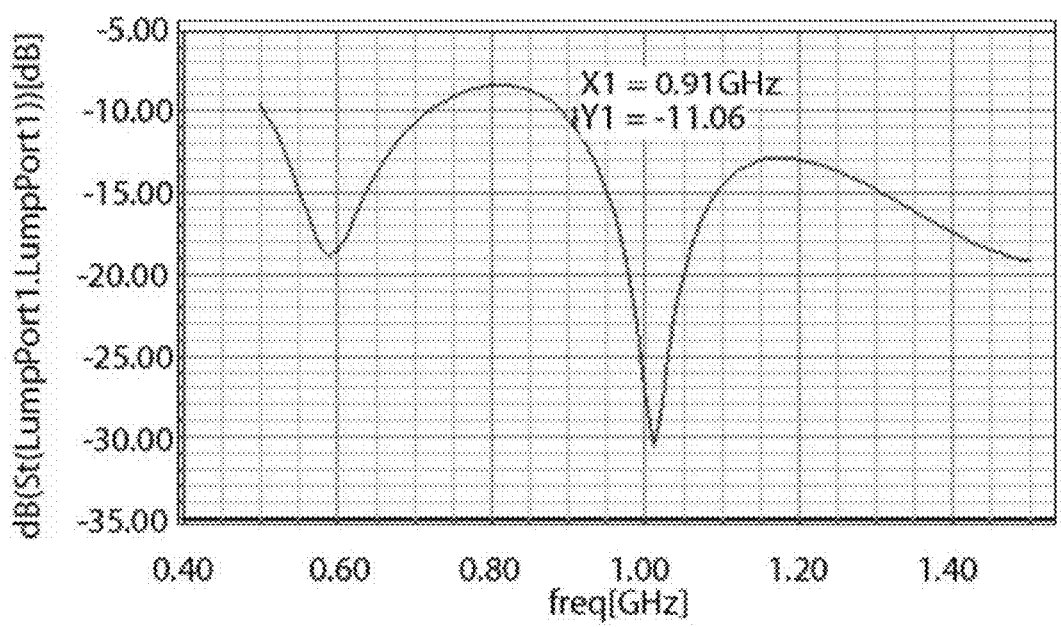
FIG. 14D shows the simulated return loss of an ablation device with an antenna of FIG. 14B.
Figure 14E:
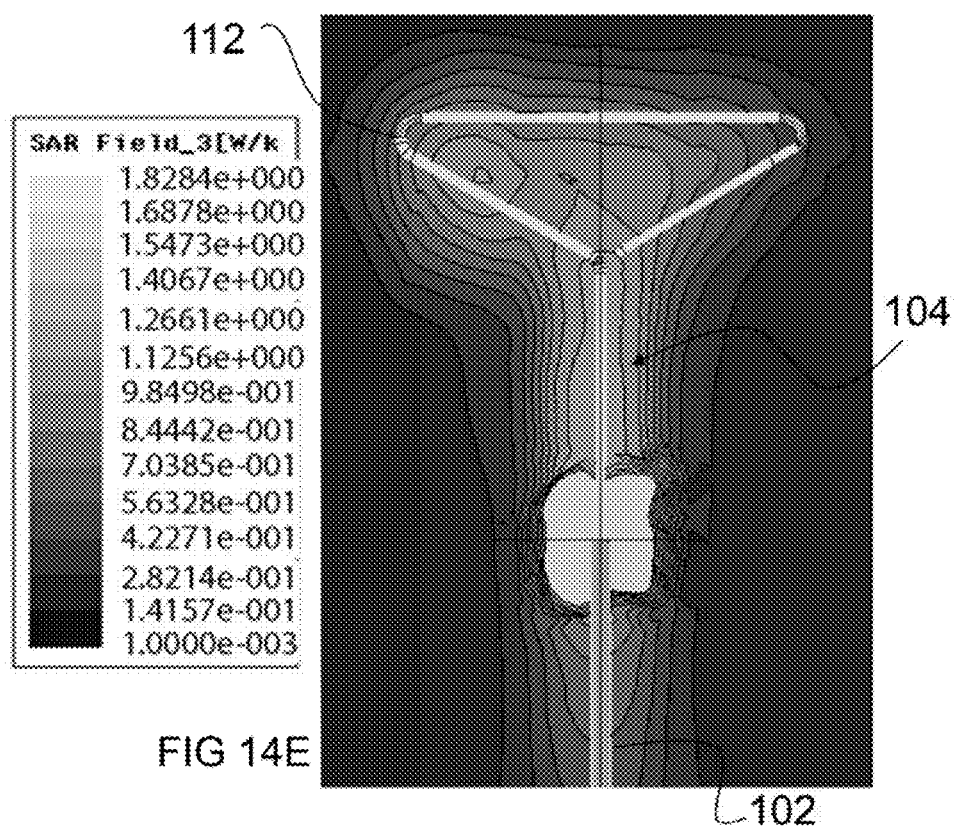
FIG. 14E shows the front view of the SAR profile generated by the antenna of FIG. 14B without center loop.
Figure 14F:
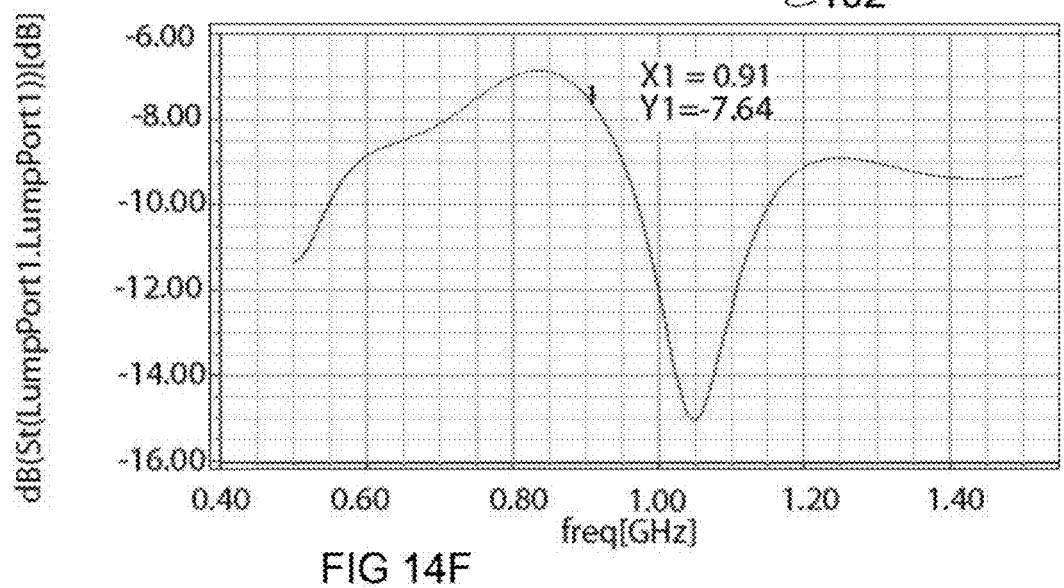
FIG. 14F shows the simulated return loss of an ablation device with the antenna of FIG. 14E.

FIG. 14D shows the simulated return loss of an ablation device with antenna 104 of FIG. 14B. The simulated return loss shows good matching (about −11 dB) at 915 MHz. FIG. 14F shows the simulated return loss of an ablation device with an antenna of FIG. 14E. The simulation shows a return loss of about −7.5 dB at 915 MHz. Thus, the presence of center loop 114 also improves the matching and increases the power efficiency. In the presence of center loop 114, microwave power is delivered more efficiently to the tissue and not wasted as heat generated within ablation device 100.

Shaping element 114 also increases the frequency range (bandwidth) over which antenna 104 delivers an acceptable performance. If the graphs in FIGS. 14D and 14F are compared, at a cutoff of −10 dB, the acceptable frequency range in the embodiment containing shaping element 114 is more than 0.52 GHz (spanning from approximately 0.88 GHz to more than 1.40 GHz). The acceptable frequency range in the comparable embodiment of FIG. 14E without shaping element 114 is only about 0.18 GHz (spanning from approximately 0.97 GHz to approximately 1.15 GHz). Thus in the first case, a larger frequency range (bandwidth) is available over which antenna 104 delivers an acceptable performance. This in turn allows for a design of antenna 104 wherein minor distortions of antenna 104 during typical clinical use or due to minor manufacturing variations do not significantly affect the performance of antenna 104.

Figure 14G:
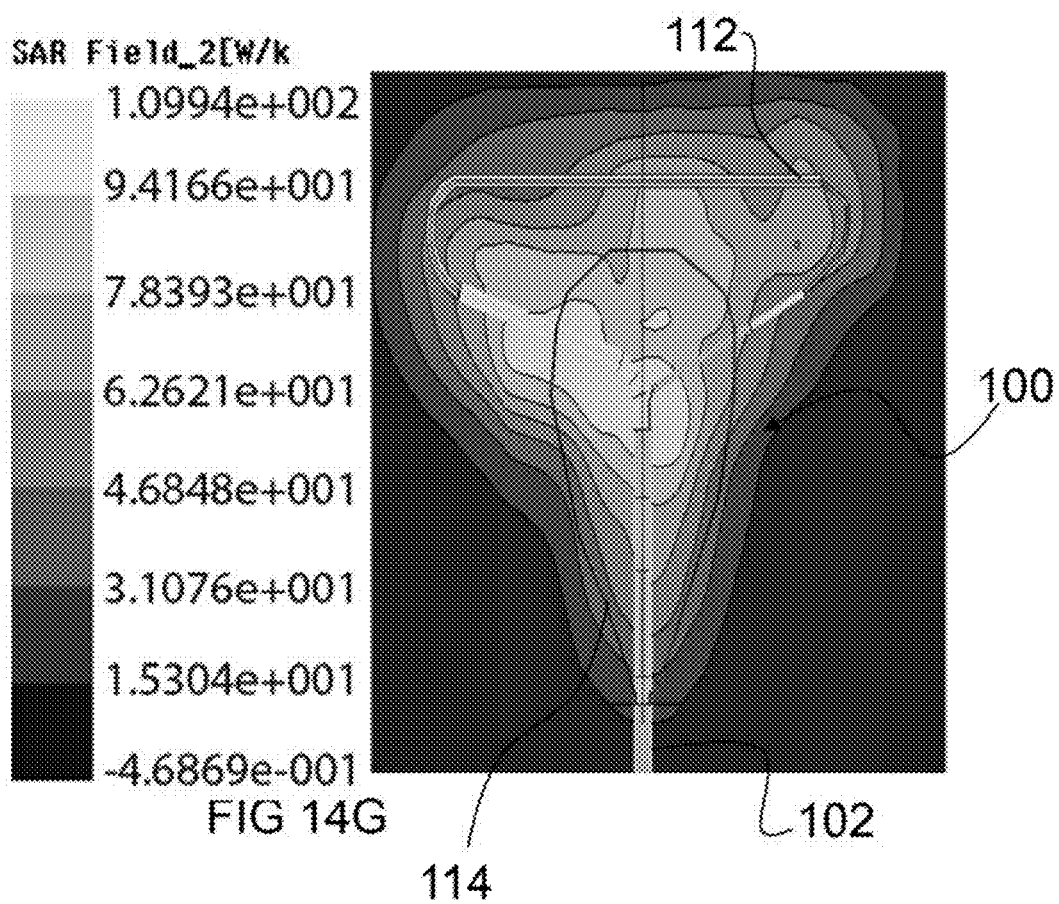
FIGS. 14G and 14H show the front and side views respectively of the SAR profile generated by an antenna with a center loop similar to the antenna of FIGS. 14B and 14C.
Figure 14H:
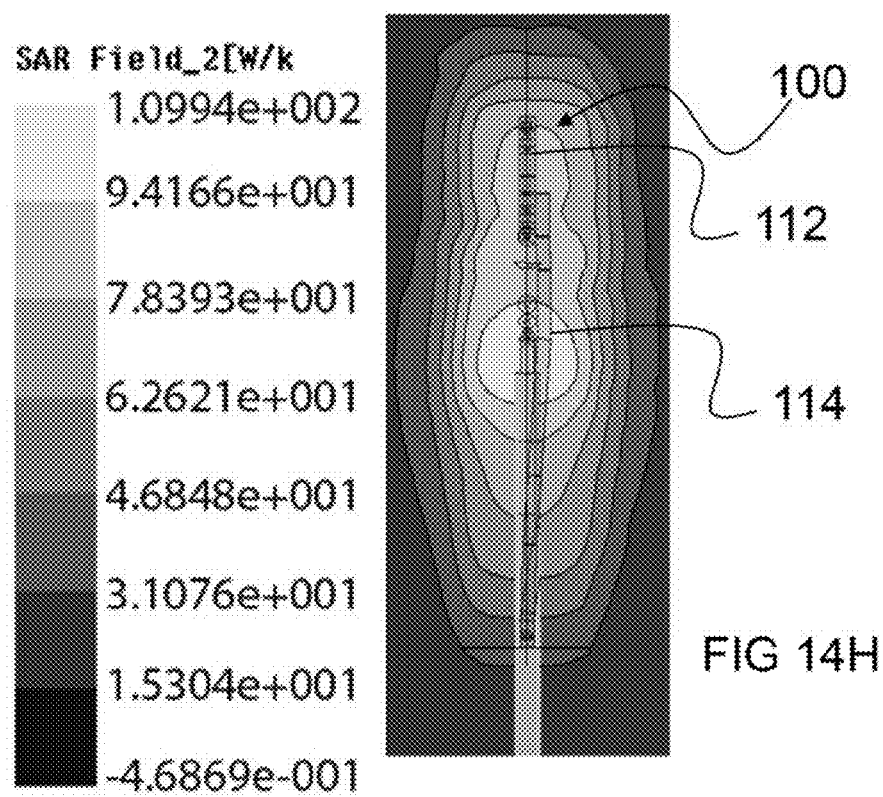

FIGS. 14G and 14H show the front and side views respectively of the SAR profile generated by an antenna with a center loop similar to the antenna of FIG. 14B. The general construction of the embodiment in FIG. 14G is similar to the general construction of the embodiment in FIG. 14B. However, in FIG. 14G, the radius of curvature of the two distal edges of the looped distal region of outer loop 112 is more than the corresponding radius of curvature in FIG. 14B. Further, the length of the substantially linear proximal region of outer loop 112 is less than the corresponding length in FIG. 14B. Also, the design of antenna dielectric 116 on antenna 104 in FIG. 14G is different from the design of antenna dielectric 116 on antenna 104 in FIG. 14B. In one embodiment, antenna dielectric 116 on the proximal region of outer loop 112 is made of a layer of PEEK over a layer of EPTFE. The PEEK layer increases the mechanical strength of the proximal region of outer loop 112. In this embodiment, the antenna dielectric 116 on the looped distal region of outer loop 112 is silicone of varying thickness. The thickness of the silicone antenna dielectric 116 on the more proximal portion of the looped distal region of outer loop 112 may be more than the thickness of silicone antenna dielectric 116 on the more distal portion of the looped distal region of outer loop 112. Outer loop 112 may be made of a silver or gold clad metal such as Nitinol. Center loop 114 may be made of a silver or gold clad metal such as Nitinol. In the embodiment shown in FIGS. 14B and 14C, center loop 114 is not covered with any antenna dielectric 116. Thus the metallic surface of center loop 114 may be exposed to the surrounding. Outer loop 112 and center loop 114 may physically touch each other when deployed in the anatomy as shown in FIG. 14C. The clinical advantages of the shape of the SAR profile of antenna 104 in FIGS. 14G and 14H are similar to the clinical advantages of the SAR profile of antenna 104 in FIGS. 14B and 14C.

FIGS. 14I and 14J show two alternate embodiments of shapes of microwave antenna 104 of ablation device 100. In FIGS. 14I and 14J, center loop 114 is not shown. In FIG. 14I, microwave antenna 104 is roughly diamond shaped. The distal most region of microwave antenna 104 measured along the axis of coaxial cable 102 comprises a smooth corner. The microwave antenna 104 in this embodiment is pre-shaped to form the shape as shown in FIG. 14I. Such a microwave antenna 104 can be collapsed to enable insertion of microwave antenna 104 in a collapsed, low-profile configuration though a lumen of a device. In FIG. 14I, microwave antenna 104 is sized and shaped such that when antenna 104 is deployed in the uterine cavity, the distal most region of microwave antenna 104 measured along the axis of coaxial cable 102 is pushed by the uterine fundus and flattened to achieve the configuration as shown by the dashed lines. Thus microwave antenna 104 is converted to a roughly triangular shape that is suited for endometrial ablation. In FIG. 14J, the distal most region of microwave antenna 104 measured along the axis of coaxial cable 102 comprises a smooth arc or curve. The microwave antenna 104 in this embodiment is pre-shaped to form the shape as shown in FIG. 14J. Such a microwave antenna 104 can be collapsed to enable insertion of microwave antenna 104 in a collapsed, low-profile configuration though a lumen of a device. In FIG. 14J, microwave antenna 104 is sized and shaped such that when it is deployed in the uterine cavity, the distal most region of microwave antenna measured along the axis of coaxial cable 102 is pushed by the uterine fundus and flattened to achieve the configuration as shown by the dashed lines. Thus microwave antenna 104 is converted to a roughly triangular shape that is suited for endometrial ablation. In an alternate embodiment, microwave antenna 104 has elastic, super-elastic or shape memory ability. In this embodiment, microwave antenna 104 regains its shape after deployment in the uterine cavity through a lumen of a device. FIG. 14K shows the substantially circular crossection of microwave antenna 104 through plane 14K-14K. FIG. 14L shows two alternate crossections of microwave antenna 104 through plane 14L-14L. In FIG. 14L, one alternate crossection is rectangular while the other alternate crossection is oval.

Figure 14M:
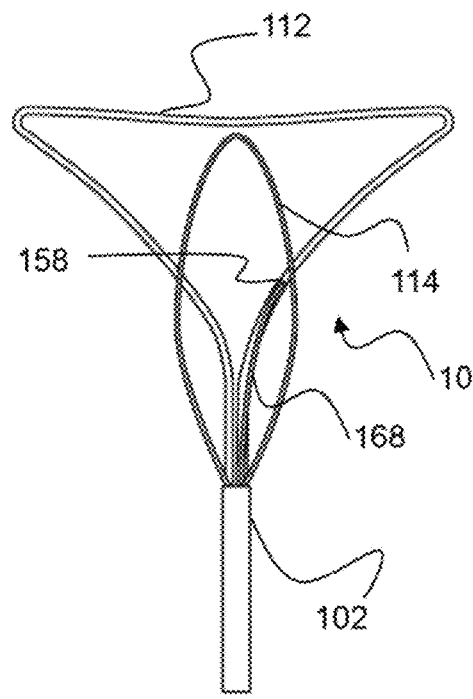
FIGS. 14M-14O show various embodiments of ablation devices comprising roughly triangular shaped microwave antennas.
Figure 14N:
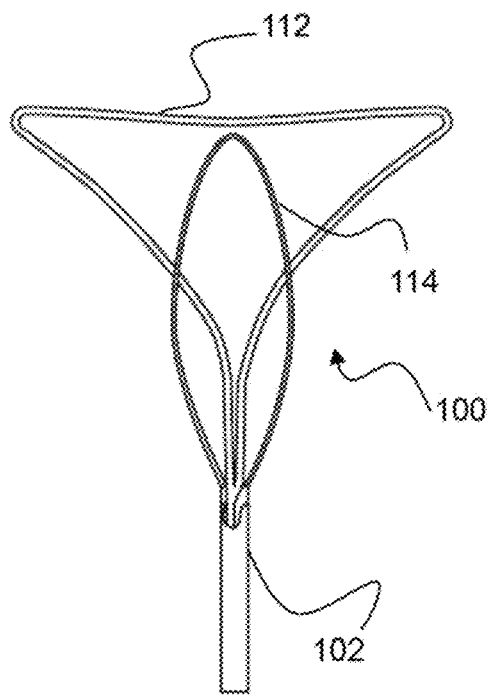
Figure 14O:
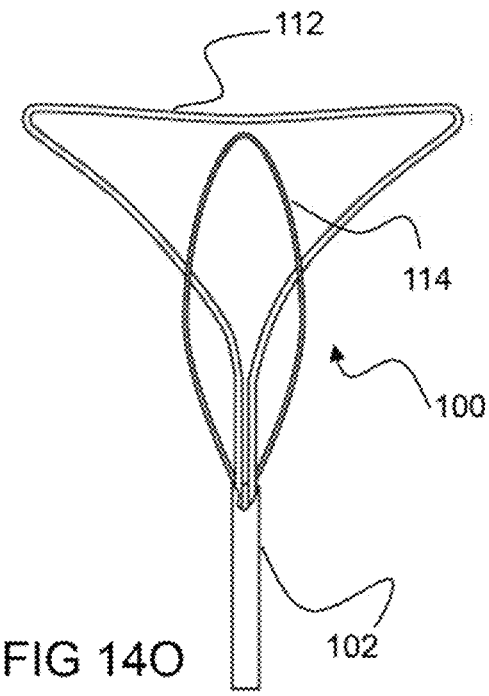

FIGS. 14M-14O show various embodiments of ablation devices 100 comprising roughly triangular shaped microwave antennas 104. In FIG. 14M, ablation device 100 comprises a coaxial cable 102, an outer loop 112 and a center loop 114. Ablation device 100 further comprises an elongate metallic conductor 168 similar to elongate metallic conductor 168 of FIG. 14R. The proximal end of elongate metallic conductor 168 is electrically connected to the distal end of outer conductor 106 of coaxial cable 102. The distal end of metallic conductor 168 is non-conductively attached to the distal end 158 of outer loop 112. Metallic conductor 168 confers mechanical stability to the outer loop 112 as well as shapes the microwave field. In FIG. 14N, ablation device 100 comprises a coaxial cable 102, an outer loop 112 and a center loop 114. In this embodiment, a region of outer loop 112 adjacent to the distal end of coaxial cable 102 is electrically shorted to another region of outer loop 112 adjacent to the distal end of coaxial cable 102. In FIG. 14O, ablation device 100 comprises a coaxial cable 102, an outer loop 112 and a center loop 114. In this embodiment, regions of outer loop 112 are electrically isolated from other regions of outer loop 112. Thus, no two regions of outer loop 112 are conductively connected.

Figure 14P:
FIGS. 14P-14R show various alternate embodiments of center loop.
Figure 14Q:
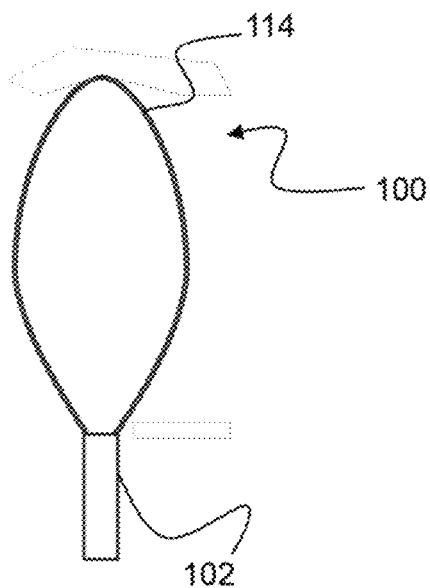
Figure 14R:
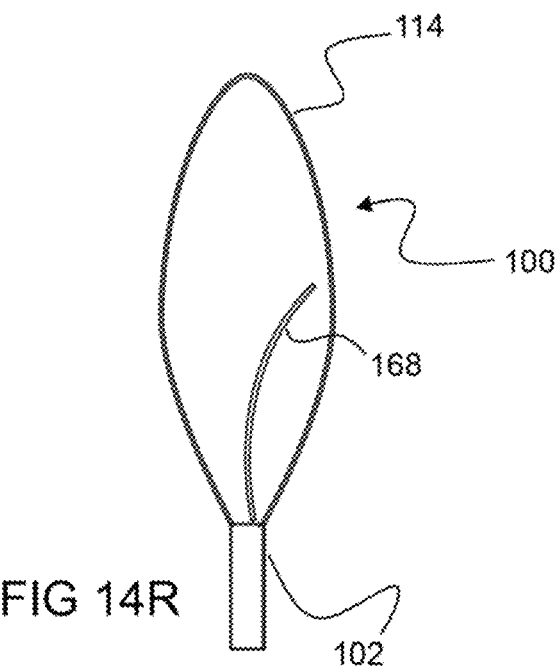

FIGS. 14P-14R show various alternate embodiments of center loop 114. Center loop 114 in FIGS. 14P-14R is made of Ag or Au plated Nitinol or stainless steel. Center loop 114 may or may not be pre-shaped. The crossection of center loop 114 may be circular or rectangular or oval. Center loop 114 may be multi-stranded. In FIG. 14P, center loop 114 is roughly oval in shape and has a width of 13+/−5 mm and a length of about 35+/−8 mm. In FIG. 14Q, center loop 114 is roughly oval in shape and has a width of 13+/−5 mm and a length of about 27.5+/−8 mm. In FIG. 14R, center loop 114 is roughly oval in shape and has a width of 13+/−5 mm and a length of about 35+/−8 mm. In FIG. 14R, ablation device 100 further comprises one or more additional elongate metallic conductors 168 electrically connected to the distal end of outer conductor 106. The distal end of elongate metallic conductor 168 is connected to a region of antenna 104 to confer mechanical stability to antenna 104 as well as to shape the microwave field. In a one embodiment, the distal end of elongate metallic conductor 168 is connected to a region of antenna 104 by a non-conductive connection. Various antennas 104 may be designed using a combination of various elements disclosed herein. Various antennas 104 may be designed using any combination of a radiating element 112 disclosed herein and a shaping element 114 disclosed herein. For example, a design of outer loop 112 from FIGS. 14I-14O may be combined with a design of center loop 114 in FIGS. 14P-14R to create various antennas 104.

Figure 14S:
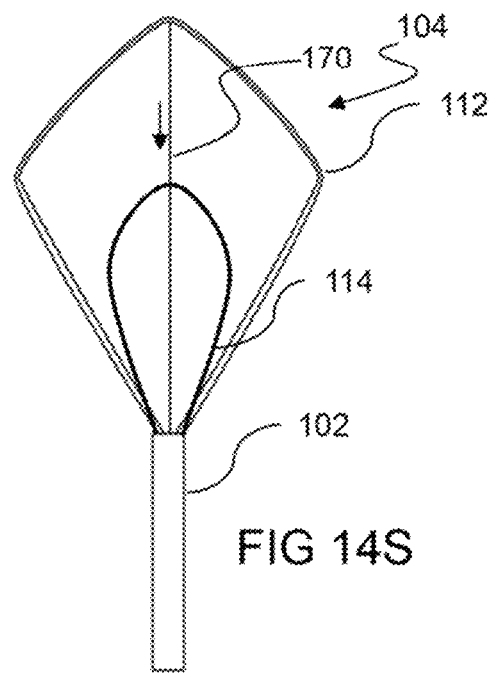
FIGS. 14S and 14T show two configurations of a mechanically deployable antenna.
Figure 14T:
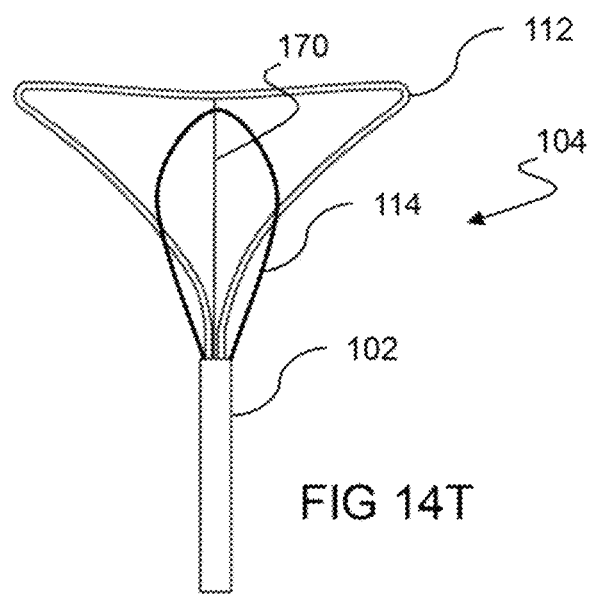

FIGS. 14S and 14T show two configurations of a mechanically deployable antenna. In FIG. 14S, antenna 104 comprises an outer loop 112 and a center loop 114. In FIG. 14S, antenna 104 is in a non-working configuration. Antenna 104 in this embodiment is user deployable by engaging a mechanical deployment system. The mechanical deployment system in the embodiment in FIGS. 14S and 14T is a pullable and releasable pull wire 170 attached to a region of outer loop 112. Pull wire 170 may be made of a metallic or non-metallic e.g. polymeric material. When pull wire 170 is pulled along the proximal direction, outer loop 112 is distorted. The distortion is such that antenna 104 achieves a working configuration as shown in FIG. 14T. Such an embodiment wherein a pull wire 170 is used to convert antenna 104 from a non-working configuration to a working configuration is advantageous since presence of tissue forces are not required for the proper deployment of antenna. This allows the antenna 104 to be made stiffer. One or more pull wires 170 may be attached to one or more regions of antenna 104 to controllably modify the orientation of antenna 104 relative the axis of the distal end of coaxial cable 102. This may be used to position antenna 104 relative to a target tissue in a desired orientation while performing e.g. a laparoscopic procedure. Further, a mechanical deployment system allows the user to get a feedback about the proper deployment of antenna 104. This eliminates the necessity of a post-deployment visualization of antenna 104 to confirm proper deployment. For example, the mechanical deployment system as shown in FIGS. 14S and 14T allows the user to get a tactile feedback about the proper deployment of antenna 104 by the forces the user experiences while engaging pull wire 170. In another example, the mechanical deployment system as shown in FIGS. 14S and 14T allows the user to visually observe the extent of displacement of pull wire 170 which is correlated to the extent of deployment of antenna 104.

Figure 14U:
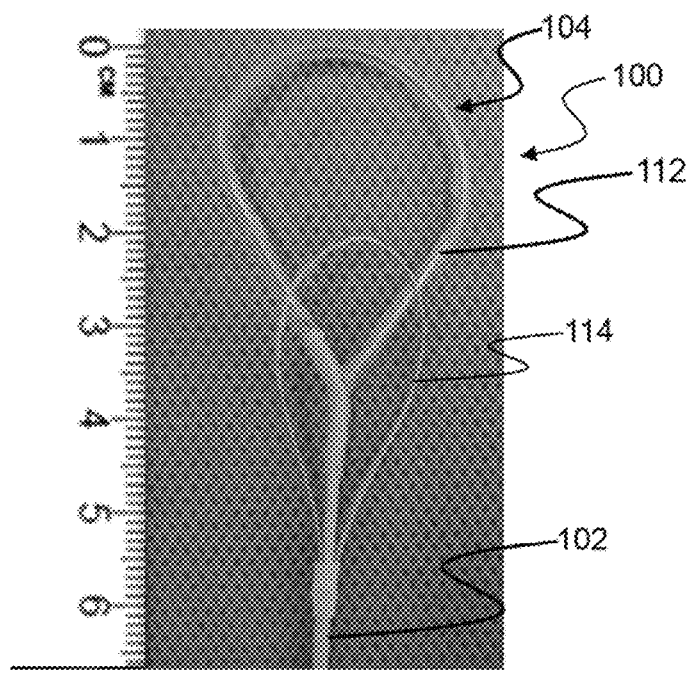
FIG. 14U shows a longitudinally un-constrained and laterally un-collapsed configuration of an embodiment of a microwave antenna.

FIG. 14U shows a longitudinally un-constrained and laterally un-collapsed configuration of an embodiment of a microwave antenna. In FIG. 14U, ablation device 100 comprises an antenna 104 comprising an outer loop 112 and a metallic center loop 114. Outer loop 112 in this configuration is in a more oval shape. The distal end of outer loop 112 is connected to a proximal portion of outer loop 112 by a non-electrically conducting connection. The maximum lateral width dimension of antenna 104 is about 2.7 cm. The lateral width of center loop 114 may be 1.6 cm+/−0.6 cm and the longitudinal length of center loop 114 may be about 3.5 cm+/−1 cm.

Figure 14V:
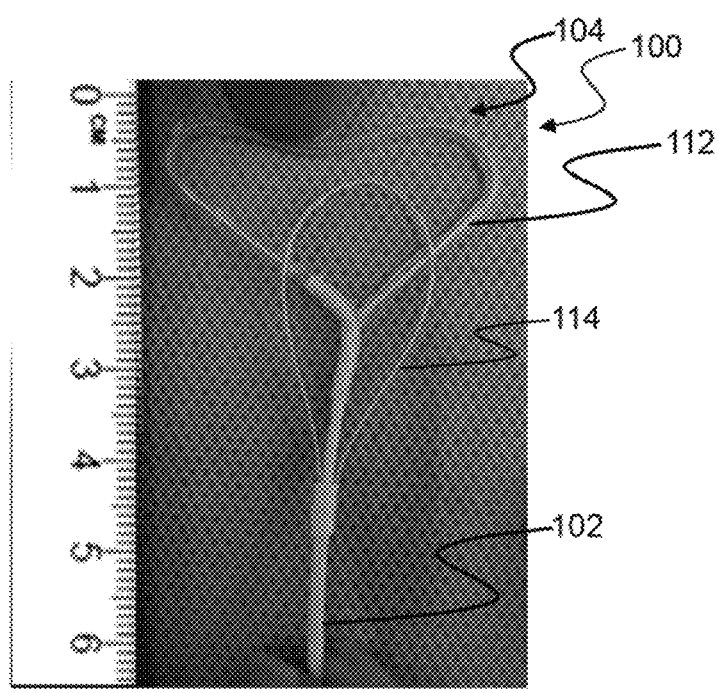
FIG. 14V shows a longitudinally constrained and laterally un-collapsed working configuration of the embodiment of a microwave antenna shown in FIG. 14U.

FIG. 14V shows a longitudinally constrained and laterally un-collapsed working configuration of the embodiment of a microwave antenna shown in FIG. 14U. In FIG. 14V, an external force is used to distort the distal most portion of antenna 104. In FIG. 14V, a finger was used to distort the distal most portion of antenna 104 to change outer loop 112 from a more oval shape to a more triangular shape as shown. The maximum lateral width dimension of outer loop 112 is now about 3.5 cm. The longitudinal length of antenna 104 from the distal end of coaxial cable 102 till the distal most portion of antenna 104 is about 3.8 cm. This simulates the distortion that antenna 104 experiences by the fundus during actual clinical use in endometrial ablation. The configuration shown in FIG. 14V is the working configuration of antenna 104 in which antenna 104 can be used for endometrial ablation. Thus several embodiments of antenna 104 herein are capable of existing in 3 configurations: a first configuration in which antenna 104 is laterally compressed for insertion through a lumen or opening, a second configuration in which antenna 104 is longitudinally un-constrained and laterally un-collapsed in the absence of significant external distorting forces on antenna 104 and a third configuration in which antenna 104 is longitudinally constrained and laterally un-collapsed in the presence of external distorting forces on antenna 104. The third configuration is the actual working configuration.

Figure 14W:
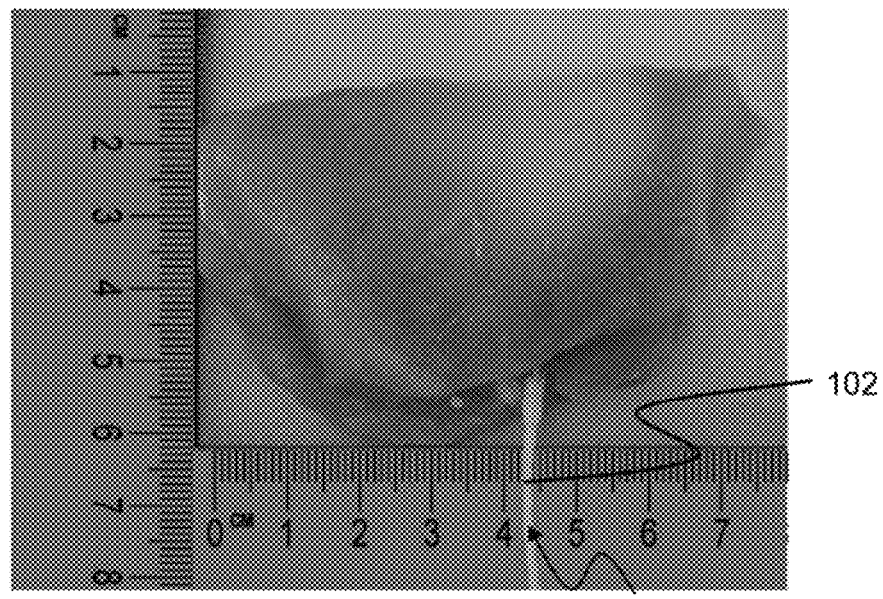
FIG. 14W shows the placement of the microwave antenna of FIGS. 14U and 14V in a folded piece of tissue.

FIG. 14W shows the placement of the microwave antenna of FIGS. 14U and 14V in a folded piece of tissue. In FIG. 14W, a slab of porcine muscle tissue maintained at 37 degrees C. was folded over once. The cavity enclosed by the tissue fold approximately simulates the uterine cavity. Thereafter, antenna 104 of FIGS. 14U and 14V was inserted to a sufficient depth such that the distal most region of antenna 104 is distorted by the porcine tissue to achieve the working configuration as shown in FIG. 14V. Thereafter, the porcine tissue was ablated. The ablation was done for 90 s with a delivery of 40 W of microwave power from a microwave generator at 0.915 GHz. Although in this experiment, a constant power of 40 W was used throughout the ablation procedure; in clinical use the magnitude of power delivery by the microwave generator may not be constant throughout the ablation procedure.

If we assume that about 85% of the total microwave energy delivered by the microwave generator is ultimately delivered by antenna 104 to tissue, the total energy delivered to tissue is about 3,000 Joules. Since the tissue used in FIG. 14W is designed to simulate uterine endometrial tissue, endometrial ablation protocols may be designed that involve the delivery of about 3,000 Joules of microwave energy to the endometrium. Further, protocols of endometrial ablation may be designed that deliver less than 3,000 Joules of microwave energy to the endometrium. This can be done for example, by pre-treatment of the uterus, by scheduling the patient for the ablation just after she has a menstrual period, etc.

In FIG. 14V, the total area of generally flattened antenna 104 in its working configuration is about 6.7 square centimeters. Thus, the microwave energy delivered by antenna 104 is delivered to two opposite tissue surfaces, each measuring about 6.7 square centimeters. Again, if we assume that about 85% of the total microwave energy delivered by the microwave generator is ultimately delivered by antenna 104 to tissue, the total power delivered to tissue is about 2.5 Watts per square centimeter of tissue. Further, protocols of endometrial ablation may be designed that achieve the desired clinical outcome while delivering less than 2.5 Watts of microwave power per square centimeter of endometrial surface. This can be done for example, by hormonal pre-treatment of the uterus, by a mechanical pre-treatment of the uterus by D&C, by scheduling the patient for the ablation just after she has a menstrual period, etc.

Figure 14X:
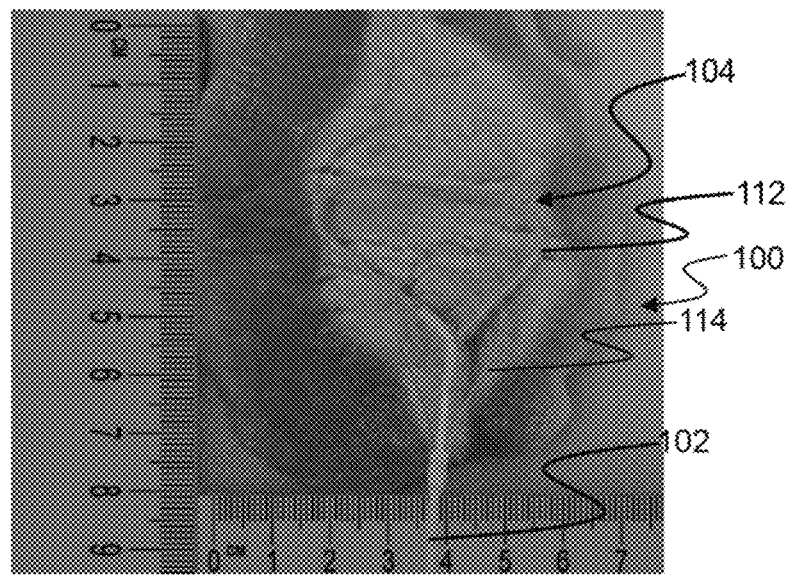
FIG. 14X shows the unfolded piece of tissue of FIG. 14W showing the placement of the microwave antenna of FIGS. 14U and 14V in a longitudinally constrained and laterally un-collapsed working configuration and the ablation obtained from the microwave antenna.

FIG. 14X shows the unfolded piece of tissue of FIG. 14W showing the placement of the microwave antenna of FIGS. 14U and 14V in a longitudinally constrained and longitudinally collapsed working configuration and the ablation obtained from the microwave antenna. It should be noted that the ablation is roughly triangular in shape. Such an ablation in the uterus is capable of ablating the entire uterine endometrium to treat menorrhagia.

Figure 14Y:
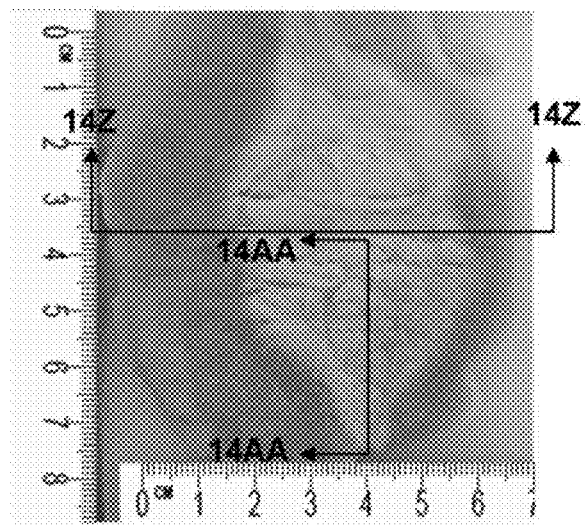
FIG. 14Y shows an unfolded view of ablated tissue after the ablation shown in FIG. 14W.
Figure 14Z:
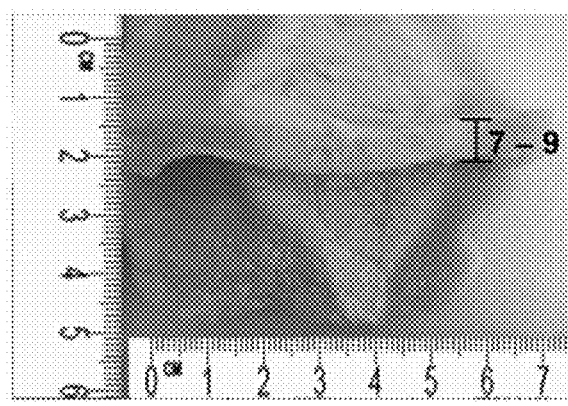
FIG. 14Z shows a view of the ablated tissue sliced through the plane 14Z-14Z in FIG. 14Y.
Figure 14A:
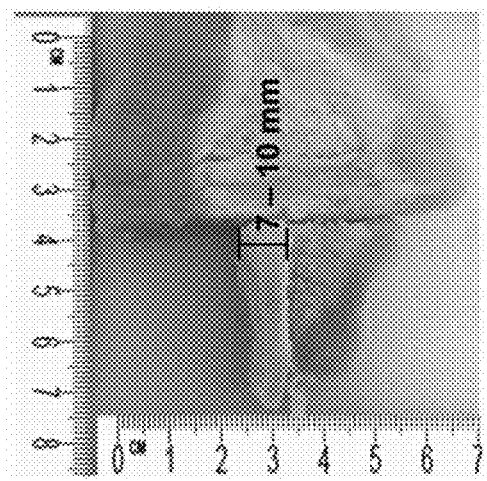

FIG. 14Y shows an unfolded view of ablated tissue after the ablation shown in FIG. 14W. FIG. 14Z shows a view of the ablated tissue sliced through the plane 14Z-14Z in FIG. 14Y. It is seen in FIG. 14Z, that the ablation is uniform and spans the full thickness of the tissue. There is no charring noted anywhere. Thus a transmural ablation spanning the full 7-9 mm depth of tissue has been created. FIG. 14AA shows a view of the ablated tissue sliced through the plane 14AA-14AA in FIG. 14Y. Similar to FIG. 14Z, FIG. 14AA shows that the ablation is uniform and spans the full thickness of the tissue. There is no charring noted anywhere. Thus a transmural ablation spanning the full 7-10 mm depth of tissue has been created. Further, it should be noted that the lesion is deeper in the center and shallower towards the periphery of the lesion. Such an ablation is clinically desired since the thickness of the endometrium is greater toward the center of the uterus and is lower in the cornual regions and towards the lower uterine region. Further, deeper lesions may be created if desired by using one or more of: increasing the power delivered by the microwave generator, increasing the ablation time, occluding the blood flow to the uterus by temporarily occluding the uterine arteries, etc. Further, shallower lesions may be created if desired by using one or more of: reducing the power delivered by the microwave generator, reducing the ablation time, circulating a cooling agent in the anatomy, etc.

Figure 15A:
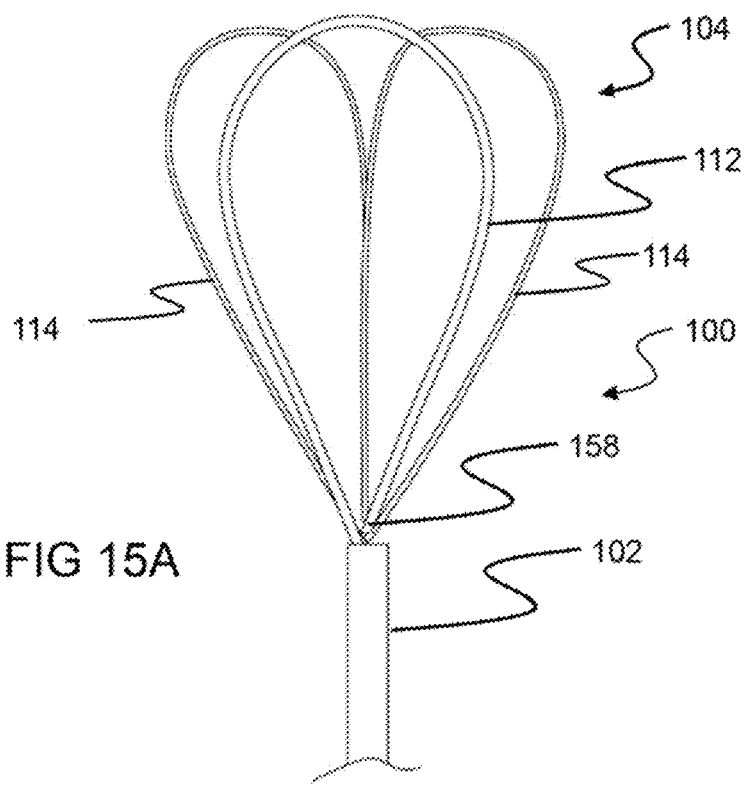
FIG. 15A shows a view of an antenna of a microwave ablation device optimized for endometrial ablation that comprises a single radiating element and two shaping elements.

FIG. 15A shows a view of an antenna of a microwave ablation device optimized for endometrial ablation that comprises a single radiating element and two shaping elements. In FIG. 15A, antenna 104 comprises an open loop shaped radiating element 112 that lies roughly at the center of antenna 104. Distal end 158 of radiating element 112 lies adjacent to the distal end of transmission line 102. The distal end 158 of radiating element 112 points in the proximal direction. In one embodiment, radiating element 112 is a continuation of the inner conductor 108 of coaxial cable 102. At least a proximal portion of radiating element 112 is covered with an antenna dielectric 116 such as dielectric 110 of coaxial cable 102. The total length of radiating element 112 is about 110+/−20 mm or about three quarters of the effective wavelength at 915 MHz. In one embodiment, an antenna dielectric 116 may be located at the distal end of transmission line 102. This antenna dielectric 116 may envelop the proximal portion of radiating element 112, the distal end 158 of radiating element 112, and the proximal portions of looped shaping elements 114. In addition to locally modifying the dielectric properties of antenna 104, this antenna dielectric 116 may also be used to mechanically hold together various portions of antenna 104. The amount of antenna dielectric on radiating element 112 can be controlled for tuning antenna 104 and shaping the microwave field profile generated by antenna 104. Antenna 104 further comprises two shaping elements 114 located on either side of radiating element 112 as shown. In one embodiment, two shaping elements 114 are formed by two lengths of conductive wires covered with an antenna dielectric 116. The proximal end of each of two shaping elements 114 is conductively connected to outer conductor 106 of coaxial cable 102. In one embodiment, the length of each shaping element 114 is about 110+/−20 mm or about three quarters of the effective wavelength at 915 MHz. The distal ends of each shaping element 114 are joined together such that they form a common segment as shown in FIG. 15A. The microwave field emitted from radiating element 112 interacts with and is shaped or redistributed by two shaping elements 114. This in turn increases the size of the generated lesion. The microwave field profile is substantially confined to the regions of radiating element 112 and two shaping elements 114 without substantially extending to coaxial cable 102. The coaxial cable 102 in the embodiment in FIG. 15A herein is IW70 coaxial cable from Insulated Wire, Danbury, Conn. The inner conductor in this cable is Ag plated Cu with an OD of 0.018 inches. The outer conductor is made of Ag plated Cu. The outermost layer is a Teflon jacket. The total OD of the coaxial cable is 0.068 inches. This IW70 cable is used as an example only. Several other coaxial cables or other microwave transmission lines can be used to construct any of the devices herein. In any of the embodiments disclosed herein, coaxial cable 102 may comprise an inner conductor 108 made of a Nitinol wire having an outer cladding or plating made of Ag, Au, Pt or any other highly conductive metal. Examples of methods that can be used to add the outer layer on the Nitinol wire include, but are not limited to: electroplating, electro-deposition or cladding. In one embodiment, the design of the remaining elements of coaxial cable 102 (dielectric 110, outer conductor 106 and outer jacket 118) is the same as in the IW70 cable. The Nitinol wire may have shape-memory or superelastic properties. In one embodiment, one or more portions of the Nitinol wire are heat-shaped in a desired geometry.

Figure 15B:
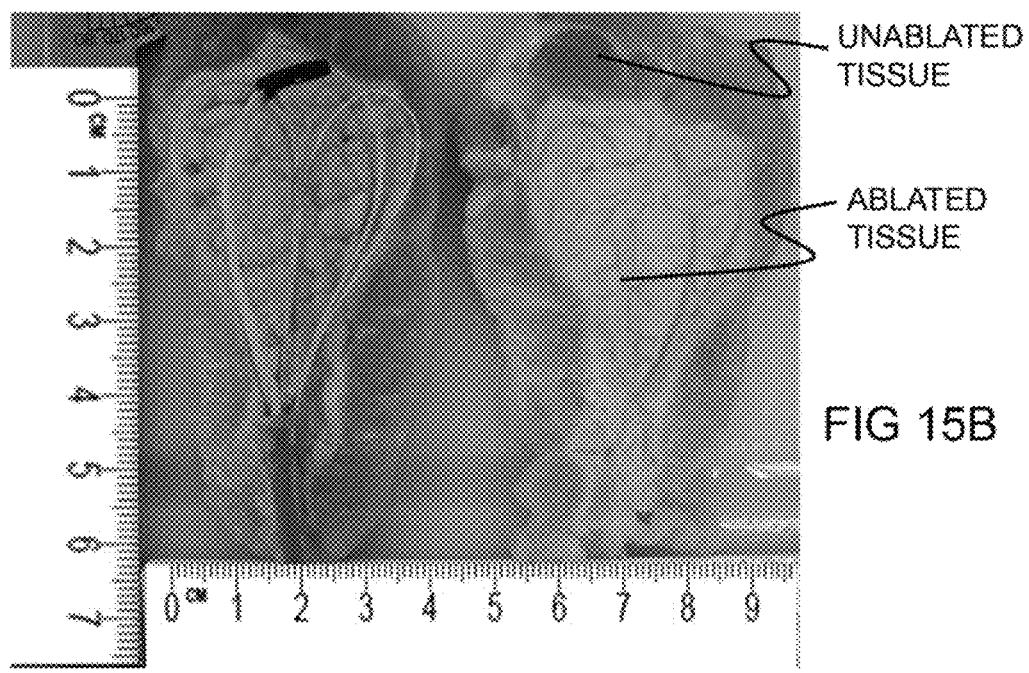
FIG. 15B shows the placement of the antenna of FIG. 15A between two opposite tissue surfaces for an ablation procedure and the resulting ablation pattern that is obtained.

FIG. 15B shows the placement of the antenna of FIG. 15A between two opposite tissue surfaces for an ablation procedure and the resulting ablation pattern that is obtained. In FIG. 15B two opposing slices of porcine muscle tissue at 37 C were used to demonstrate the ablation profile. To create the lesion in FIG. 15B, ablation power was delivered from a 0.915 MHz microwave generator at 90-100 W and the ablation time was 60 s. FIG. 15B shows a substantially uniform ablation without charring that simulates an endometrial ablation.

Figure 15C:
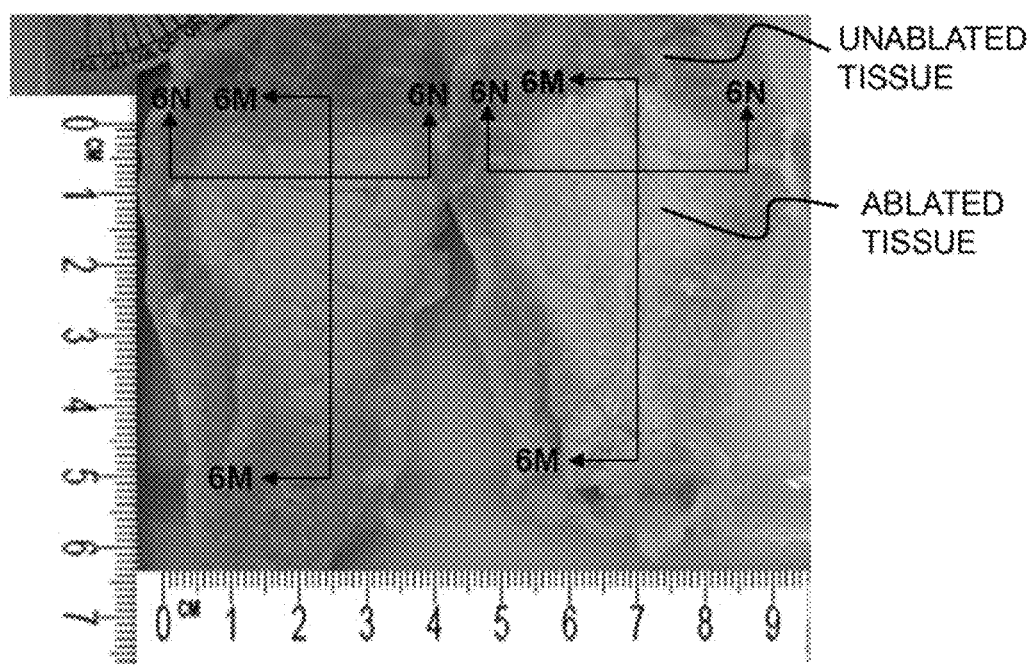
FIG. 15C shows the reverse surfaces of the tissues of FIG. 15B demonstrating trans-mural lesions.

FIG. 15C shows the reverse surfaces of the tissues of FIG. 15B demonstrating trans-mural lesions. Further, FIG. 15C shows that there are no gaps in the lesion pattern. Further, the lesion depth tapers off towards the edges of the lesion. Thus antenna 104 is capable of ablating uterine endometrium such that the resulting lesion is deeper in the center of the uterus and shallower in the cornual and lower uterine regions.

Figures 15D, 15E:
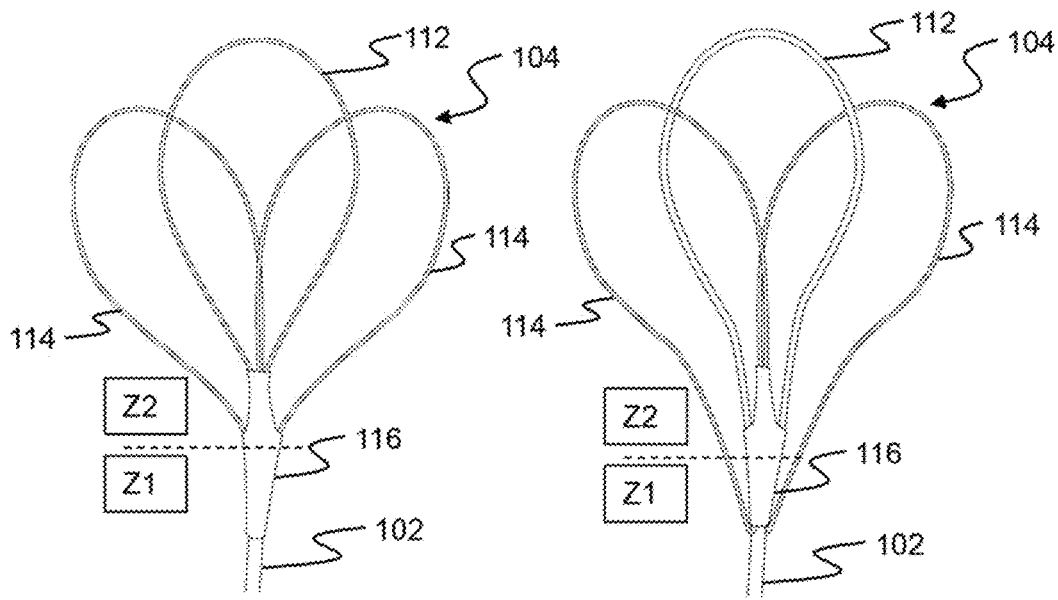

FIG. 15D shows a view of an embodiment of an antenna that comprises a single radiating element and two shaping elements. In this embodiment, a looped radiating element 112 emerges from the distal end of transmission line 102. The proximal portion of radiating element 112 is covered with an antenna dielectric 116 as shown. The distal end of radiating element 112 is also enclosed within the antenna dielectric 116. Two shaping elements 114 are located on symmetrically on either side of radiating element 112. The proximal ends of the two shaping elements 114 are electrically connected to the distal end of a portion of the transmission line (e.g. the outer conductor of a coaxial cable 102). The free ends of shaping elements 114 point in the proximal direction and are located within the antenna dielectric 116. The free ends of shaping elements 114 are in electrical conduction with each other and are electrically insulated from portions of radiating element 112. In addition to locally modifying the dielectric properties of antenna 104, this antenna dielectric 116 may also be used to mechanically hold together various portions of antenna 104.

FIG. 15E shows a view of an embodiment of an antenna that comprises a single radiating element and two shaping elements. The embodiment of antenna 104 in FIG. 15E is similar to the embodiment of antenna 104 in FIG. 15D. However, in this embodiment, the proximal ends of shaping elements 114 are electrically connected to a portion of the transmission line (e.g. the outer conductor of a coaxial cable 102) that is located proximal to the distal end of the transmission lien 102.

Figures 15F, 15G:
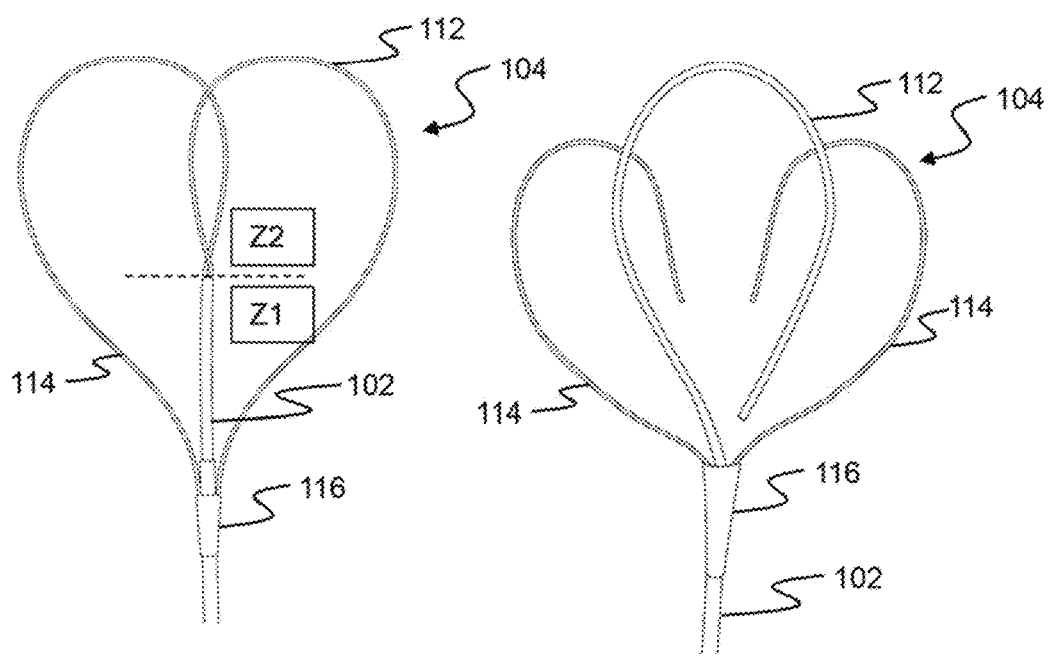

FIG. 15F shows a view of an embodiment of an antenna that comprises a single radiating element and a single shaping element. In this embodiment, radiating element 112 emerges distally from the distal end of transmission line 102. One end of shaping element 114 is mechanically connected to the distal end of transmission line 102. Radiating element 112 and shaping element 114 cross each other and are connected to regions of transmission line 102 proximal to the distal end of transmission line 102. Radiating element 112 is mechanically, non-conductively connected to a region of transmission line 102 proximal to the distal end of transmission line 102. Whereas shaping element 114 is electrically connected to a region of transmission line 102 proximal to the distal end of transmission line 102. Radiating element 112 may be covered with an antenna dielectric 116. A part of the microwave field in this case lies proximal to the distal end of transmission line 102. The length of one or both of radiating element 112 and shaping element 114 may be about three quarters of the effective wavelength of the microwave energy.

FIG. 15G shows a view of an embodiment of an antenna that comprises a single radiating element and two shaping elements. The design of antenna 104 in FIG. 15G is similar to antenna 104 in FIG. 15A. However, in the embodiment in FIG. 15G, two shaping elements 114 are not joined to each other. Further, the distal ends of two shaping elements 114 terminate at points that are more distal than the corresponding termination points on antenna 104 in FIG. 15A. Also, in FIG. 15G, a layer of antenna dielectric 116 may be used to cover the junction region between antenna 104 and transmission line 102. In an alternate embodiment, the lengths of shaping elements 114 in FIG. 15G may be longer than three quarters of the effective wavelength of the microwave energy.

Figures 15H, 15I:
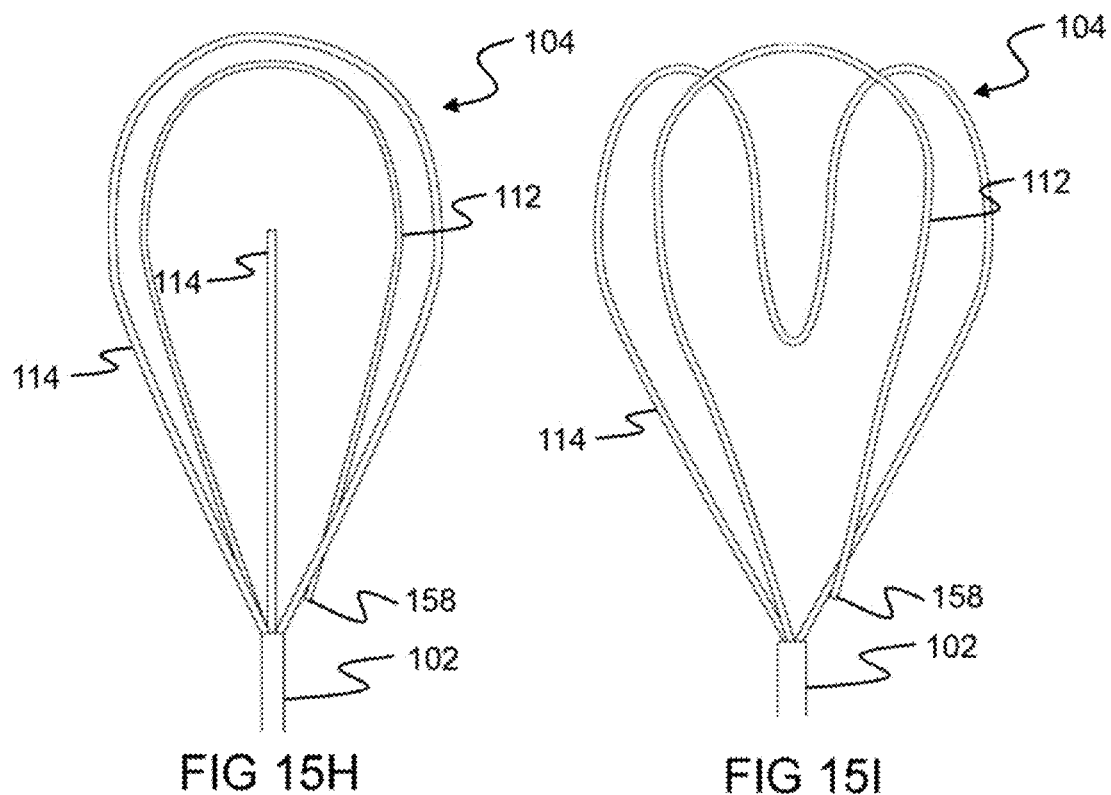

FIG. 15H shows a view of an embodiment of an antenna that comprises a single radiating element and two shaping elements. In this embodiment, radiating element 112 is similar to radiating element 112 of FIG. 15A. A first shaping element 114 is a closed loop and is located around radiating element 112 as shown. Both ends of the closed loop are electrically connected to a portion of the distal end of transmission line 102. Antenna 104 further comprises a linear shaping element 114 arranged parallel to the distal end of transmission line and located at the center of antenna 104. Linear shaping element 114 is also electrically connected to a portion of the distal end of transmission line 102. The distal end of linear shaping element 114 terminates proximally to the distal most portion of antenna 104.

FIG. 15I shows a view of an embodiment of an antenna that comprises a single radiating element and a single shaping element. In this embodiment, radiating element 112 is similar to radiating element 112 of FIG. 15A. Shaping element 114 is heart shaped and is located around radiating element 112 as shown. Shaping element 114 is electrically connected to a portion of the distal end of transmission line 102.

Figure 15J:
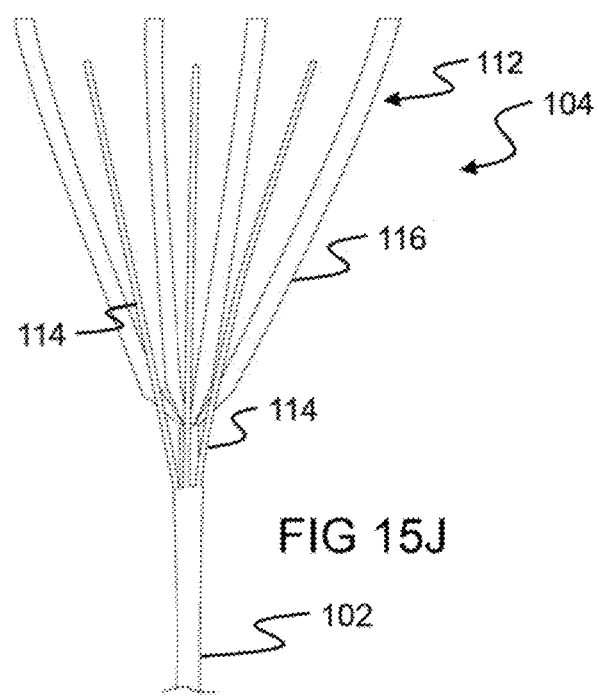

FIG. 15J shows a view of an embodiment of an antenna that comprises multiple radiating elements and multiple shaping elements. Multiple shaping elements 114 are electrically connected to a portion of the transmission line 102. Some or all of multiple radiating elements 112 may be covered with antenna dielectric 116. Multiple radiating elements 112 and multiple shaping elements 114 are placed in alternating fashion to enhance microwave field interaction coupling between multiple radiating elements 112 and multiple shaping elements 114. Although the embodiment shows 4 radiating element 112 and 3 shaping elements 114, alternate embodiments are possible comprising between 2-64 radiating elements 112 and between 2-64 shaping elements 114.

FIG. 15K shows a view of an embodiment of an antenna that comprises a single radiating element and a spirally shaped shaping element. Antenna 104 comprises a looped radiating element 112. An antenna dielectric 116 covers at least the distal end of radiating element 112. The length of radiating element 112 may be three quarters of the effective wavelength of the microwave energy. Spirally arranged shaping element 114 may be a continuation of outer conductor of a coaxial cable 102 or may be a conductive element electrically connected to a shielding element of a transmission line 102.

FIG. 15L shows a view of an embodiment of an antenna that comprises a single radiating element and two shaping elements. In FIG. 15L, a looped radiating element 112 having a distal end 158 is positioned roughly at the center of the axis of antenna 104. Looped radiating element 112 may be formed by an extension of inner conductor of coaxial cable 102 and may be covered with antenna dielectric 116. The length of radiating element 112 may be three quarters of the effective wavelength of the microwave energy. In the embodiment shown, two shaping elements 114 are non-identical and are arranged on either side of radiating element 112. In one embodiment, two shaping elements 114 are formed by an extension of an outer conductor of coaxial cable 102. In an alternate embodiment, shaping elements 114 may be identical and symmetrically arranged on either side of radiating element 112.

FIG. 15M shows a view of an embodiment of an antenna that comprises a single radiating element and a loop shaped shaping element. In FIG. 15M, radiating element 112 may be similar in design to a monopole antenna. In one embodiment, the proximal side of looped radiating element 114 may be formed by formed by an extension of the outer conductor of the coaxial cable 102. The distal side of looped radiating element 114 may be formed by an elongate conductor that is attached to the extension of the outer conductor of the coaxial cable 102 to complete the loop. In an alternate embodiment, a single conductor may be used to form looped shaping element 114. The proximal ends of looped shaping element 114 are electrically connected to the shielding element of the transmission line 102.

FIG. 15N shows a view of an embodiment of an antenna that comprises a single radiating element and two shaping elements. In FIG. 15L, a radiating element 112 having a distal end 158 is in a wavy or zig-zag configuration and is positioned roughly at the center of antenna 104. Radiating element 112 may be formed by an extension of inner conductor of coaxial cable 102 and may be covered with antenna dielectric 116. The length of radiating element 112 may be three quarters of the effective wavelength of the microwave energy. The width of the configuration of radiating element 112 gradually increases in the distal direction. In the embodiment shown, two shaping elements 114 are arranged on either side of radiating element 112.

FIGS. 15O-15Q show embodiments of antenna 104 comprising mechanisms to ensure proper deployment of antenna 104 in the anatomy. In FIG. 15O, one or both of radiating element 112 and shaping element 114 are made of shape memory or super-elastic materials such as Nitinol. Antenna 104 comprises a radiating element 112 covered with antenna dielectric 116. Radiating element 112 emerges at an angle to distal end of transmission line 102. Radiating element 112 is deployed in a bent shape as shown in FIG. 15O. Shaping element 114 is electrically connected to the shielding element of transmission line 102. Shaping element 114 is deployed in a bent shape as shown in FIG. 15Q. The length of one or both of radiating element 112 and shaping element 114 may be about three quarters of the effective wavelength of the microwave energy. The shape memory or super-elastic properties of antenna 104 enable proper deployment of antenna 104 in the anatomy. The design of antenna 104 in FIG. 15P is substantially similar to antenna 104 in FIG. 15O. However, in FIG. 15P, antenna 104 may or may not be made of shape memory or super-elastic materials. Antenna 104 in FIG. 15P is embedded in a substantially planar region of a rigid or flexible antenna dielectric 116. Antenna dielectric 116 fixes the relative positions of radiating element 112 and shaping element 114 thereby ensuring proper deployment in the anatomy. The design of antenna 104 in FIG. 15Q is substantially similar to antenna 104 in FIG. 15O. However, in FIG. 15Q, antenna 104 may or may not be made of shape memory or super-elastic materials. Antenna 104 in FIG. 15P comprises one or more rigid or flexible antenna dielectrics 116 in the form of struts or connection elements connecting radiating element 112 and shaping element 114. Antenna dielectric 116 struts or connection elements fix the relative positions of radiating element 112 and shaping element 114 thereby ensuring proper deployment in the anatomy.

In a method embodiment, a user is provided with antennas 104 of 2 sizes. The user can select the appropriately sized antenna 104 based on a pre-procedure evaluation. In one embodiment, the two antennas are scaled versions of each other. In another embodiment, not all elements of the antenna 104 are scaled up or down in the same proportion. For example, ratio of the thicknesses of the dielectric on the radiating elements 112 may or may not be the same as the ratio of the sizes of radiating elements 112. The materials of construction of elements of the two antennas 104 may be same or different. Additional elements may be added on one or more of the different sized antennas 104. The larger antenna 104 may be used to treat target tissue lying in a certain larger size range and the smaller antenna 104 may be used to treat target tissue lying in a certain smaller size range. The two size ranges may overlap or be non-overlapping. The usage parameters (e.g. energy delivery time, energy delivery power, etc.) during the use of the devices may be same or different. The formulas used for calculating the usage parameters may be same or different.

In one method embodiment, the duty cycle of microwave power delivery varies during the course of an ablation. In one such embodiment, during an initial stage of an ablation, microwave power is delivered at a higher duty cycle and during a later stage of the ablation, microwave power is delivered at a lower duty cycle. In one such embodiment, microwave power is delivered continuously (i.e. at 100% duty cycle) during the initial phase of an ablation to raise the temperature of target tissue to a desired level or within a desired temperature range. Thereafter, microwave power is delivered at less than 100% duty cycle to maintain the temperature of target tissue at the desired level or within the desired temperature range for a desired period of time. In one embodiment, the desired level of temperature of target tissue is 55-75 C. In one embodiment, the change in microwave duty cycle is performed based on a temperature feedback. In one embodiment, the change in microwave duty cycle is performed automatically by a microwave generator after a pre-programmed time.

The microwave duty cycle may be changed automatically by a microwave generator based on input data of pulsatile flow of blood. In one example, during higher blood flow, a higher duty cycle may be used and during lower blood flow, a lower duty cycle may be used. This will avoid excessive energy delivery. In another example, during lower blood flow, a higher duty cycle may be used. This may be used for example, to achieve a greater amount of ablation. In one embodiment, the system is programmed to deliver a therapy that uses temperature feedback to adjust the duty cycle during the therapy. Such manipulation of the duty cycle of microwave power deliver may be used in any of the treatments disclosed herein including, but not limited to: microwave endometrial ablation, ablation of portion of the heart, ablation of vascular tissue, etc.

Similar method and device embodiments are envisioned wherein the magnitude of microwave power delivered to tissue is varied instead of varying the duty cycle. That is an increased microwave power is delivered instead of increasing the duty cycle and a reduced microwave power is delivered instead of reducing the duty cycle.

A treatment assembly comprising a microwave antenna and one or more steerable or non-steerable catheters may be introduced via a trans-esophageal approach into the esophagus. Thereafter, the treatment assembly may used to ablate an abnormal esophageal surface layer to cure Barrett's Esophagus. A treatment assembly comprising a microwave antenna and one or more steerable or non-steerable catheters may be introduced via a trans-cervical approach into the uterine cavity to ablate the uterine endometrium or other tissues of the uterine wall. An ultrasound imaging device may be used to visualize the anatomy and/or the treatment assembly. The treatment assemblies may be used to orient antenna 104 perpendicularly or parallel to the longitudinal axis of anatomical lumens. Antenna 104 may be moved relative to the longitudinal axis of the anatomical lumens or cavities. For example, antenna 104 may be rotated or translated relative to the longitudinal axis to position antenna 104 at various locations in the anatomical lumens or cavities. Such motions of antenna 104 may be used to position antenna 104 to ablate or otherwise treat the entire cavity or lumen wall or an entire circumferential region of the cavity or lumen wall.

Helical antenna 104 configurations such as shown in FIG. 3D are especially suited to contact the internal lining of one or more anatomical cavities of lumens. In addition to other movements disclosed herein, the outer diameter and/or length of the helical shaped antenna 104 may be changed to obtain better contact with target tissue. For example, the outer diameter of helical antenna 104 in FIG. 3D may be increased to increase the force exerted on the surrounding tissue by antenna 104. In a particular embodiment, a helical antenna 104 is used to heat one or more regions of a target vein for treating venous reflux disease. A helical configuration of antenna 104 may be created by one or more of: introducing antenna 104 in a helical introducing catheter or tube, having a pre-shaped helical antenna 104, twisting a sufficiently rigid device attached to a portion of antenna 104, and pulling or pushing a sufficiently rigid device attached to a portion of antenna 104.

Any of the ablation devices 100 disclosed herein or an introducing catheter or sheath used to introduce an ablation device 100 may comprise a fluid transport lumen. The fluid transport lumen may extend from a proximal region of ablation device 100 or the introducing catheter or sheath till a distal region of ablation device 100 or the introducing catheter or sheath that is placed inside the patient's body. The fluid transport lumen may be used for one or more of: evacuating liquids or gases from the anatomy; introducing liquids inside the body such as anesthetics, contrast agents, cauterizing agents, alcohols, thermal cooling agents, a fluid dielectric medium that surrounds antenna 104, antibiotics and other drugs, saline and flushing solutions; introducing gases inside the body such as carbon dioxide for distending a cavity (e.g. the uterine or peritoneal cavity) or detecting perforation of a cavity; applying suction to collapse a tissue region around the antenna 104. Suction may be applied inside a cavity (e.g. the uterine cavity) to increase the contact of antenna 104 with lining of the cavity. When a gas such as carbon dioxide is used for distending the uterine cavity and/or for detecting perforation of the uterus, the gas may be delivered at a pressure between 20-200 mmHg.

Any of the devices disclosed herein including any ablation device 100 disclosed herein may comprise a device transport lumen. The device transport lumen may extend from a proximal region of ablation device 100 till a distal region of ablation device 100 that is placed at a desired location in the patient's body. The device transport lumen may be used for one or more of: introducing one or more elongate diagnostic and/or therapeutic devices in the body, introducing ablation device 100 over a guidewire or other introducing device and introducing an imaging or visualization device.

Any of the devices disclosed herein may comprise a cooling modality to cool one or more regions of the device. For example, a device may comprise a cooling jacket or another cooling modality to cool one or more of: a surface of the device, a shaft of the device and an antenna of the device.

Any of the devices disclosed herein may comprise one or more of: an impedance measuring modality, a temperature measuring modality and an electrophysiological signal measuring modality. In one embodiment, a device disclosed herein comprises a radiometric temperature sensing modality. This radiometric temperature sensing modality may be used to non-invasively measure of temperature at the surface or at a deeper region of tissue. This in turn can be used to obtain real-time feedback about the effectiveness of energy delivery by the device.

Any of the antennas 104 disclosed herein may comprise additional deployment features used to convert an antenna 104 from a non-working configuration wherein antenna 104 is incapable of or sub-optimally capable of performing the desired function to a working configuration wherein antenna 104 is capable of performing a desired function. In one embodiment, a pull wire may be used to pull one or more regions of antenna 104 to change the shape of antenna 104 from a non-working configuration to a working configuration. In another embodiment, a sufficiently rigid shaft comprising a coaxial cable 102 may be used to push one or more regions of antenna 104 against tissue to change the shape of antenna 104 from a non-working configuration to a working configuration.

Any of the antennas 104 disclosed herein may comprise or be used in combination with a microwave shielding or absorbing element. The microwave shielding or absorbing element may shield a majority of or a part of the microwave field emitted by antenna 104. Examples of microwave shielding or absorbing elements include, but are not limited to: inflatable or non-inflatable balloons, hollow structures filled with air or a circulating or non-circulating fluid, metallic wires or meshes, metallic films or other flattened structures, gels or other conformable structures, structures filled or wetted with water, structures designed to circulate one or more fluids on the surface of antenna 104, cooling modalities and mechanical spacers made of dielectric materials. In a particular embodiment, the microwave shielding or absorbing element is disc-shaped. In another embodiment, the microwave shielding or absorbing element is slidably positioned relative to radiating element 112. In this embodiment, the shape of microwave field emitted by antenna 104 may be changed by sliding the microwave shielding or absorbing element relative to radiating element 112. In one such embodiment, a tubular microwave shielding or absorbing element surrounds a substantially linear antenna 104. The length of the microwave field shape and the resulting lesion length by antenna 104 may be changed by sliding the microwave shielding or absorbing element relative to antenna 104. Such microwave shielding or absorbing elements in combination with an antenna 104 disclosed herein may be used to ablate a local region of tissue (e.g. a part of the uterine endometrium or a vascular endothelium) or to ablate only a single surface of the tissue (e.g. a single surface of the uterine endometrium).

Any of the antennas 104 disclosed herein may comprise or be used in combination with a constraining element that not only shapes the microwave field profile of antenna 104 also mechanically shapes antenna 104. Antenna 104 may be mechanically constrained by constraining element 146 before insertion near or into the target tissue. The concept of constraining antenna 104 in an introducing catheter or sheath has been previously disclosed. FIGS. 16A-16D show various views of an embodiment of a constraining element 146 that is usable for constraining antenna 104 to change or constrain the shape of antenna 104. In one embodiment, constraining element 146 comprises a substantially rectangular cavity or depression 166 or a chamber, gap, hole or pocket designed to constrain antenna 104 in a more rectangular shape. Such a constrained antenna 104 may be used for deep or surface ablation of tissue. In one embodiment, a constrained antenna 104 is used to ablate soft tissue by placing antenna 104 between the target tissue and constraining element 146. Constraining element 146 may be used as a shield to protect collateral tissue damage by preventing any ablation on the side of antenna 104 opposite to target tissue. Constraining element 146 may comprise one or more metallic elements for microwave shielding. Constraining element 146 may be made from suitable dielectric materials including, but not limited to PTFE, EPTFE, silicone and ABS. In another embodiment, a constrained antenna 104 is used inside the abdominal cavity to ablate an abdominal organ. A constrained antenna 104 may be used to ablate a surface of an organ e.g. the outer surface of the organ. FIG. 16A shows a view of a combination of constraining element 146 along with ablation device 100 positioned in the constraining element 146 such that antenna 104 is constrained in rectangular cavity or depression 166. In the embodiment in FIG. 16A, antenna 104 comprises a radiating element 112 and a shaping element 114 that is in electrical contact with outer conductor of coaxial cable 102. Antenna 104 is enclosed in a constraining element 146 that mechanically constrains antenna 104. FIG. 16B shows a perspective view of constraining element 146 comprising a cavity or depression 166 usable to mechanically shape antenna 104. FIG. 16C is a side view of constraining element 146 of FIG. 16B showing cavity or depression 166. FIG. 16D shows a view of the crossection of constraining element 146 through plane 16D-16D. Embodiments of constraining elements 146 may be combined with any of the antenna 104 embodiments disclosed herein to reduce the microwave field intensity on one side of antenna 104.

Any of the devices and elements disclosed herein may be controlled by robotic control. Further, any of the devices disclosed herein may be introduced and/or navigated and/or operated using a robotic system. Examples of such robotic systems include, but are not limited to the Sense™ Robotic Catheter System made by Hansen Medical, Inc. and the da Vinci® Surgical System made by Intuitive Surgical, Inc. For example, any introducing sheath used to introduce an antenna 104 may be a robotic catheter with an introducing lumen.

Any of the devices disclosed herein may be introduced and/or manipulated through one or more lumens of one or more elongate sheaths or catheters. Several such treatment assemblies comprising an ablation device and one or more elongate sheaths or catheters are possible. For Example, a treatment assembly comprising an ablation device 100 slidably positioned in a lumen of an introducing sheath may be designed. One or more of such introducing sheaths or catheters can comprise one or more steering mechanisms. Examples of such steering mechanisms include, but are not limited to pull wires, pre-shaped tubular sheaths or stylet structures.

Any of the devices disclosed herein may have a varying degree of flexibility along the length of the device or antenna 104.

In those cases where a device requires connection to an auxiliary component (e.g., a power supply, imaging monitor, fluid source, etc.) a handle of the device can include the desired means for connection.

Any of the cardiac diagnostic or treatment procedures disclosed herein may include the use of a pericardial device placed in the pericardial space or around the epicardium. The pericardial device may be inserted by a sub-xiphoid approach. Such devices may be used for one or more of: preventing excessive ablation, confirming trans-mural nature of an ablation, cooling the surrounding anatomy, preventing unwanted damage to the phrenic nerve or to the esophagus, etc. In one such embodiment, an ICE (intra-cardiac echocardiography) probe may be inserted into the pericardial space or around the epicardium. The ICE probe may be used to visualize one or more device and/or one or more anatomical regions. In another embodiment, a deflectable device is inserted into the pericardial space or around the epicardium. The device is deflected or otherwise manipulated to create a space or increase the distance between the posterior aspect of the heart and the esophagus. This may be used to increase the safety of cardiac ablation procedures. In another embodiment, an esophagus protecting device is inserted in the pericardial space or around the epicardium such that the device is positioned between the posterior aspect of the heart and the esophagus. Such a device may be used to prevent esophageal injury during cardiac ablation procedure. Examples of such devices include, but are not limited to: inflatable devices, spacing device, devices with cooling mechanisms, etc. In one embodiment, a mapping catheter comprising one or more electrodes adapted for electrophysiological mapping is inserted in the pericardial space or around the epicardium. The mapping catheter may be used for measuring electrophysiological signals from cardiac tissue. In one embodiment, the mapping catheter is used for confirming transmural nature of a lesion. In one embodiment, the mapping catheter may be used to map the activation patterns of electrophysiological signals in cardiac tissue. In one embodiment, the pericardial device is a hollow catheter to deliver one or more fluids in the anatomy. Any of the fluids mentioned herein may be delivered by such catheters. In one embodiment, the pericardial device comprises an antenna printed on a flat substrate as shown in FIG. 5A. In one embodiment, the pericardial device comprises an ablation modality (e.g. a microwave antenna, RF electrodes, etc.) to ablate one or more cardiac regions to treat one or more of: atrial fibrillation, ventricular tachycardia, atrial flutter and other arrhythmias. The pericardial device may be used to deploy navigation markers used in 3-D surgical electroanatomical navigation systems in the pericardial space or around the epicardium. Examples of systems that use such navigation markers include, but are not limited to: Carto navigation system (Biosense-Webster, Diamond Bar, Calif.) and the EnSite NavX system (St. Jude Medical, St. Paul, Minn.). In one embodiment, the pericardial device is a hollow catheter that is used to introduce multiple mapping catheters. Each of the mapping catheters may have a tether. The tethers of each of the multiple mapping catheters may be folded back into the hollow catheter.

In any of the method embodiments herein, pre-procedure anatomical data may be obtained by imaging the anatomy. This anatomical data may be used to tailor a method for the particular patient. In one embodiment, the anatomical data is used to adjust a size or shape parameter of ablation device 100. In another embodiment, the anatomical data is used to determine a treatment parameter e.g. ablation power, ablation time, etc. The anatomical data may be obtained by one or more of: ultrasound imaging with or without contrast agent, fluoroscopic or X-ray imaging with or without a contrast agent, MRI with or without a contrast agent, PET scan, endoscopy and using a mechanical size determining devices (e.g. a uterine sound, an elongated device with distance markings, etc.).

Ablation device 100 disclosed herein may be inserted and/or used blindly i.e. without using any additional imaging modality.

Ablation device 100 disclosed herein may be inserted and/or used under endoscopic (e.g. using hysteroscopy, cystoscopy, endoscopy, laparoscopy, flexible endoscopy, etc.) guidance.

Ablation device 100 disclosed herein may be inserted and/or used under ultrasonic guidance.

Ablation device 100 disclosed herein may be inserted and/or used under radiological guidance. In one embodiment, ablation device 100 is used under X-ray or fluoroscopic guidance. Ablation device 100 may comprise one or more radiopaque markers to enable the visualization of one or more regions of ablation device 100 under X-ray or fluoroscopic guidance.

Ablation device 100 may comprise a visualization modality or means for coupling to a visualization modality. In one embodiment, the visualization modality (e.g. fiberoptic fibers or other optical imaging modality, ultrasound catheter, etc.) may be embedded in a wall of ablation device 100 and/or an introducing catheter 148. In another embodiment the visualization modality (e.g. fiberoptic fibers or other optical imaging modality, ultrasound catheter, etc.) may be introduced through a lumen of ablation device 100 or introducing catheter 148.

Ablation device 100 may comprise one or more gas or liquid inflatable balloons for doing one or more of: positioning antenna 104, providing a cooling modality, enabling better contact of antenna 104 with target tissue and deploying antenna 104.

Even though a majority of the disclosure uses a coaxial cable as an example of a transmission line, an alternate transmission lines for transmitting microwaves may be used. Examples of such alternate transmission lines for transmitting microwaves include, but are not limited to: waveguides, microstrip lines, strip lines, coplanar waveguides and rectax. In such embodiments, the shaping element(s) 114 may be in electrical conduction with the shielding element of the transmission line. For example, in a strip line, wherein the shielding element is the combination of the two ground planes, shaping element(s) 114 may be in electrical conduction with the combination of the two ground planes. For example, in a hollow metallic waveguide, wherein the shielding element is the electrically conducting wall, shaping element(s) 114 may be in electrical conduction with the electrically conducting wall.

One or more elements described herein may comprise one or more additional treatment modalities. Examples of such additional treatment modalities include, but are not limited to: radiofrequency electrodes including radiofrequency ablation electrodes, heating elements, cryotherapy elements, elements for emitting laser and other radiation, elements for introducing one or more fluids, etc. For example, radiating element 112 and/or shaping element 114 may comprise multiple radiofrequency ablation electrodes. Such radiofrequency ablation electrodes enable the use of the devices disclosed herein in conjunction with other modalities such as radiofrequency ablation. One or more elements described herein may comprise one or more additional diagnostic modalities. Examples of such diagnostic modalities include, but are not limited to: temperature sensors, impedance sensors, electrophysiological signal sensors, visualization elements, etc. For example, radiating element 112 and/or shaping element 114 may comprise multiple temperature sensors.

One or more devices disclosed herein may comprise one or more lubricious coatings. One or more devices disclosed herein may comprise one or more regions that are thermally insulated to protect non-target tissue.

Even though antenna 104 is designed to work well without exact contact with tissue, there may be an advantage if the proper positioning of the antenna 104 is determined just before the ablation. For example, if antenna 104 is not deployed in the preferred working configuration, the lesion may not be therapeutically optimal. The invention herein further includes a non-visual and integrated device that can be used to determine the proper positioning of antenna 104 just before the ablation. The method uses reflectometry to determine the proper positioning. If the antenna is not properly positioned, the antenna may not be well matched. In such a case, the measured reflected power for a particular range of incident power (the power sent to the antenna) will not be within a normal range. Thus by measuring if the reflected power is within a normal range, we can say whether the antenna is properly positioned. An example of such a procedure is as follows. 1. Conduct a series of experiments with the antenna properly positioned in the target tissue, 2. Measure the reflected power level in all the experiments for a particular range of incident power level with the antenna properly positioned in the target tissue, 3. Determine a "normal range" of reflected power level that is to be expected if the antenna is properly positioned in the target tissue, 4. During the endometrial ablation procedure, measure the reflected power level, 5. If the reflected power level is within the normal range, conclude that the antenna is properly positioned. If the reflected power level is not within the normal range, conclude that the antenna is not properly positioned. As an optional extra step, a series of experiments may be conducted with the antenna improperly positioned in the target tissue by having the antenna deployed purposely in imperfect or wrong configuration. This is to determine an "abnormal range" of incident power level that is to be expected if the antenna is not properly positioned in the target tissue.

The reflected power level can be measured by 1. using an external power meter or 2. using a power meter that is in-built within the microwave generator.

Various additional embodiments of antenna 104 may be designed wherein radiating element 112 is a straight or curved or bent or pre-shaped monopole antenna.

In any of the method embodiments herein, the lesion size may be deepened or lengthened or widened by one or more of: increasing the power delivered by the microwave generator, increasing the ablation time, temporary reducing the blood flow to the anatomy, pre-treating the anatomy, etc. Further, the lesion size may be made shallower or shorter or narrower by one or more of: reducing the power delivered by the microwave generator, reducing the ablation time, circulating a cooling agent in the anatomy, pre-treating the anatomy, etc.

The microwave field generated by any antenna 104 disclosed herein may be directed towards a particular direction by a variety of mechanisms. For example, a microwave reflector (e.g. a metallic mesh) may be positioned on one side of a flat or planar ablation portion to generate higher microwave energy intensity on the other side of the flat or planar ablation portion. One or more microwave absorbing or shielding or reflecting materials may be used in combination with the embodiments disclosed herein to direct the microwave field to a particular direction. In one embodiment, the whole or part of shaping element 114 is designed to act as a microwave shield or reflector or absorber.

Devices disclosed herein may be constructed with various orientations of the antenna 104 relative to the region of coaxial cable 102 immediately proximal to antenna 104. For example, devices herein may be designed with an antenna 104 that is substantially parallel to or in the plane of the region of coaxial cable 102 immediately proximal to antenna 104. Devices can also be designed with an antenna 104 oriented at an angle (e.g. 90+/−20 degrees, 45+/−20 degrees) to the region of coaxial cable 102 immediately proximal to antenna 104. This is advantageous to reach hard-to-reach target regions in the body. The relative orientation of whole or portions of antenna 104 relative to the device shaft (e.g. the coaxial cable 102) may be fixed or changeable. For example, there may be a springy joint or region between antenna 104 and the shaft. In another embodiment, there may be an active steering mechanism e.g. a pull wire mechanism to change the relative orientation of whole or portions of antenna 104 relative to the shaft. Such mechanisms may be used for proper positioning of antenna 104 on the target tissue or for navigating the device through the anatomy. For example, an antenna 104 deployed through an endoscope or through a laparoscope port may be deployed and navigated such that antenna 104 lies in the plane of the target tissue.

The user may be supplied several devices of varying size and/or shape. The user may then select the proper device based on his judgment to carry out the ablation. In a particular embodiment, 2 to 3 different devices with antennas 104 of similarly shape but different sizes are supplied. The user then selects the proper device. Such multiple devices may be packaged separately or together. In another embodiment, 2 to 3 different devices with antennas 104 of similar sizes but different shapes are supplied. The user then selects the proper device as per the need. In one method embodiment, the deployment of the device is tailored to the particular target tissue or cavity. In such embodiments, whole or parts of antenna 104 are designed to be deployed in a particular size and/or shape that best fits the particular target tissue or cavity.

Several examples or embodiments of the invention have been discussed herein, but various modifications, additions and deletions may be made to those examples and embodiments without departing from the intended spirit and scope of the invention. Thus, any element, component, method step or attribute of one method or device embodiment may be incorporated into or used for another method or device embodiment, unless to do so would render the resulting method or device embodiment unsuitable for its intended use. For example, several embodiments of ablation devices 100 may be created by combining antenna 104 of one embodiment with a device feature of another embodiment unless to do so would render the resulting device embodiment unsuitable for its intended use. Any suitable antenna disclosed herein may be used to perform any of the methods disclosed herein. If the various steps of a method are disclosed in a particular order, the various steps may be carried out in any other order unless doing so would render the method embodiment unsuitable for its intended use. Various reasonable modifications, additions and deletions of the described examples or embodiments are to be considered equivalents of the described examples or embodiments.

We claim:

1. A medical device for applying a microwave energy from a microwave energy source, the medical device comprising:
    a transmission line having a shielding element;
    a microwave antenna configured to apply microwave energy to tissue, the antenna comprising a radiating member operatively coupled to the microwave energy source via the transmission line, an antenna dielectric and a shaping member electrically coupled to the shielding element, where the shaping member is electrically conductive; and
    where the radiating member comprises a first profile such that application of microwave energy by the radiating member alone produces a first microwave energy field, and where the shaping element comprises a second profile and is positioned to couple with the microwave energy field of the radiating member to shape the first unshaped microwave energy field into a second shaped microwave energy field extending volumetrically around the antenna.

2. The device of claim 1, wherein the antenna is flexible to bend relative to the distal end of the transmission line during clinical use.

3. The device of claim 2, wherein the antenna is flexible to having a compressed pre-deployment size similar to a size of the transmission line.

4. The device of claim 2, wherein the antenna is flexible to change from a linear pre-deployment configuration to a non-linear deployed configuration.

5. The device of claim 1, wherein the first profile of the radiating element comprises a profile selected from the group consisting of a linear profile, a planar profile, or a three-dimensional profile.

6. The device of claim 1, wherein the antenna is connected to the distal end of the transmission line and the radiating member and the shaping member are located distal to the distal end of the transmission line.

7. The device of claim 1, wherein the radiating member comprise a non-linear conductor.

8. The device of claim 1, wherein the radiating member comprises a helical conductor.

9. The device of claim 1, wherein the radiating member comprises an electrically insulated cover to remain insulated from a tissue or the shaping member.

10. The device of claim 1, where the transmission line comprises a coaxial cable having an inner conductor and an outer conductor, where the shielding element is electrically coupled to the outer conductor and where the radiating member is electrically coupled to the inner conductor.

11. The device of claim 1, where the radiating member comprises a length that is an odd multiple of one quarter of the effective wavelength at one of: 433 MHz ISM band, 915 MHz ISM band, 2.45 GHz ISM band and 5.8 GHz ISM band.

12. The device of claim 1, where the radiating member comprises a continuation of a conductor of the transmission line.

13. The device of claim 1, further comprising at least one additional radiating member.

14. The device of claim 1, further comprising at least one additional shaping member.

15. The device of claim 1, where the shaping member is configured to shape the second shaped microwave energy field to be more uniform than the first microwave energy field along a length of the antenna.

16. The device of claim 1, where the shaping member is configured to shape the second shaped microwave energy field distally farther from the distal end of the transmission line than the first microwave energy field.

17. The device of claim 1, where the shaping member is linear.

18. The device of claim 1, wherein the radiating member and shaping member are parallel.

19. The device of claim 1, wherein the radiating member is planar and the shaping member is planar and the plane of radiating member is substantially parallel to the plane of shaping member.

20. The device of claim 1, wherein radiating member encloses the shaping member.

* * * * *